(12) United States Patent
Mastri et al.

(10) Patent No.: US 7,225,964 B2
(45) Date of Patent: *Jun. 5, 2007

(54) SURGICAL STAPLER

(75) Inventors: Dominick L. Mastri, Bridgeport, CT (US); Frank J. Viola, Sandy Hook, CT (US); Thomas W. Alesi, Jr., New Fairfield, CT (US); Robert J. Geiste, Milford, CT (US); Jon Wilson, Fairfield, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/387,409

(22) Filed: Mar. 23, 2006

(65) Prior Publication Data

US 2006/0201990 A1    Sep. 14, 2006

Related U.S. Application Data

(60) Division of application No. 11/186,743, filed on Jul. 20, 2005, which is a continuation of application No. 11/011,355, filed on Dec. 14, 2004, now Pat. No. 7,044,353, which is a continuation of application No. 09/625,886, filed on Jul. 26, 2000, now Pat. No. 6,986,451, which is a continuation of application No. 09/497,647, filed on Feb. 3, 2000, now abandoned, which is a continuation of application No. 09/119,543, filed on Jul. 20, 1998, now Pat. No. 6,032,849, which is a continuation of application No. 08/546,253, filed on Oct. 20, 1995, now Pat. No. 5,782,396, which is a continuation-in-part of application No. 08/520,202, filed on Aug. 28, 1995, now Pat. No. 5,762,256.

(51) Int. Cl.
    *A61B 17/068*    (2006.01)

(52) U.S. Cl. .................. 227/176.1; 227/19; 227/180.1
(58) Field of Classification Search ............. 227/176.1, 227/178.1, 180.1, 19
    See application file for complete search history.

(56) References Cited

U.S. PATENT DOCUMENTS

| 3,079,606 A | 3/1963 | Bobrov et al. |
| 3,490,675 A | 1/1970 | Green et al. |
| 3,777,538 A | 12/1973 | Weatherly et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |

(Continued)

FOREIGN PATENT DOCUMENTS

AU    5476586    9/1986

(Continued)

*Primary Examiner*—Scott A. Smith

(57) ABSTRACT

A surgical device is described herein that can be used to fire different types and sizes of disposable loading units. In a preferred embodiment, the device applies parallel rows of surgical fasteners to body tissue and concomitantly forms an incision between the rows of staples during an endoscopic or laparoscopic surgical procedure. The device can be utilized with disposable loading units configured to apply linear rows of staples measuring from about 15 mm in length to about 60 mm in length and can be used to fire disposable loading units containing surgical clips and individual staples.

18 Claims, 38 Drawing Sheets

U.S. PATENT DOCUMENTS

| | | |
|---|---|---|
| 4,505,414 A | 3/1985 | Filipi |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,892,244 A | 1/1990 | Fox et al. |
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,074,454 A | 12/1991 | Peters |
| 5,083,695 A | 1/1992 | Foslien et al. |
| 5,084,057 A | 1/1992 | Green et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,170,925 A | 12/1992 | Madden et al. |
| 5,171,247 A | 12/1992 | Hughett et al. |
| 5,246,156 A | 9/1993 | Rothfuss et al. |
| RE34,519 E | 1/1994 | Fox et al. |
| 5,282,807 A | 2/1994 | Knoepfler |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,332,142 A | 7/1994 | Robinson et al. |
| 5,336,232 A | 8/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |

| Patent Number | Date | Inventor |
|---|---|---|
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A * | 6/1998 | Mastri et al. ............ 227/176.1 |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A * | 7/1998 | Mastri et al. ............ 227/175.3 |
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,954,259 A | 9/1999 | Viola et al. |
| 5,980,510 A | 11/1999 | Tsonton et al. |
| 6,004,335 A | 12/1999 | Vaitekunas et al. |
| 6,010,054 A | 1/2000 | Johnson et al. |
| 6,032,849 A * | 3/2000 | Mastri et al. ............ 227/176.1 |
| 6,079,606 A | 6/2000 | Milliman et al. |
| 6,109,500 A | 8/2000 | Alli et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,986,451 B1 * | 1/2006 | Mastri et al. ............ 227/176.1 |
| 7,044,353 B2 * | 5/2006 | Mastri et al. ............ 227/176.1 |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0173659 A1 | 9/2004 | Green |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0072827 A1 | 4/2005 | Mollenauer |

| | | | | | |
|---|---|---|---|---|---|
| 2005/0103819 A1 | 5/2005 | Racenet | EP | 0552423 | 7/1993 |
| 2005/0119669 A1 | 6/2005 | Demmy | EP | 0579038 | 1/1994 |
| 2005/0127131 A1 | 6/2005 | Mastri | EP | 0589306 | 3/1994 |
| 2005/0173490 A1 | 8/2005 | Shelton, IV | EP | 0591946 | 4/1994 |
| 2005/0178813 A1 | 8/2005 | Swayze et al. | EP | 0592243 | 4/1994 |
| | | | EP | 0593920 | 4/1994 |

FOREIGN PATENT DOCUMENTS

| | | | | | |
|---|---|---|---|---|---|
| | | | EP | 0598202 | 5/1994 |
| DE | 2744824 | 4/1978 | EP | 0598579 | 5/1994 |
| DE | 2903159 | 1/1980 | EP | 0621006 | 10/1994 |
| DE | 31144135 | 10/1982 | EP | 0621009 | 10/1994 |
| DE | 4213426 | 10/1992 | EP | 0656188 | 6/1995 |
| DE | 4300307 | 7/1994 | EP | 0365153 | 8/1995 |
| EP | 0041022 | 12/1981 | EP | 0666057 | 8/1995 |
| EP | 0136950 | 4/1985 | EP | 0705571 | 4/1996 |
| EP | 0140552 | 5/1985 | FR | 2542188 | 9/1984 |
| EP | 0156774 | 10/1985 | FR | 2660851 | 10/1991 |
| EP | 0216532 | 4/1987 | FR | 2681775 | 10/1991 |
| EP | 0220029 | 4/1987 | GB | 1352554 | 4/1971 |
| EP | 0213817 | 11/1987 | GB | 1452185 | 10/1976 |
| EP | 0273468 | 7/1988 | GB | 1555455 | 11/1979 |
| EP | 0324166 | 7/1989 | GB | 2048685 | 12/1980 |
| EP | 0324635 | 7/1989 | GB | 2070499 | 9/1981 |
| EP | 0324637 | 7/1989 | GB | 2141066 | 12/1984 |
| EP | 0324638 | 7/1989 | GB | 2165559 | 4/1986 |
| EP | 0369324 | 5/1990 | JP | 51-149985 | 1/1975 |
| EP | 0373762 | 6/1990 | RU | 0119846 | 1/1959 |
| EP | 0380025 | 8/1990 | RU | 980703 | 12/1982 |
| EP | 0399701 | 11/1990 | RU | 990220 | 1/1983 |
| EP | 0449394 | 10/1991 | SU | 728848 | 5/1977 |
| EP | 0484677 | 5/1992 | SU | 659146 | 4/1979 |
| EP | 0489436 | 6/1992 | WO | WO 89/10084 | 11/1989 |
| EP | 0503662 | 9/1992 | WO | WO 89/10094 | 11/1989 |
| EP | 0514139 | 11/1992 | WO | WO9210976 | 7/1992 |
| EP | 0536903 | 4/1993 | WO | 9308754 | 5/1993 |
| EP | 0537572 | 4/1993 | WO | WO8302247 | 7/1993 |
| EP | 0539762 | 5/1993 | WO | 9314706 | 8/1993 |
| EP | 0545029 | 6/1993 | | | |
| EP | 0552050 | 7/1993 | * cited by examiner | | |

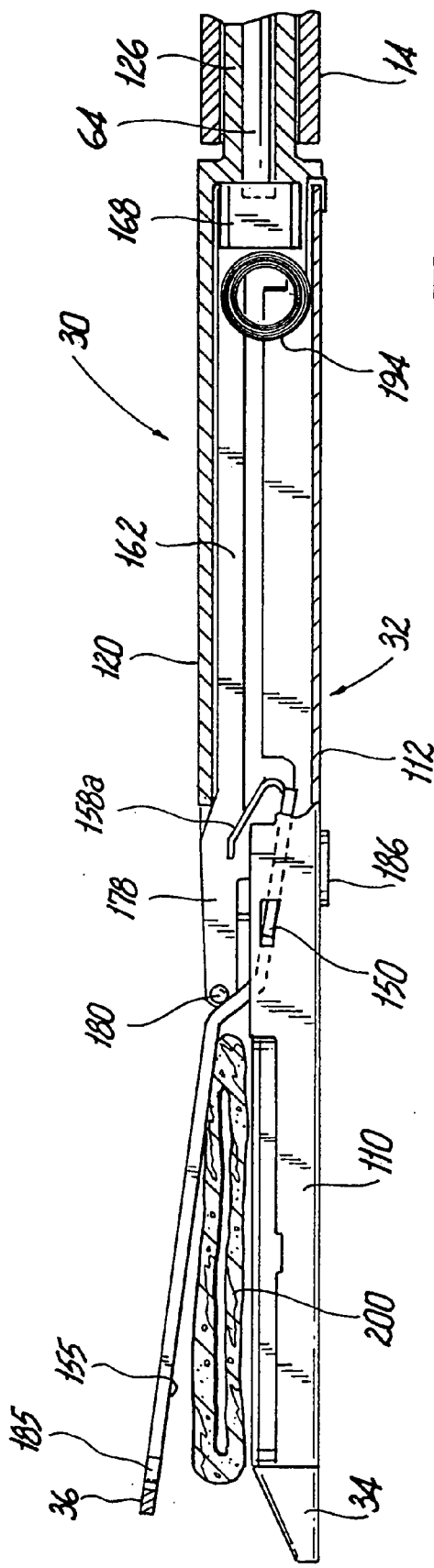
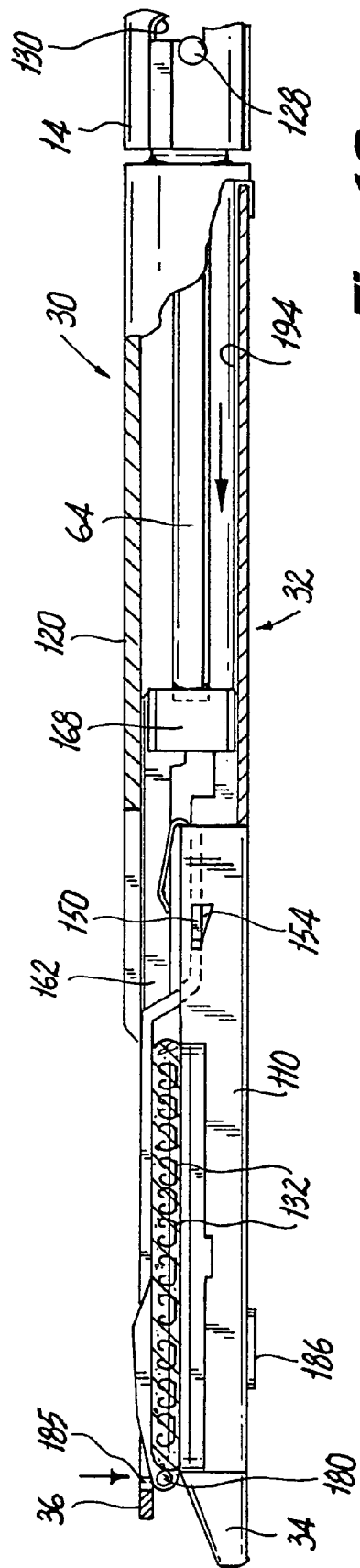
Fig. 12
Fig. 13

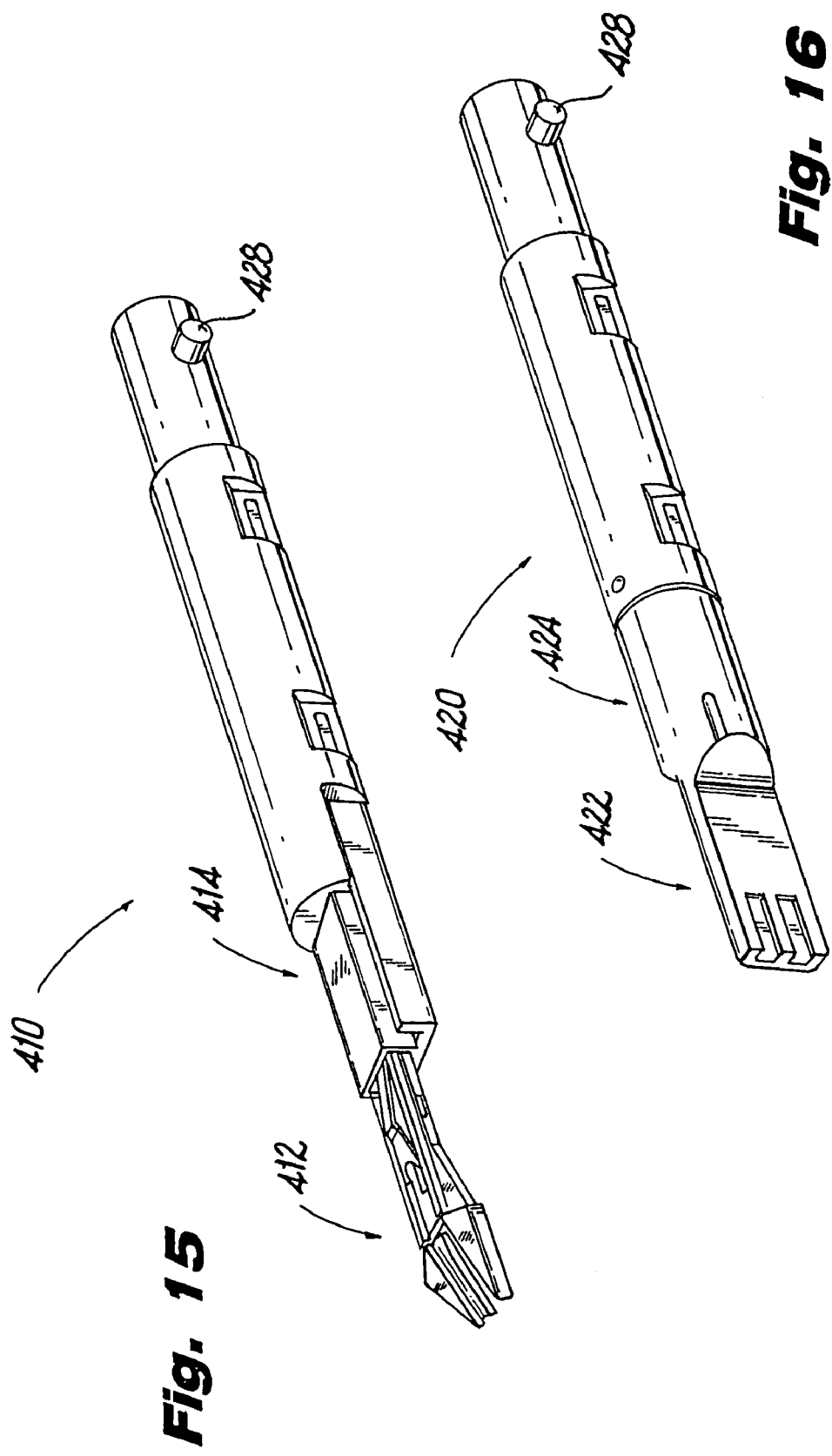

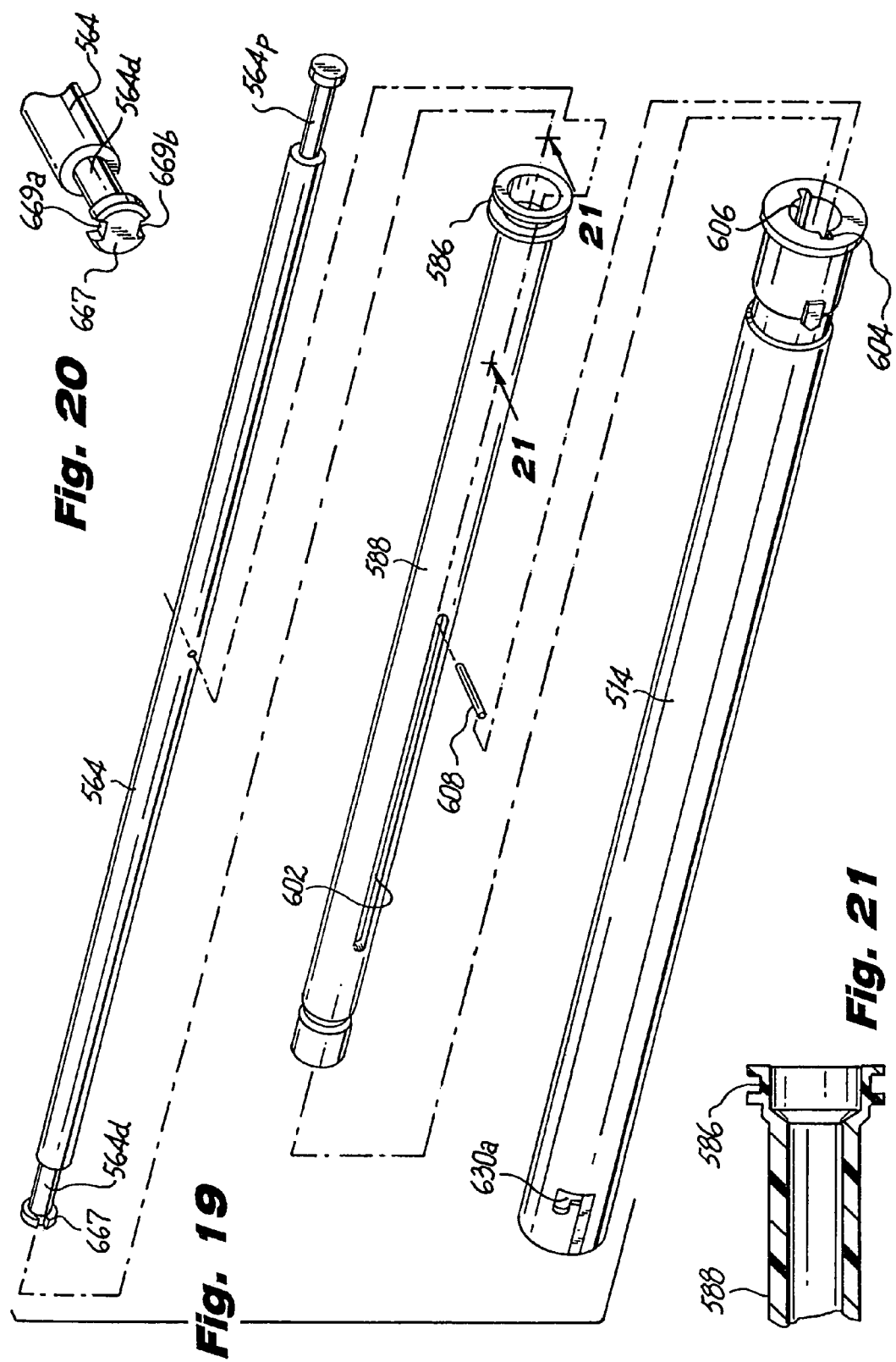

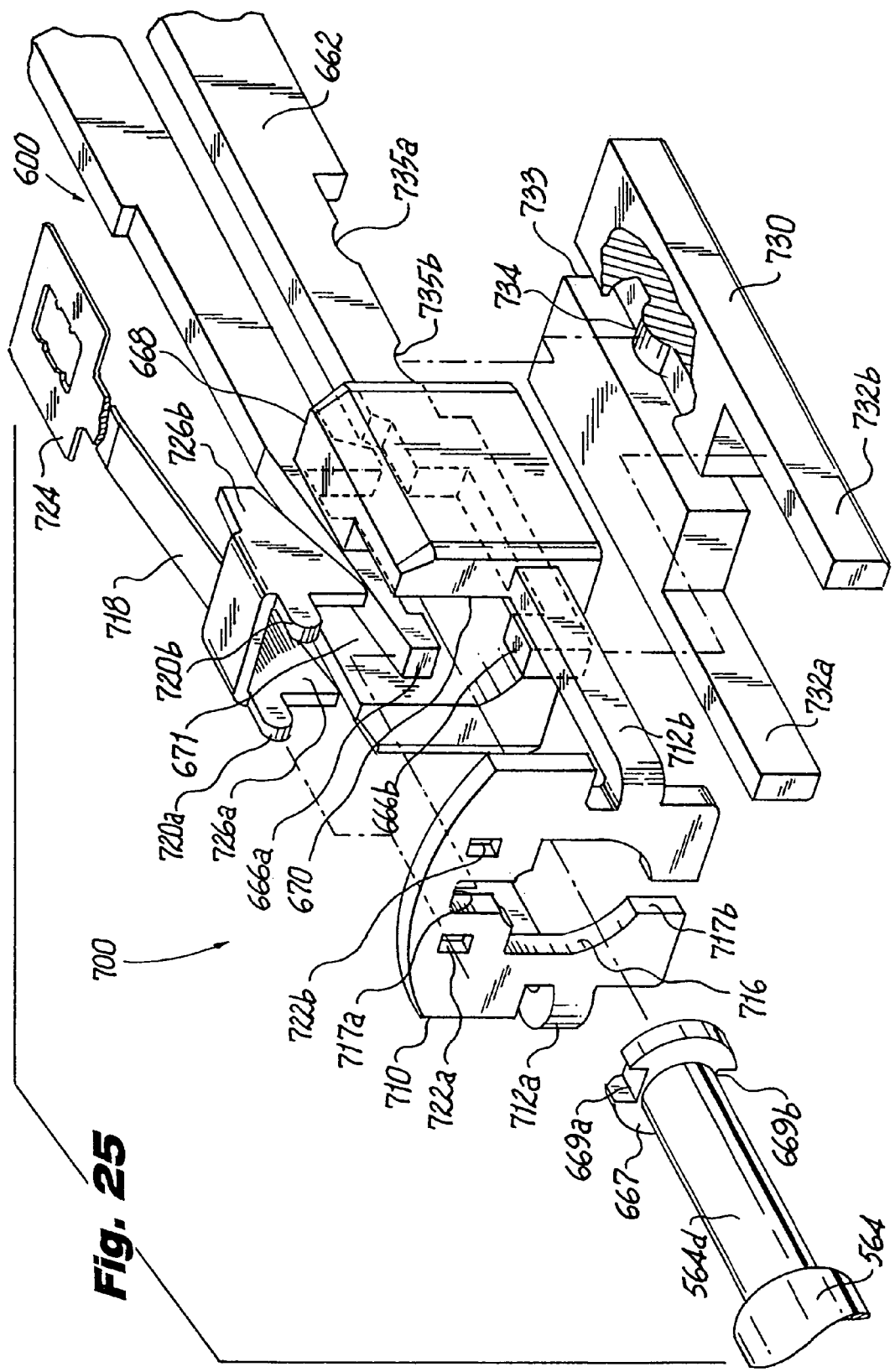

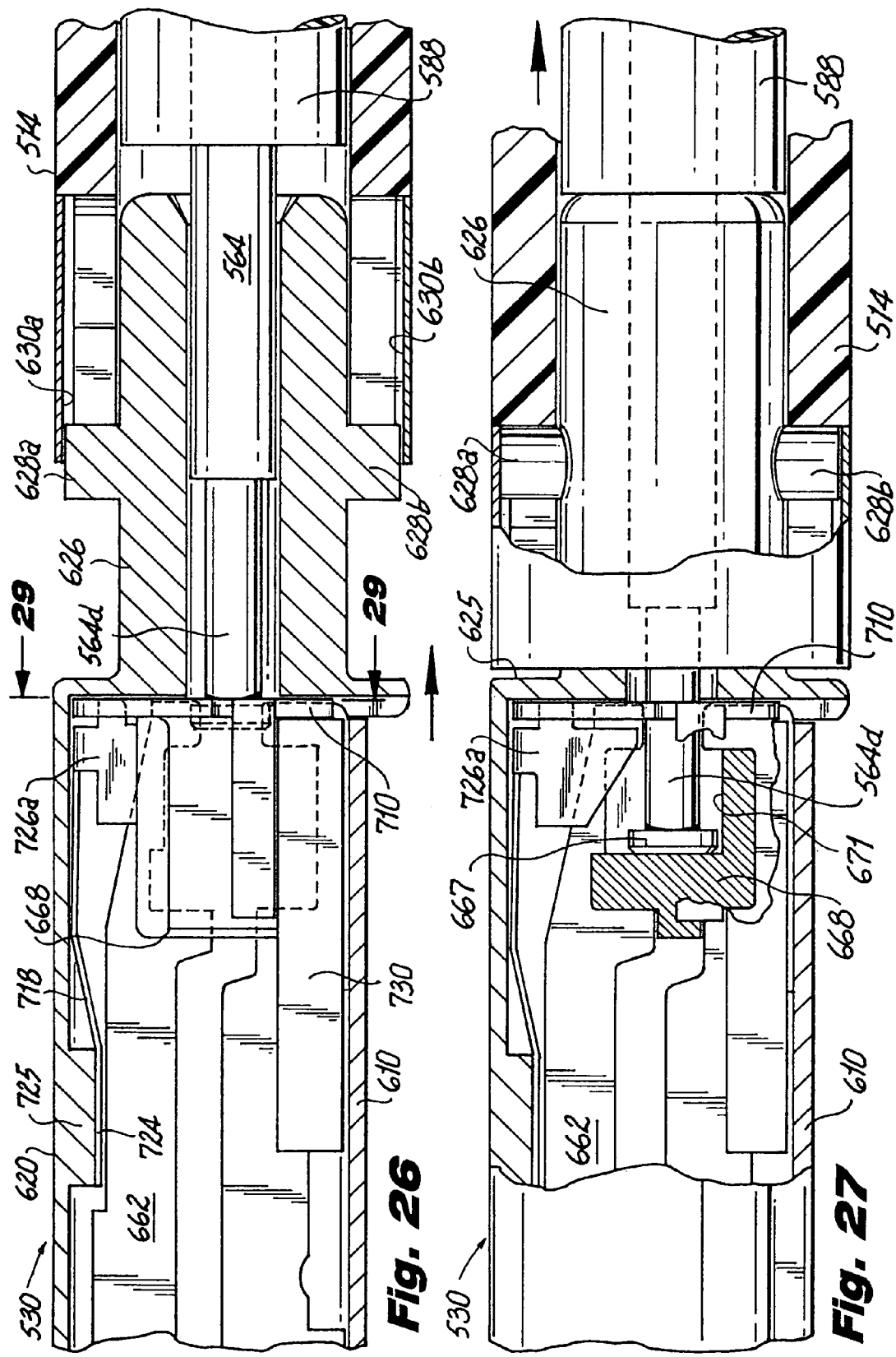

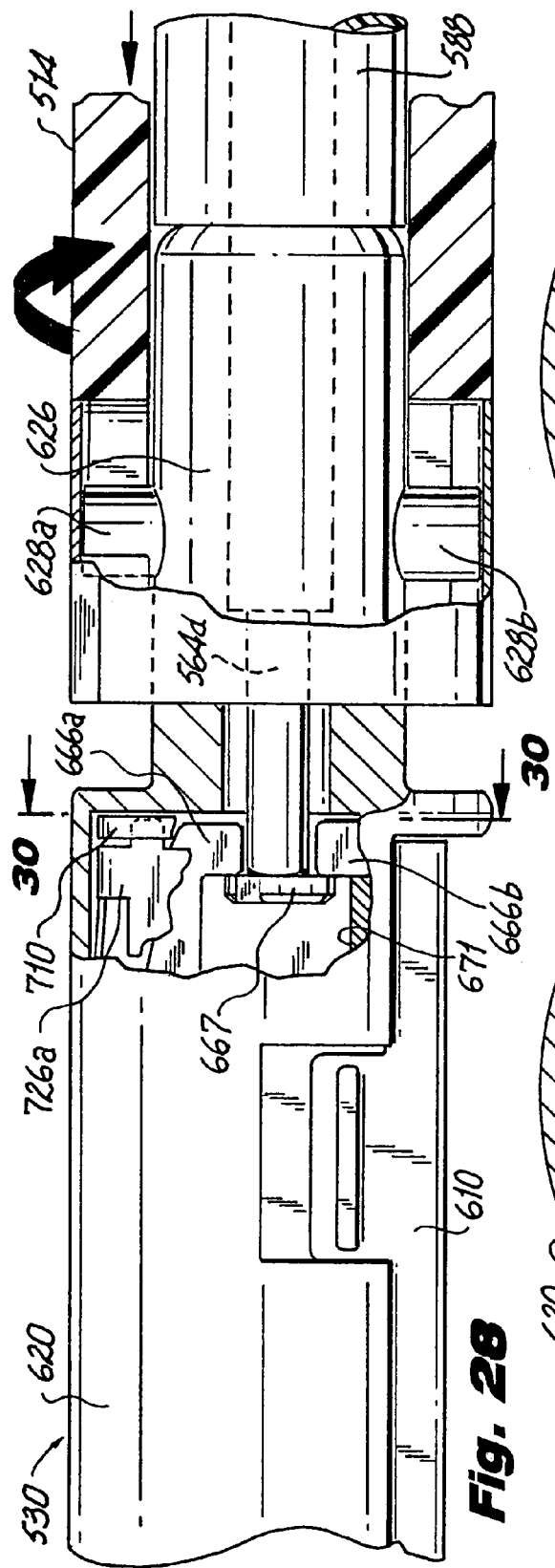
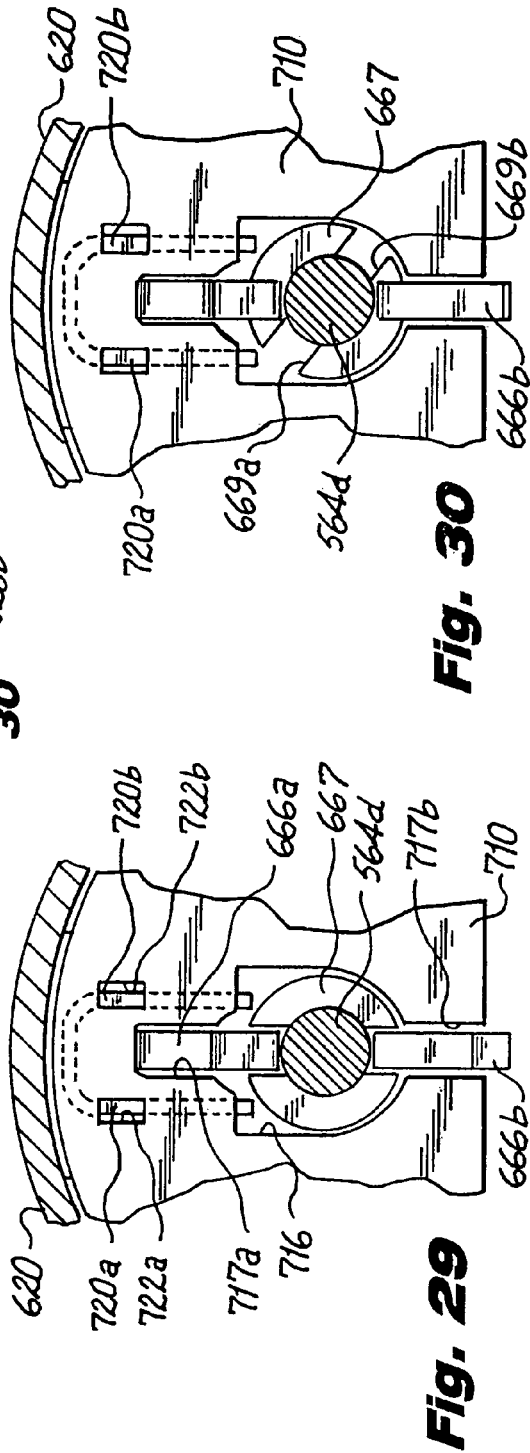
Fig. 28
Fig. 29
Fig. 30

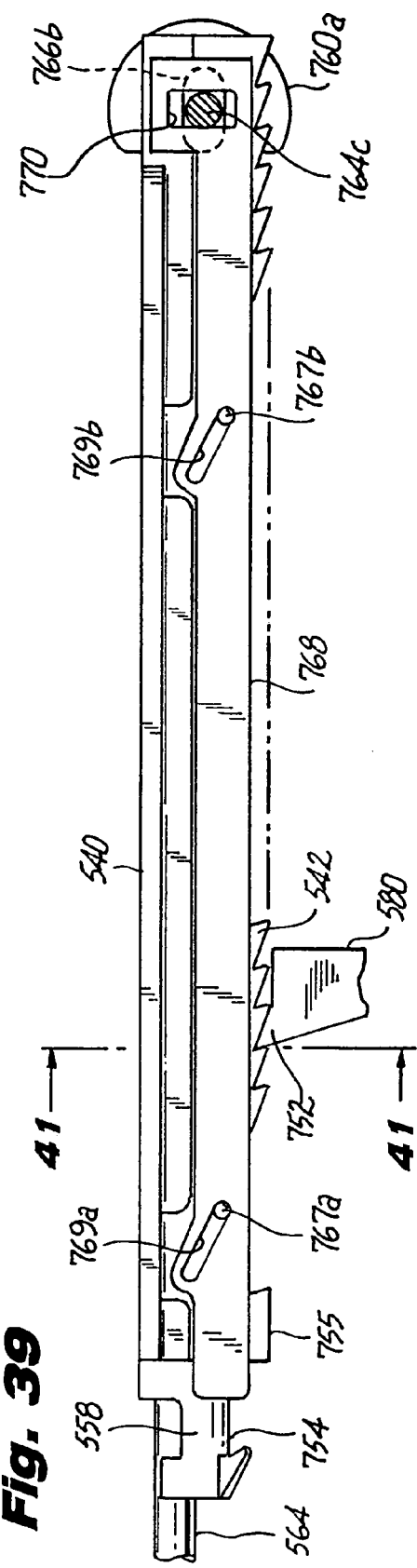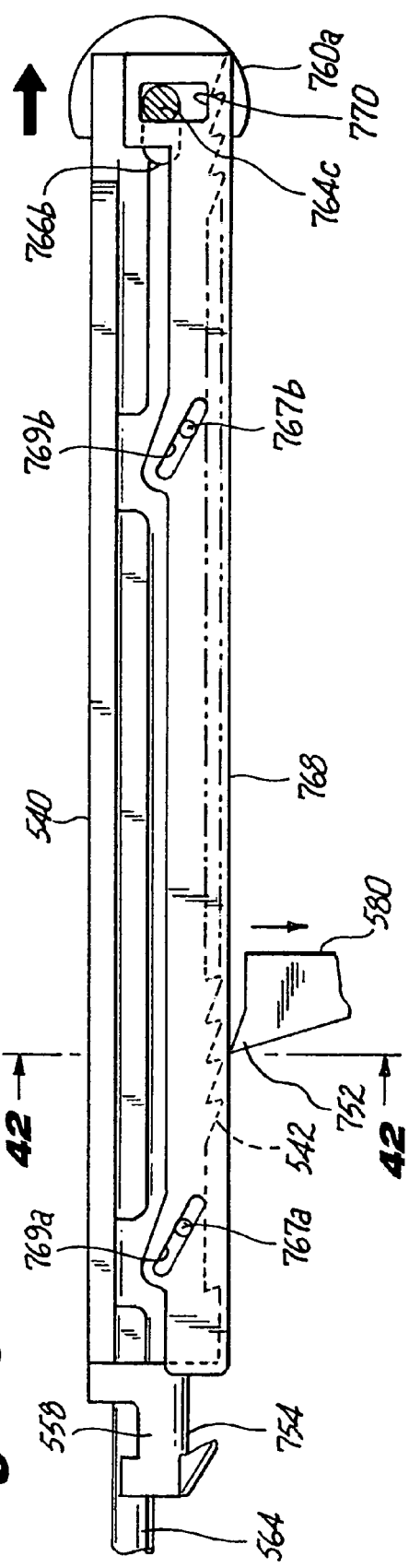

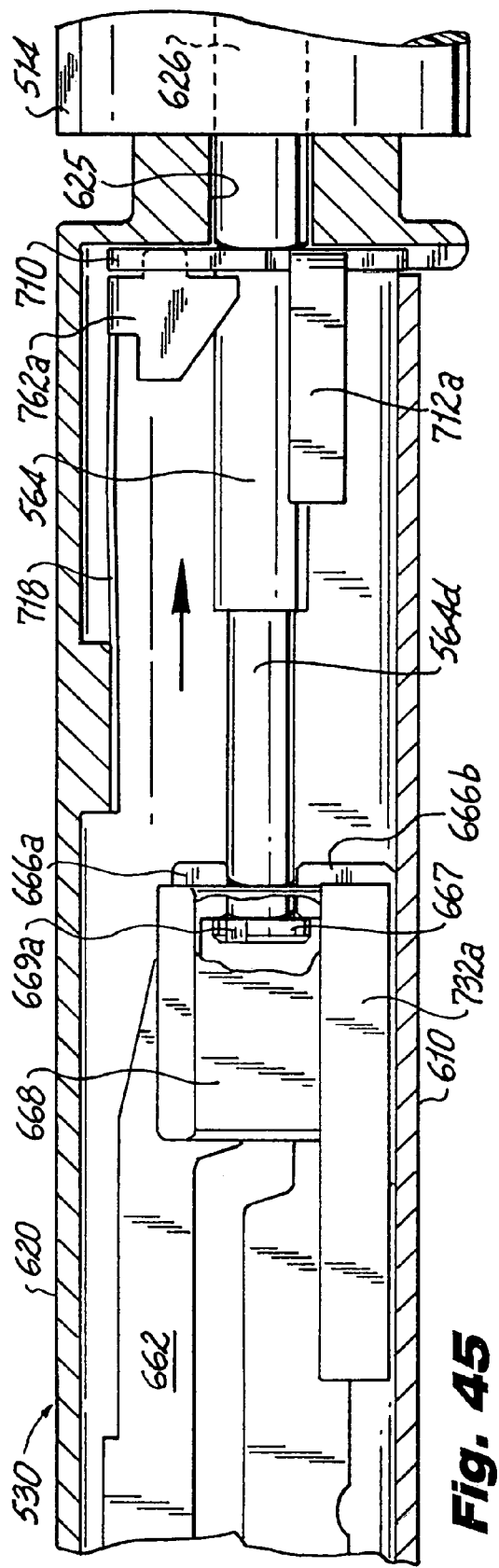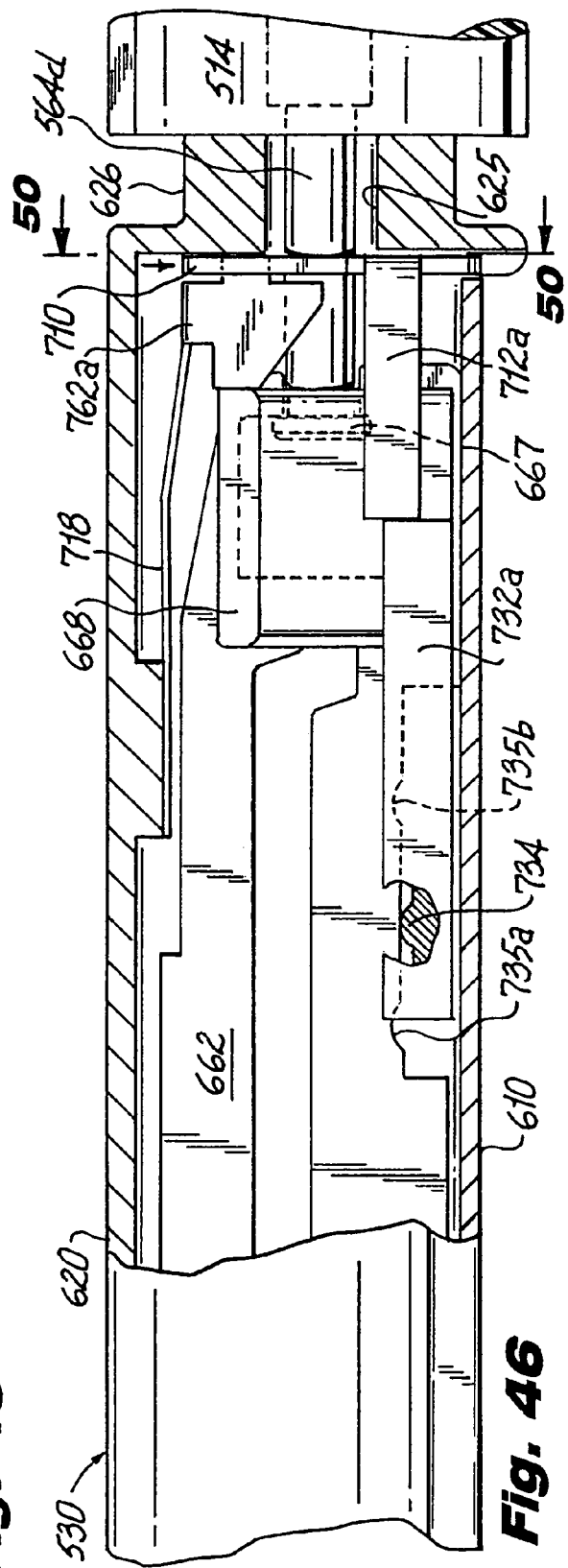

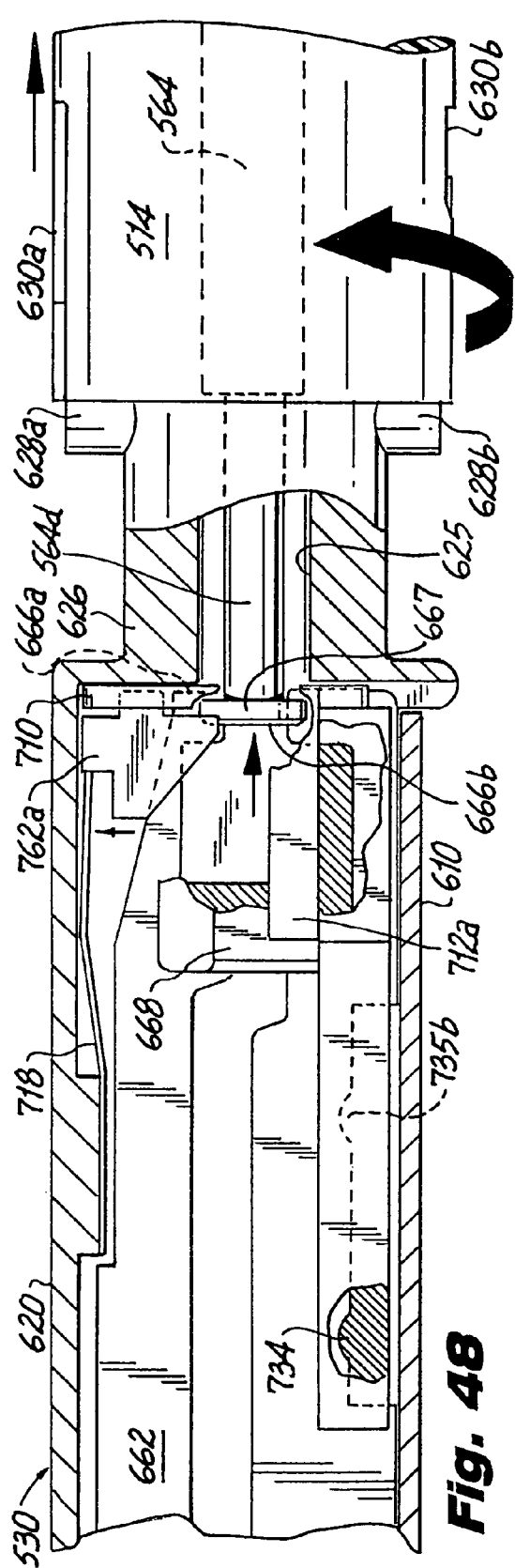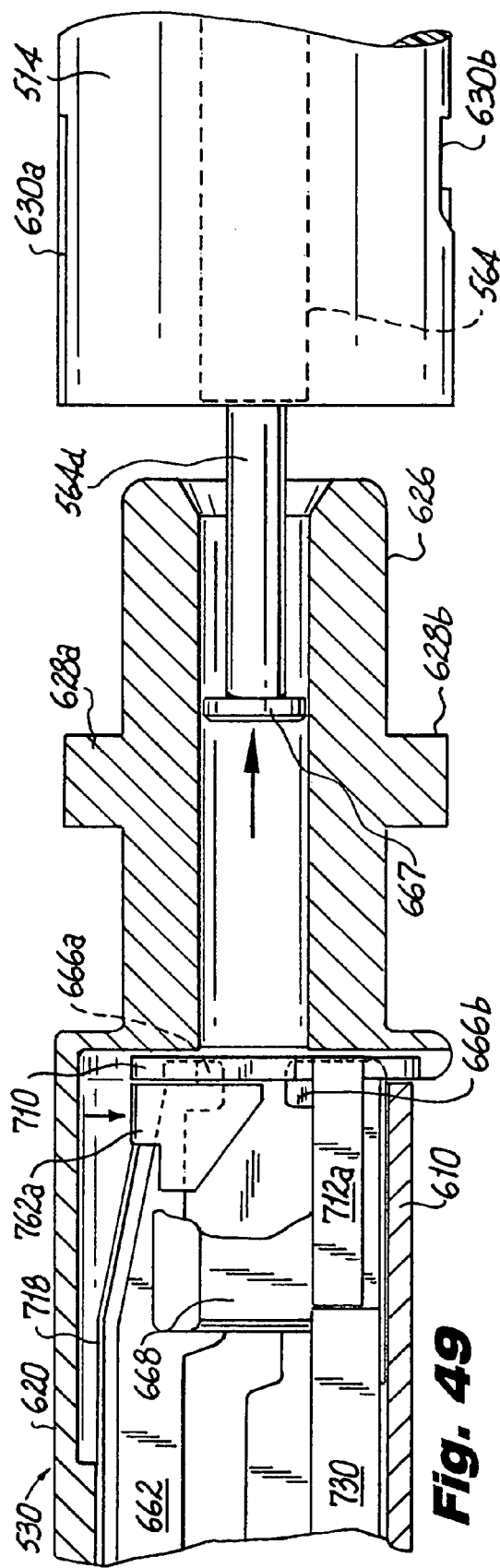

SURGICAL STAPLER

CROSS REFERENCE TO RELATED APPLICATIONS

This application is a divisional of U.S. patent application Ser. No. 11/186,743 filed Jul. 20, 2005, pending which is a continuation of U.S. application Ser. No. 11/011,355 filed Dec. 14, 2004, now U.S. Pat. No. 7,044,353 which is a continuation of Ser. No. 09/625,886 filed Jul. 26, 2000, now U.S. Pat. No. 6,986,451 which is a continuation of 09/497,647 filed Feb. 3, 2000, now abandoned which is a continuation of Ser. No. 09/119,543 filed Jul. 20, 1998, now U.S. Pat. No. 6,032,849 which is a continuation of Ser. No. 08/546,253 filed Oct. 20, 1995, now U.S. Pat. No. 5,782,396 which is a continuation-in-part of Ser. No. 08/520,202 filed on Aug. 28, 1995 now U.S. Pat. No. 5,762,256. Each of which is incorporated herein by reference in their entirety.

BACKGROUND

1. Technical Field

This application relates to a surgical stapling apparatus, and more particularly, to an apparatus for sequentially applying a plurality of surgical fasteners to body tissue and optionally incising the fastened tissue.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

U.S. Surgical, the assignee of the present application, has manufactured and marketed endoscopic stapling instruments, such as the Multifire ENDO GIA* 30 and Multifire ENDO GIA* 60 instruments, for several years. These instruments have provided significant clinical benefits. Nonetheless, improvements are possible, for example, by reducing the cost and complexity of manufacture.

Current laparoscopic linear stapling devices are configured to operate with disposable loading units (U.S. Surgical) and staple cartridges (Ethicon) of only one size. For example, individual linear staplers are presently available for applying parallel rows of staples measuring 30 mm, 45 mm and 60 mm in length. Thus, during a normal operation, a surgeon may be required to utilize several different stapling instruments to perform a single laparoscopic surgical procedure. Such practices increase the time, complexity and overall costs associated with laparoscopic surgical procedures. In addition, costs are greater in designing and manufacturing multiple stapler sizes, as opposed to creating a single, multipurpose stapler.

It would be extremely beneficial to provide a surgical device for use during laparoscopic and/or endoscopic surgical procedures that can be employed with several different sized disposable loading units to reduce the overall costs associated with such procedures. It would also be particularly beneficial if the device could perform multiple tasks, using disposable loading units of varying size and of varying purpose, such as, for example, to staple, clip and/or cut.

In making improvements or modifications to the current instruments, it would be highly desirable not to sacrifice any of the important benefits of the MULTIFIRE ENDO GIA* 30 and 60 instruments as compared to other commercially available products, e.g., the endoscopic stapling instruments manufactured and marketed by Ethicon, Inc. For example, any improvement should advantageously provide a fresh knife blade for each firing of the instrument and ensure that the disposable loading unit is securely retained in the stapling instrument unless and until the operating team chooses to remove it. These advantages have historically been found in the U.S. Surgical instruments, but not in the Ethicon instruments.

Therefore, a need exists for a reliable surgical stapler and disposable loading units for use therewith that exhibit all of the benefits of the present assignee's commercially available instruments while also reducing the cost and complexity of manufacture.

SUMMARY

The subject application is primarily directed to a stapling device for applying parallel rows of surgical fasteners to body tissue and, preferably, one that concomitantly forms an incision between the rows of staples during an endoscopic or laparoscopic surgical procedure. A particularly unique feature of the stapling device described herein is that it can be employed with a number of different disposable loading units. Moreover, the stapling device of the subject application can be utilized with disposable loading units configured to apply linear rows of staples measuring from about 15 mm in length to about 60 mm in length.

In a preferred embodiment of the subject surgical stapler, the device includes a handle assembly including an elongated barrel portion and an actuation handle movable through an actuating stroke, and an elongated body extending distally from the barrel portion of the handle assembly and defining a longitudinal axis. An elongated actuation shaft is supported at least in part within the barrel portion of the handle assembly and it has a particular linear dimension. The actuation handle interacts with the actuation shaft such that manipulation of the actuation handle through a complete actuating stroke causes the actuation shaft to translate through a predetermined linear distance.

A disposable loading unit is operatively engaged in a distal portion of the elongated body. The disposable loading unit preferably includes a carrier, a staple cartridge containing a plurality of staples, an actuator (movable through the housing and staple cartridge) and an anvil. The instrument actuation shaft drives the actuator through the staple cartridge to eject the staples against the anvil to form a staple line having a particular linear dimension. Preferably, the linear dimension of the staple line corresponds to the distance through which the actuation shaft translates in response to manipulation of the actuation handle through a particular number of complete or partial actuation strokes numbering more than one complete stroke.

The actuation shaft is preferably defined at least in part by a toothed rack having a particular rack length, and the actuation handle has a pawl member for selectively engaging the toothed rack and advancing the actuation shaft in response to manipulation of the actuation handle. When a disposable loading unit having linear rows of staples is used, the linear dimension of the staple line applied by the stapling unit is preferably proportional to the longitudinal travel of the actuation shaft. In a most preferred embodiment, the minimum linear dimension of the staple line will always be greater than the maximum linear distance through which the actuation shaft translates in response to a complete actuation stroke.

When a disposable loading unit having an anvil is used, the actuation handle is preferably movable through a clamping stroke in which the actuation shaft translates through a predetermined clamping distance to move the anvil from an open position to a closed position. The clamping stroke precedes the first of any number of complete or partial actuation strokes. In a preferred embodiment, an engagement hook is mounted within the barrel portion of the handle assembly to selectively maintain the actuation shaft in a particular position after traveling through the clamping distance and a notch is defined in a distal end portion of the actuation shaft, distal of the toothed rack, for receiving and releasably retaining the engagement hook.

In use of a preferred embodiment, movement of the actuation handle in a direction opposite the clamping stroke causes the engagement hook to release the actuation shaft, permitting the anvil to move to an open position. A lift finger is provided on a flange extending from the actuation handle and is positioned to move the engagement hook out of engagement with the notch when the actuation handle is moved in a direction opposite the clamping stroke. Preferably, a first biasing spring is provided within the handle assembly for biasing the actuation handle in a clockwise direction and a second biasing spring is provided within the handle assembly for biasing the actuation handle in a counter-clockwise direction, about a handle pivot point. The counter-clockwise direction corresponds to the direction of the clamping and actuating strokes.

The engagement hook is preferably configured to interact with the toothed rack to maintain the actuation shaft in a particular linear position during an actuation stroke, and it is normally biased into engagement with the actuation shaft. An abutment strut or beam is operatively associated with a proximal end portion of the stapler body for maintaining the engagement hook in a position out of engagement with the actuation shaft until a disposable loading unit is operatively engaged in a distal end portion of the elongated body. The abutment strut permits the engagement hook to engage the actuation shaft after a disposable loading unit has been operatively engaged in a distal end portion of the elongated instrument body.

In another preferred embodiment of the surgical stapling apparatus disclosed herein, a release mechanism is operatively associated with the handle assembly for effectuating the manual disengagement of the engagement hook from the actuation shaft to permit subsequent distal advancement of the actuation shaft in response to manipulation of the actuation handle through any number of subsequent stapling strokes. In addition, a retracting mechanism is operatively associated with the handle assembly for effectuating the manual retraction of the actuation shaft at any point in the actuating stroke so that the actuator can be withdrawn to permit the anvil to move from a closed position to an open position.

In a preferred embodiment of the device described herein, the disposable loading unit is a adapted to apply linear rows of staples and includes: a carrier having a proximal end portion including a coupling for releasable engagement in a distal end portion of the elongated instrument body; an elongate staple cartridge supported in the carrier and containing a plurality of surgical fasteners and a plurality of fastener pushers for ejecting the fasteners from the staple cartridge; an actuator for contacting the fastener pushers; and an anvil supported on the carrier and mounted for movement with respect to the staple cartridge between an open position and a closed position. The anvil preferably has a fastener forming surface against which the surgical fasteners are driven when ejected from the staple cartridge by the fastener pushers, and a camming surface opposite the fastener forming surface. The actuator is preferably wedged actuator that translates through the staple cartridge to sequentially interact with the fastener pushers to eject the fasteners from the staple cartridge.

The disposable loading unit further preferably includes an elongated drive beam having a proximal engagement portion, a distal working end portion having an abutment surface and a camming member. The proximal engagement portion is configured to mate with a distal end portion of the actuation assembly of the stapler while the abutment surface engages the actuator to eject staples from the staple cartridge during firing. The camming member contacts the camming surface of the anvil during firing. In use, the stapler actuation assembly moves the drive beam through the carrier causing the camming member to close the anvil or maintain the anvil closed as it substantially simultaneously causes the actuator to translate through the staple cartridge, thereby sequentially interacting with the plurality of fastener pushers to fire the staples.

Preferably, the camming member is defined by a cylindrical cam roller mounted on a flange extending from the distal working end portion of the drive beam. A longitudinal slot is defined in the anvil to accommodate the linear translation of the working end portion of the drive beam, and a transverse support flange is operatively mounted on the working end portion opposite the cam roller to engage an undersurface of the carrier as the cam roller engages the camming surface of the anvil. A longitudinal slot is also defined in the undersurface of the carrier to accommodate the linear translation of the working end portion of the drive beam. An optional anvil cover can be provided to ensure tissue is not inadvertently contacted by the drive beam or cam roller during firing.

Preferably, a knife blade is operatively supported adjacent a leading edge of the working end portion of the drive beam for forming an incision in stapled body tissue. Also, the actuator is preferably a sled including a planar base portion and a plurality of spaced apart upstanding cam wedges each having an inclined leading edge for interacting with the fastener pushers within the staple cartridge.

In a preferred embodiment of the stapling device described herein, the distal end portion of the elongated body and the proximal portion of the carrier includes cooperating portions of a bayonet-type coupling. The coupling facilitates the convenient removal and engagement of a variety of different sized disposable loading units including those which are configured to apply staple rows that are approximately 30 mm in length, 45 mm in length, and 60 mm in length. Accordingly, it is envisioned that the device can be sold and marketed as a kit which would include at least one surgical instrument designed to actuate compatible disposable loading units and a plurality of disposable loading units that can vary in size and type. The disposable loading units can be adapted to apply linear rows of staples, clips or other forms of fasteners. A common feature of these disposable loading units is that they utilize the longitudinal motion of the instrument actuation control rod to apply the fasteners.

These and other features of the surgical stapling device of the subject application will become more readily apparent to those skilled in the art from the following detailed description of the preferred embodiments of the device taken in conjunction with the drawings.

BRIEF DESCRIPTION OF THE DRAWINGS

Various embodiments of the surgical stapling apparatus of the subject application will be described hereinbelow with reference to the drawings wherein:

FIG. 12 is a side elevational view of the disposable loading unit of the subject application with the body thereof sectioned to illustrate the relative positions of the components prior to closing the anvil to clamp a tubular vessel;

FIG. 13 is a side elevational view of the disposable loading unit of the subject application with the body thereof sectioned to illustrate the relative positions of the components after the apparatus has been completely fired;

FIG. 15 illustrates an alternate embodiment of a disposable loading unit adapted to apply surgical clips;

FIG. 16 illustrates an alternate embodiment of a disposable loading unit adapted to apply single surgical staples;

FIG. 19 is an exploded perspective view of the body portion of the surgical stapling apparatus of FIG. 17 in conjunction with the elongated control rod which extends therethrough;

FIG. 20 is a perspective view of a distal portion of the control rod illustrated in FIG. 19;

FIG. 21 is a cross-sectional view taken along line 21—21 of FIG. 19 illustrating the proximal portion of the inner support tube housed within the body portion of the surgical stapling apparatus of FIG. 17;

FIG. 25 is an enlarged exploded perspective view of the lockout assembly illustrated in FIG. 24 with a distal portion of the control rod;

FIG. 26 is a side elevational view in partial cross-section of a proximal portion of the disposable loading unit of FIG. 24 as it is inserted into the distal end of the body portion with the lockout assembly disposed in a pre-actuated condition;

FIG. 27 is a side elevation view in partial cross-section of the proximal portion of the disposable loading unit of FIG. 24 when the mounting portion thereof is fully inserted into the distal end of the body portion;

FIG. 28 is a side elevational view in partial cross-section of the proximal portion of the disposable loading unit of FIG. 24 as it is rotated into an operational position;

FIG. 29 is a cross-sectional view taken along line 29—29 of FIG. 26 illustrating the alignment of the notches in the head of the control rod and the engagement fingers at the proximal end of the axial drive assembly;

FIG. 30 is a cross-sectional view taken along line 30—30 of FIG. 28 illustrating the position of the head of the control rod in relation to the engagement fingers after the disposable loading unit has been rotated into an operational position;

FIG. 39 is an enlarged side elevational view of the toothed rack and the release plate associated therewith illustrating the rack lock engaged in the toothed rack;

FIG. 40 is an enlarged side elevational view of the toothed rack and the release plate associated therewith illustrating the release plate moved to disengage the rack lock from the toothed rack;

FIG. 45 is a side elevational view in partial cross-section of the disposable loading unit of FIG. 24 with the components of the lockout assembly illustrated in a position corresponding to the control rod being withdrawn toward a post-fired proximal position;

FIG. 46 is a side elevational view in partial cross-section of the disposable loading unit of. FIG. 24 illustrating the orientation of the lockout assembly components as the control rod approaches its proximal-most position;

FIG. 48 is a side elevational view in partial cross-section of the disposable loading unit of FIG. 24 illustrating the orientation of the lockout assembly components when the loading unit has been moved distally with respect to the body portion to disengage the bayonet connection;

FIG. 49 is a side elevational view in partial cross-section of the disposable loading unit of FIG. 24 disengaged from the distal end of the body portion at the conclusion of a stapling procedure with the components of the lockout assembly illustrated in a blocking position to prevent subsequent utilization of the loading unit;

DETAILED DESCRIPTION OF PREFERRED EMBODIMENTS

Figure 1:
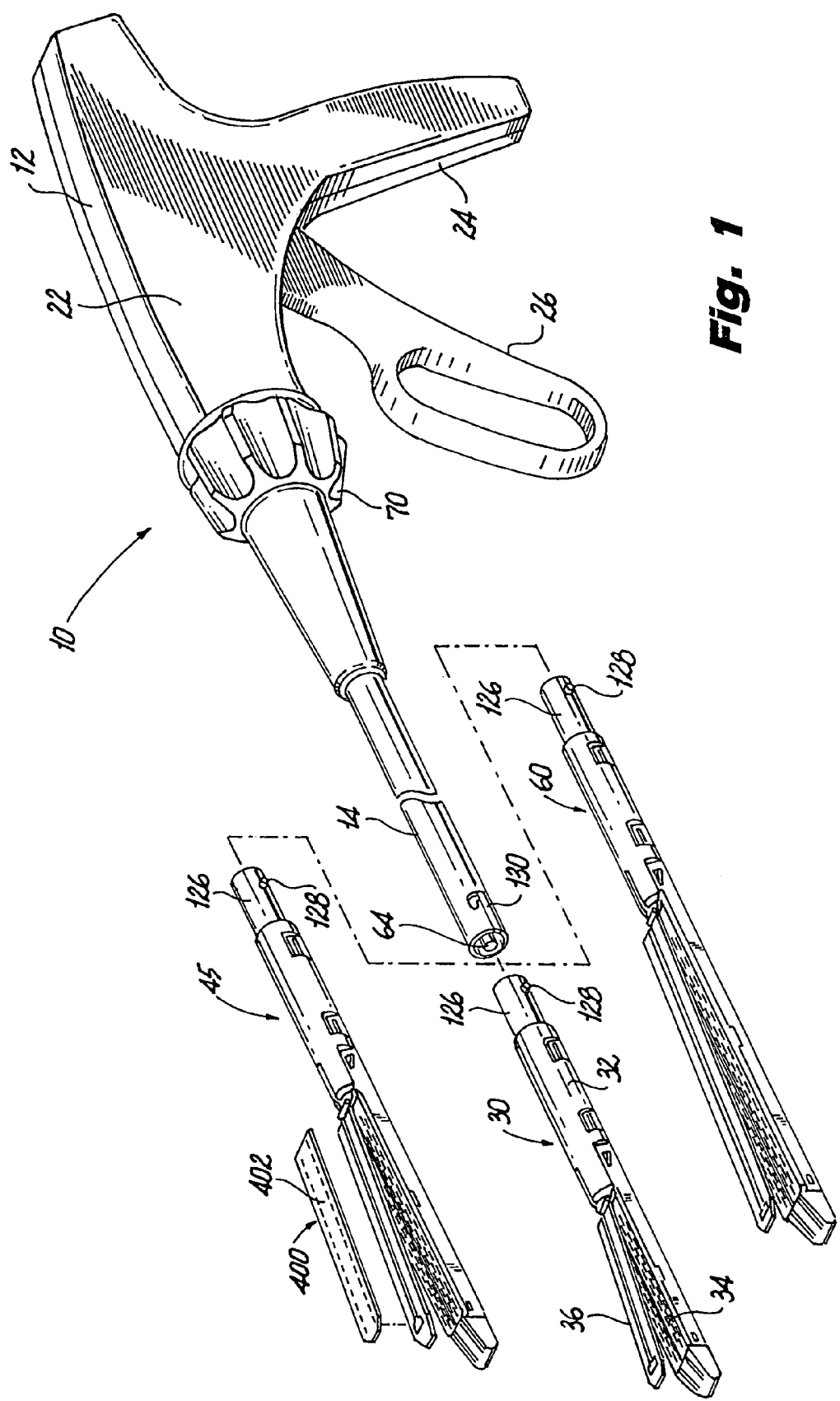
FIG. 1 is a perspective view of a surgical stapling apparatus constructed in accordance with a preferred embodiment of the subject application in conjunction with three different sized disposable loading units each configured for utilization with the stapling apparatus.

In the drawings and in the description which follows, the term "proximal", as is traditional, will refer to the end of the stapling apparatus which is closest to the operator, while the term "distal" will refer to the end of the apparatus which is furthest from the operator.

Referring now to the drawings wherein like reference numerals identify similar structural elements of the subject invention, there is illustrated in FIG. 1 a surgical apparatus constructed in accordance with a preferred embodiment of the subject application and designated generally by reference numeral 10. In brief, surgical apparatus 10 is a surgical stapling apparatus configured to engage body tissue, apply a plurality of surgical fasteners thereto, and form an incision in the fastened body tissue during a laparoscopic surgical procedure. Apparatus 10 can also be used to apply surgical clips and other fasteners (discussed in greater detail below) but will be primarily discussed in the context of applying parallel rows of staples from a staple cartridge disposed in a disposable loading unit.

Surgical apparatus 10 is unique among laparoscopic devices known in the art because it can employ a plurality of different sized disposable loading units. Moreover, apparatus 10 is preferably configured to operate with individual disposable loading units that apply linear rows of staples measuring 30 mm, 45 mm, or 60 mm in length (FIG. 1) or apply other types of fasteners (FIGS. 15 and 16). Thus, during a laparoscopic surgical procedure, a single instrument can be utilized with a plurality of interchangeable disposable loading units to perform several tasks. The preferred embodiments discussed in detail primarily relate to disposable loading units adapted to-apply linear rows of staples.

As illustrated in FIG. 1, surgical apparatus 10, has a handle assembly 12 and an elongated body 14. Apparatus 10 is adapted for use with disposable loading units 30, 45 and 60 each of which has a carrier 32, a staple cartridge 34, and an anvil 36 against which staples are driven when ejected from their housing. The following specification will provide a detailed description of the construction and operation of the apparatus and disposable loading units for use therewith.

Figure 2:
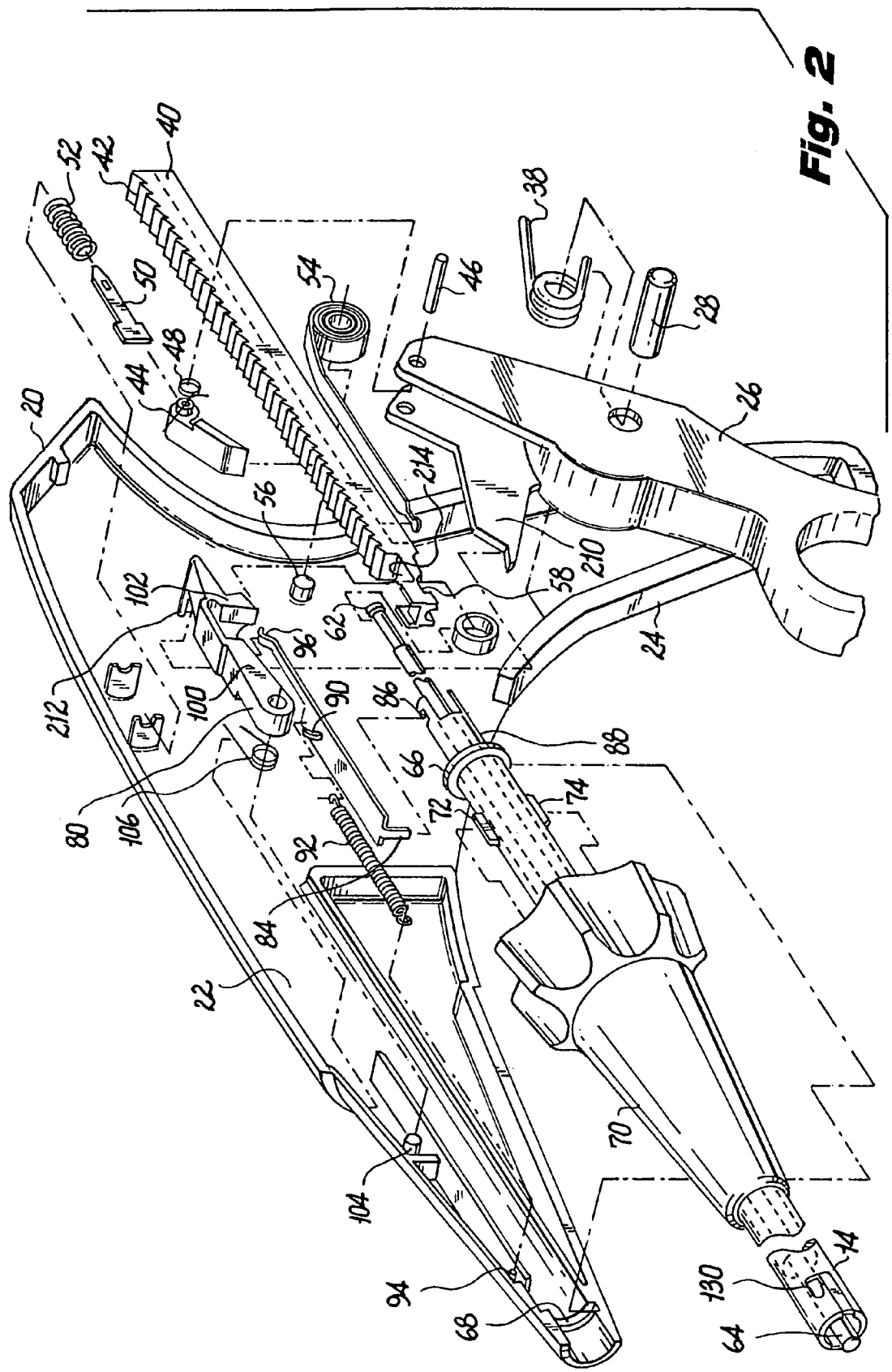
FIG. 2 is an exploded perspective view of the handle assembly of the surgical stapling apparatus illustrated in FIG. 1.

Referring to FIG. 2, handle assembly 12 includes a housing 20 defined by an elongated barrel portion 22, a stationary handle 24 depending from the barrel portion, and an actuation handle 26 which is pivotably mounted to the barrel portion and movable with respect to the stationary handle. Actuation handle 26 is supported within housing 20 by a pivot pin 28 and is biased against counter-clockwise movement by a coiled torsion spring 38.

Actuation handle 26 controls the linear movement of actuation shaft 40 which is mounted within barrel portion 22. More particularly, actuation shaft 40 has a toothed rack 42 defined thereon, and actuation handle 26 has a ratcheting pawl 44 mounted thereto for incrementally engaging and advancing actuation shaft 40. Pawl 44 is mounted on a pivot pin 46 and a coiled torsion spring 48 biases the pawl into engagement with toothed rack 42. A linear biasing strut 50 is supported within barrel portion 22 and is biased distally by a coiled compression spring 52 to bias the pawl, and hence the actuation handle, against clockwise rotation about pivot pin 28. Biasing strut 50 also serves to act on an angled rear cam surface on pawl 44 wherein contact of the cam surface with strut 50 causes pawl 44 to rotate clockwise (away from rack 42). When the instrument is at rest, pawl 44 is biased away from toothed rack 42. When actuation handle 26 is pulled proximally, pawl 44 moves away from strut 50 and rotates counterclockwise and engages the teeth of actuation shaft 40, thereby allowing actuation handle 26 to drive the shaft distally.

Actuation shaft 40 is normally biased in a proximal direction within barrel portion 22 by a constant force spring 54 which is mounted to the actuation shaft adjacent the distal end thereof by conventional fastening means known in the art. Constant force spring 54 is supported on a boss 56 provided within the housing 22 of handle assembly 12. The distal end portion of actuation shaft 40 has a cavity 58 defined in an undersurface thereof for engaging and retaining the flanged proximal end 62 of control rod 64. Control rod 64 extends coaxially through the elongated body 14 of surgical stapler 10 to interact with a disposable loading unit at a distal end thereof. Thus, linear advancement of actuation shaft 40 in response to manipulation of actuation handle 26 causes corresponding longitudinal movement of control rod 64, and, as will be discussed in detail hereinbelow, actuation of an associated disposable loading unit.

With continuing reference to FIG. 2, the proximal end portion of the elongated body 14 of surgical stapler 10 has an annular flange 66 formed thereon which engages a corresponding annular recess 68 formed within the barrel portion 22 adjacent the distal end thereof to fixedly attach the two structural members. The engagement of flange 66 within recess 68 facilitates rotational movement of body portion 14 with respect to the barrel portion 22 about a longitudinal axis which extends therethrough. A collar 70 is fixedly mounted to the proximal portion of stapler body 14 by a pair of opposed protuberances 72 and 74. Thus, rotation of collar 70 will cause corresponding rotation of body portion 14 to increase the range of operability of surgical stapler 10.

Within handle assembly 12, there is also contained a mechanism for initiating the engagement between a rack lock 80 and the toothed rack 42 of actuation shaft 40. Rack lock 80 maintains the longitudinal position of actuation shaft 40 under the bias of constant force spring 54. Rack lock 80 will not engage the rack unless and until a disposable loading unit is operatively engaged in the distal end portion of portion body 14. This mechanism is illustrated in FIG. 2 and its interaction with rack lock 80 is best understood by also referring to FIGS. 4 and 5. The mechanism includes an elongate beam or strut 82 having a distal tang 84 that engages a keeper notch 86 formed adjacent the proximal end of a support tube 88 that is slidably mounted within stapler body 14. Beam 82 has a medial hook 90 for engaging the proximal end of a coiled biasing spring 92, the distal end of which is mounted on a boss 94 provided within barrel portion 22. Biasing spring 92 biases beam 82, and hence support tube 88, against proximal movement. An arcuate cam finger 96 projects proximally from beam 82 for interacting with an angled cam surface 98 defined on the undersurface of the body 100 of rack lock 80. Rack lock 80 further includes a wedged clasp portion 102 which is dimensioned and configured to engage the teeth of the toothed rack 42 to maintain the longitudinal position of actuation shaft 40 during the operation of instrument 10. The body 100 of rack lock 80 is mounted on a boss 104 provided within the barrel portion 22 of housing 20. A coiled torsion spring 106 is also mounted on boss 104 and is connected to body 100 to bias the rack lock into engagement with toothed rack 42.

Figure 4:
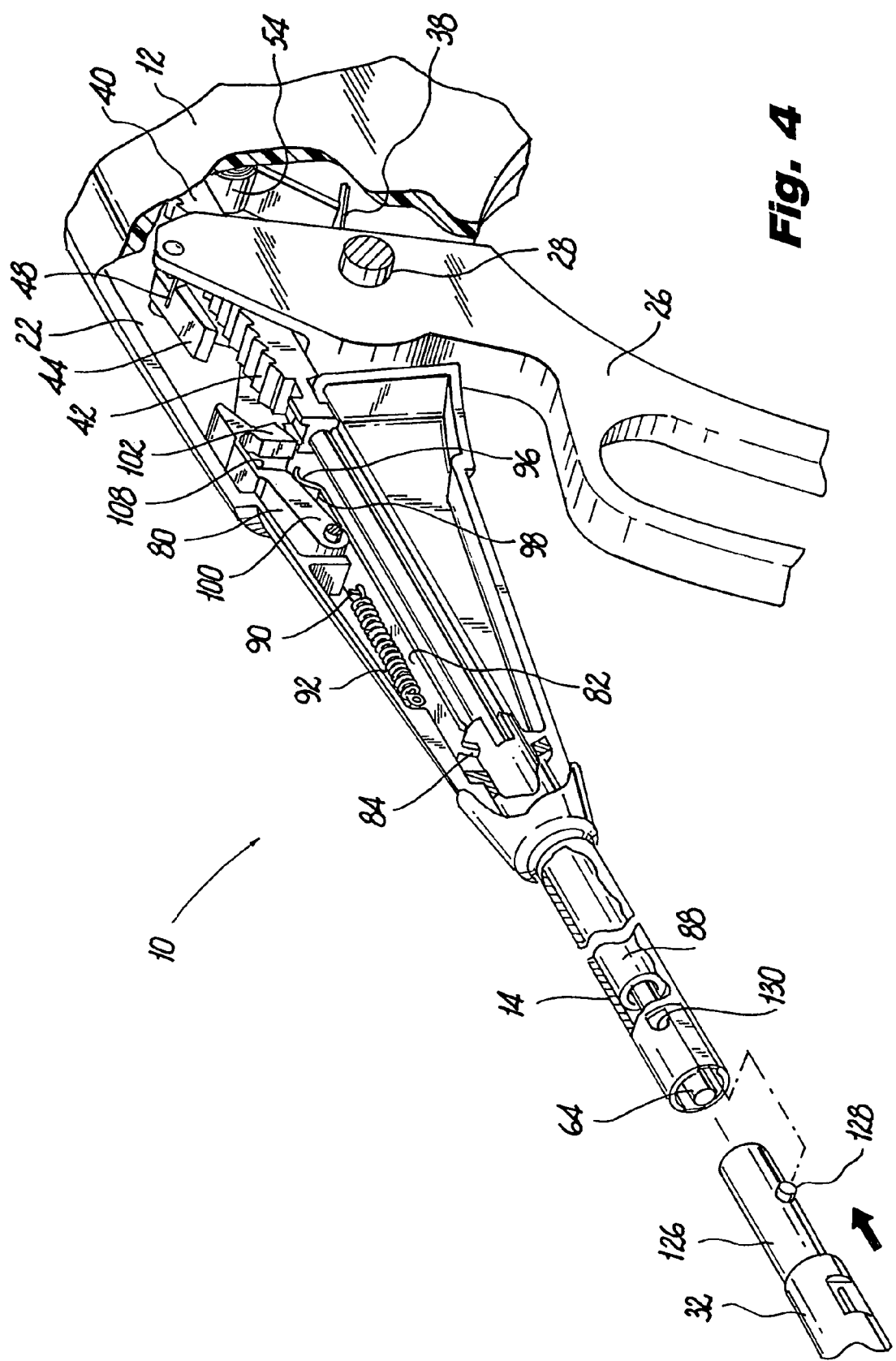
FIG. 4 is a perspective view in partial cross-section of the handle assembly and body portion of the stapling apparatus illustrated in FIG. 1 as the disposable loading unit of FIG. 3 is inserted into the distal end of the body.
Figure 5:
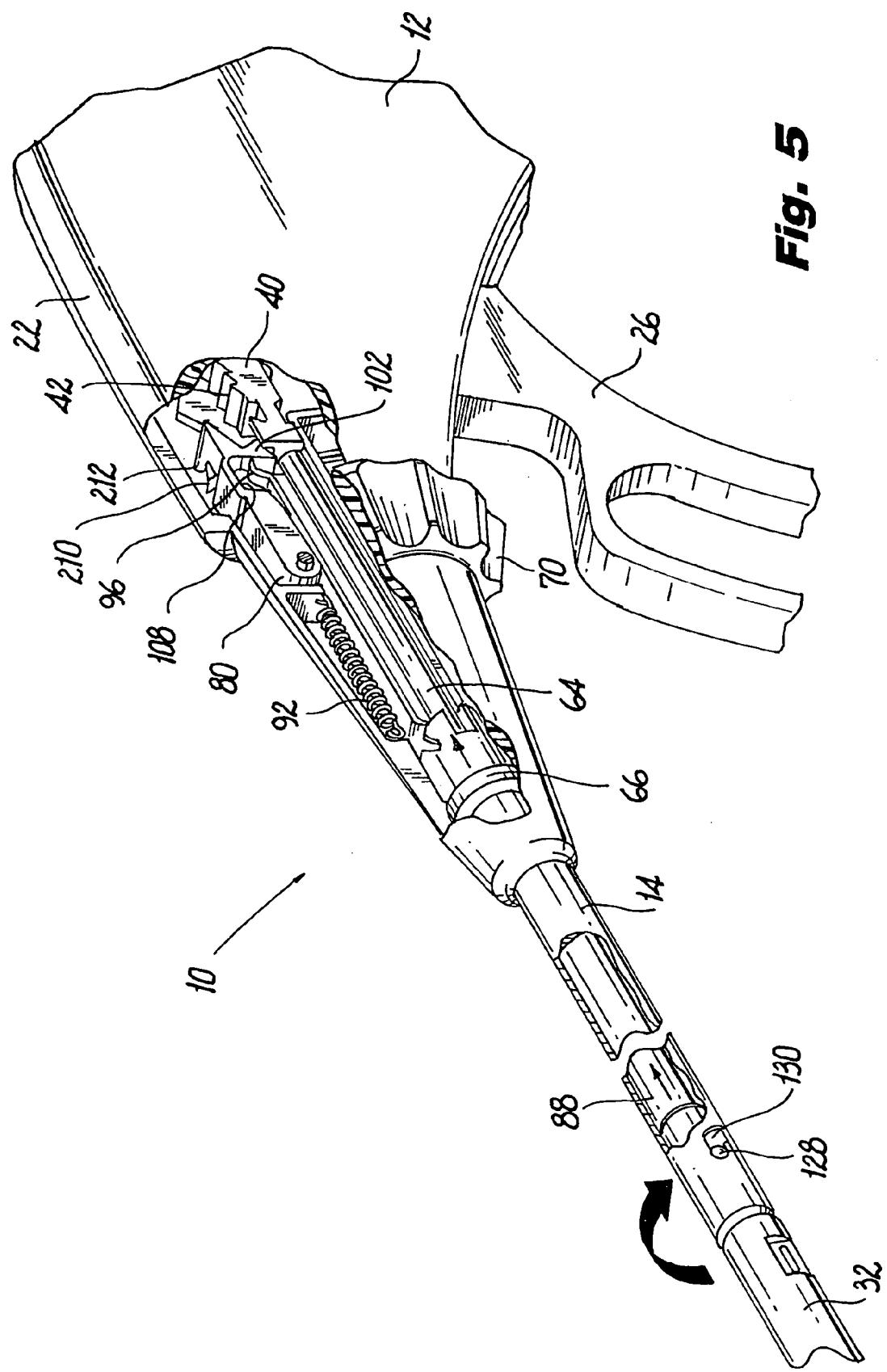
FIG. 5 is a perspective view which corresponds to the illustration in FIG. 4 with the disposable loading unit mounted in the body of the stapling apparatus and the actuation mechanism within the handle portion enabled as a result of the insertion of the disposable loading unit.

As best seen in FIGS. 4 and 5, when the proximal end portion of the carrier 32 of disposable loading unit 30 is inserted into the distal end of elongated body 14, support tube 88 is urged in a proximal direction against the bias of spring 92. Thereupon, beam 82 translates proximally and the arcuate cam finger 96 contacts angled cam surface 98, lifting rack lock 80 and causing it to rotate in a counter-clockwise direction against the bias of torsion spring 106. At such a time, the cam finger 96 of beam 82 is accommodated within a recess 108 formed in the body 100 of rack lock 80. With the rack lock in this position, it will engage actuation shaft 40 when it is advanced distally upon manipulation of actuation handle 26. The interaction of rack lock 80 and actuation shaft 40 will be discussed in greater detail hereinbelow with respect to the manner in which instrument 10 is operated to clamp body tissue and apply fasteners thereto.

Figure 3:
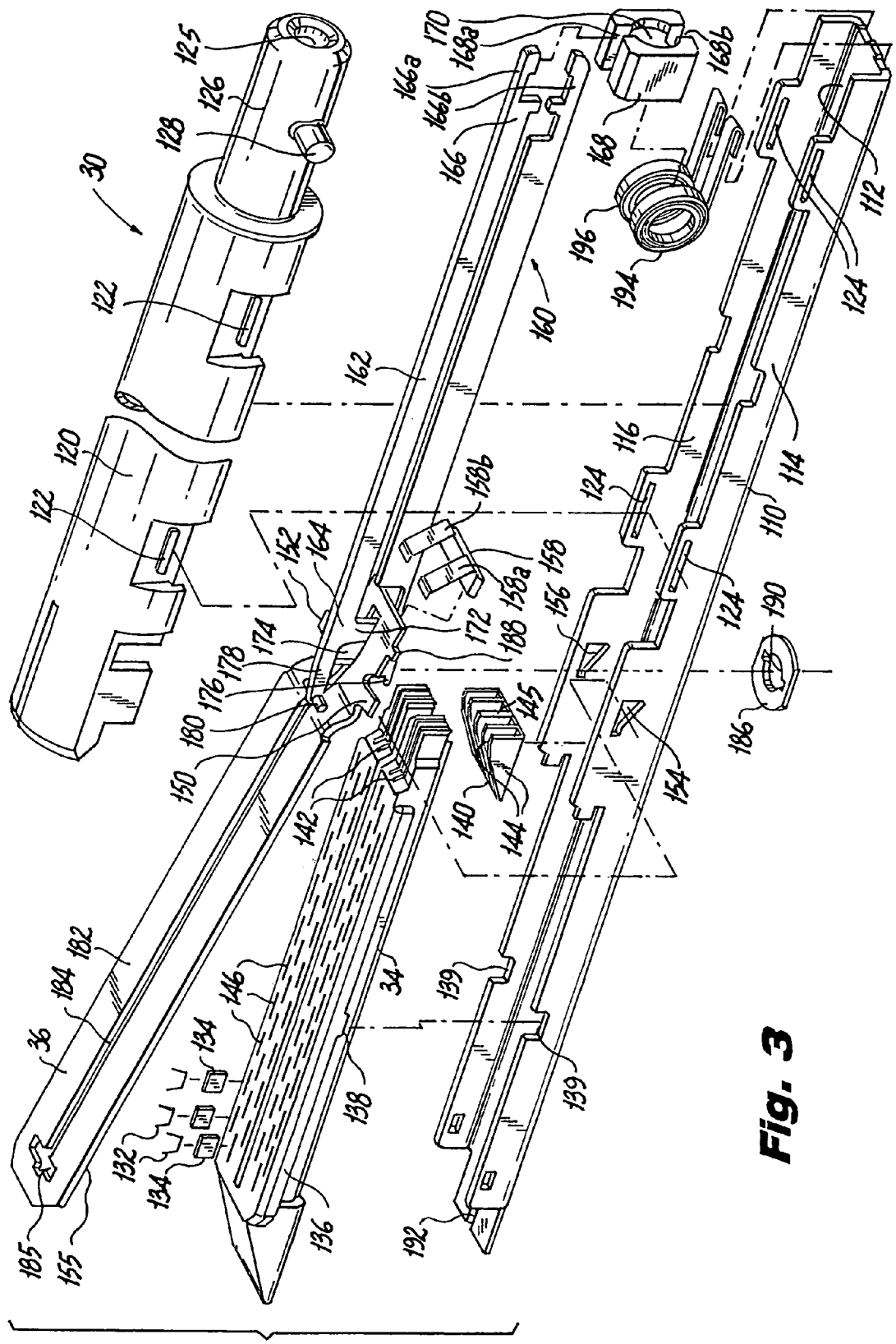
FIG. 3 is an exploded perspective view of a disposable loading unit constructed in accordance with a preferred embodiment of the subject application.

Referring now to FIG. 3, an exemplary disposable loading unit is illustrated and is designated generally by reference numeral 30. As noted hereinabove, disposable loading unit 30, which is particularly adapted to apply a plurality of linear rows of staples measuring about 30 mm in length, is one of several different size or type of disposable loading units that can be utilized with instrument 10 during a surgical procedure. The carrier 32 of stapling unit 30 includes an elongate channel 110 having a base 112 and two parallel upstanding walls 114 and 116 which include several mounting structures for supporting staple cartridge 34 and anvil 36. Carrier 32 also includes mounting portion 120 which is mounted to the proximal portion of channel 110 through the engagement of a plurality of spaced apart rectangular tangs 122 and a plurality of corresponding slots 124 formed in the opposed walls 114 and 116 of channel 110. The proximal end section 126 of mounting portion 120 is dimensioned and configured for insertion into the distal end portion of elongated body 14, and it is provided with an axial bore 125 for accommodating the distal end of control rod 64.

A coupling stem 128 projects radially outwardly from end section 126 for interacting with the J-shaped coupling slot 130 defined in the wall of the distal end portion of elongated body 14 (see FIGS. 4 and 5). Stem 128 and slot 130 together define a conventional bayonet-type coupling which facilitates quick and easy engagement and removal of the stapling unit from the stapler during a surgical procedure. Once engaged in the distal end portion of stapler elongated 14, the distal end-of support tube 88 urges proximal end section 126 distally under the bias of coiled spring 92, thereby maintaining the coupling stem 128 within coupling slot 130.

With continuing reference to FIG. 3, the distal portion of channel 110 supports staple cartridge 34 which contains a plurality of surgical fasteners 132 and a plurality of corresponding ejectors or pushers 134 that drive the fasteners from cartridge 34 under the influence of a fastener driving force exerted by actuation sled 140. Staple cartridge 34 is maintained within channel 110 by lateral struts 136 which frictionally engage the upper surfaces of channel walls 114 and 116, and the frictional engagement of housing tabs, such as tab 138, within notches 139. These structures serve to restrict lateral, longitudinal, and elevational movement of the staple cartridge 34 within channel 110.

Figure 14:
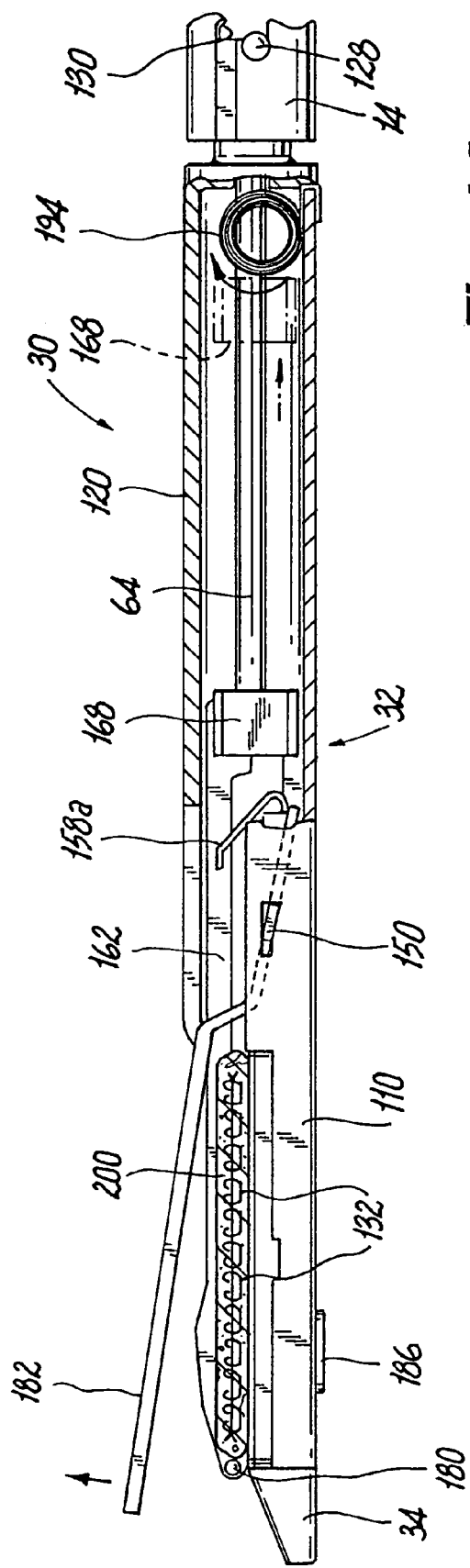
FIG. 14 is a side elevational view of the disposable loading unit as illustrated in FIG. 13 with the anvil moved to an open position under the bias of a release spring.

A plurality of spaced apart longitudinal slots 142 extend through staple cartridge 34 to accommodate the upstanding cam wedges 144 of actuation sled 140. Slots 142 communicate with a plurality of transverse retention slots 146 within which the plurality of fasteners 132 and pushers 134 are respectively supported. During operation, as actuation sled 140 translates through staple cartridge 34, the angled leading edges of cam wedges 144 sequentially contact pushers 136, causing the pushers to translate vertically within slots 146, urging the fasteners 134 therefrom. The result of the interaction between actuation sled 140 and pushers 136 is illustrated in FIGS. 12–14, and will be described hereinbelow with reference thereto. See also, commonly assigned U.S. Pat. No. 4,978,049 to Green, the disclosure of which is herein incorporated by reference in its entirety.

With continuing reference to FIG. 3, the anvil 36 of disposable loading unit 30 is provided with opposed mounting wings 150 and 152 which are dimensioned and configured to engage pivot apertures 154 and 156 in channel walls 114 and 116, respectively. A biasing member 158 having spring arms 158a and 158b is secured to the proximal end of anvil 36. The spring arms bear against internal bearing surfaces defined within mounting portion 120 to bias anvil 36 into a normally open position wherein the interior fastener forming surface 155 thereof is spaced from staple cartridge 34.

Disposable loading unit 30 further includes an axial drive assembly 160 for transmitting the longitudinal drive forces exerted by control rod 64 to actuation sled 140 during a stapling procedure. Drive assembly 160 includes an elongated drive beam 162 including a distal working head 164 and a proximal engagement section 166. Engagement section 166 includes a pair of engagement fingers 166a and 166b which are dimensioned and configured to mountingly engage a pair of corresponding retention slots 168a and 168b formed in a drive block 168. Drive block 168 has a proximal porthole 170 for receiving the distal end of control rod 64 when the proximal end of stapling unit 30 is inserted into the distal end of stapler body 14. Drive block 168 can be provided with an internal slot to receive a stem (not shown) from a distal end of control rod 64 to form a bayonet type connection, similar to that shown in connecting elongated body 14 to coupling stem 128. Such a connection would enable the user to manipulate drive beam 162 upon movement of control rod 64. The working end 164 of drive beam 162 is defined by a vertical support strut 172 which supports a knife blade 174, and an abutment surface 176 which engages the central support wedge 145 of actuation sled 140. Knife blade 174 travels slightly behind actuation sled 140 during a stapling procedure to form an incision between the rows of staple body tissue. A retention flange 178 projects distally from vertical strut 172 to retain a cylindrical cam roller 180. Cam roller 180 is dimensioned and configured to engage and translate with respect to the exterior camming surface 182 of anvil 36 to progressively clamp the anvil against body tissue during firing.

A longitudinal slot 184 extends through anvil 36 to accommodate the translation of retention flange 178 and vertical strut 172. A balancing flange 186 is secured to the working end of drive beam 162 through the engagement of retention foot 188 within a complementary retention port 190 formed in flange 186. Flange 186 serves to balance the clamping forces generated by cam roller 180 as anvil 36 is progressively clamped. A longitudinal slot 192 is formed in the base 112 of channel 110 to accommodate the longitudinal translation of retention foot 188 during firing.

With reference to disposable loading unit 45 in FIG. 1, an anvil cover is provided to protect tissue from moving parts along the exterior of anvil 36. In particular, anvil cover 400 has channel 402 formed on an underside thereof and is secured to an upper surface of anvil 36 to form a channel therebetween. Cam roller 180 travels in channel 402 between cover 400 and anvil 36 during firing. Anvil cover 400 is preferably plastic, but can be fabricated from any suitable biocompatible material.

Returning to FIG. 3, dual constant force spring members 194 and 196 are connected to the proximal end of channel base 112 and are disposed distal of drive block 168 to bias the block against distal movement. As best seen in FIGS. 12–14, when drive block 168 translates distally, spring members 194 and 196 unwind until they are passed over by the block at the end of its travel. At such a time, the spring members return to their normally wound position providing a buffer for the mounting block. Thus, an attempt to return the block to the proximal most position after firing the disposable loading unit will be inhibited.

Referring now in sequential order to FIGS. 4–11, to initiate the operation of instrument 10, a desired disposable loading unit is selected. Such disposable loading unit can be one of the different sized disposable loading units illustrated in FIG. 1 or one of the disposable loading units adapted to apply surgical clips (FIG. 15) or other types of surgical staples (FIG. 16). Use of the instrument will be discussed herein using a disposable loading unit adapted to apply linear rows of staples. Disposable loading unit 30, is mounted to the stapler by inserting the proximal mounting section thereof into the distal end of the elongated body 14, as shown in FIG. 4. Prior to insertion, support tube 88 is in its distal-most position within elongated body 14 and it is maintained in that position by spring 92. Accordingly, the cam finger 96 of beam 82 maintains rack lock 80 in a disengaged uplifted position, spaced from the toothed rack 42 of actuation shaft 40.

Once the proximal end of the disposable loading unit is inserted into the distal end of elongated body 14, it is rotated approximately 10° to 15° to position coupling stem 128 in the base of coupling slot 130. Thereupon, the bias of spring 92 urges support tube 88 distally to lock stem 128 within the base of slot 130. If a coupling system is provided between control rod 64 and drive block 168 (discussed above) such rotation would couple these member as well. In addition, as illustrated in FIG. 5, when support tube 88 is shifted proximally by the insertion of the proximal section 126 of mounting portion 120 into elongated body 14, arcuate cam finger 96 of beam 82 translates proximally against cam surface 98 until it reaches recess 108. Thereupon rack lock 80 moves into an engagement position under the bias of torsion spring 106, and instrument 10 is ready for use.

Figure 6:
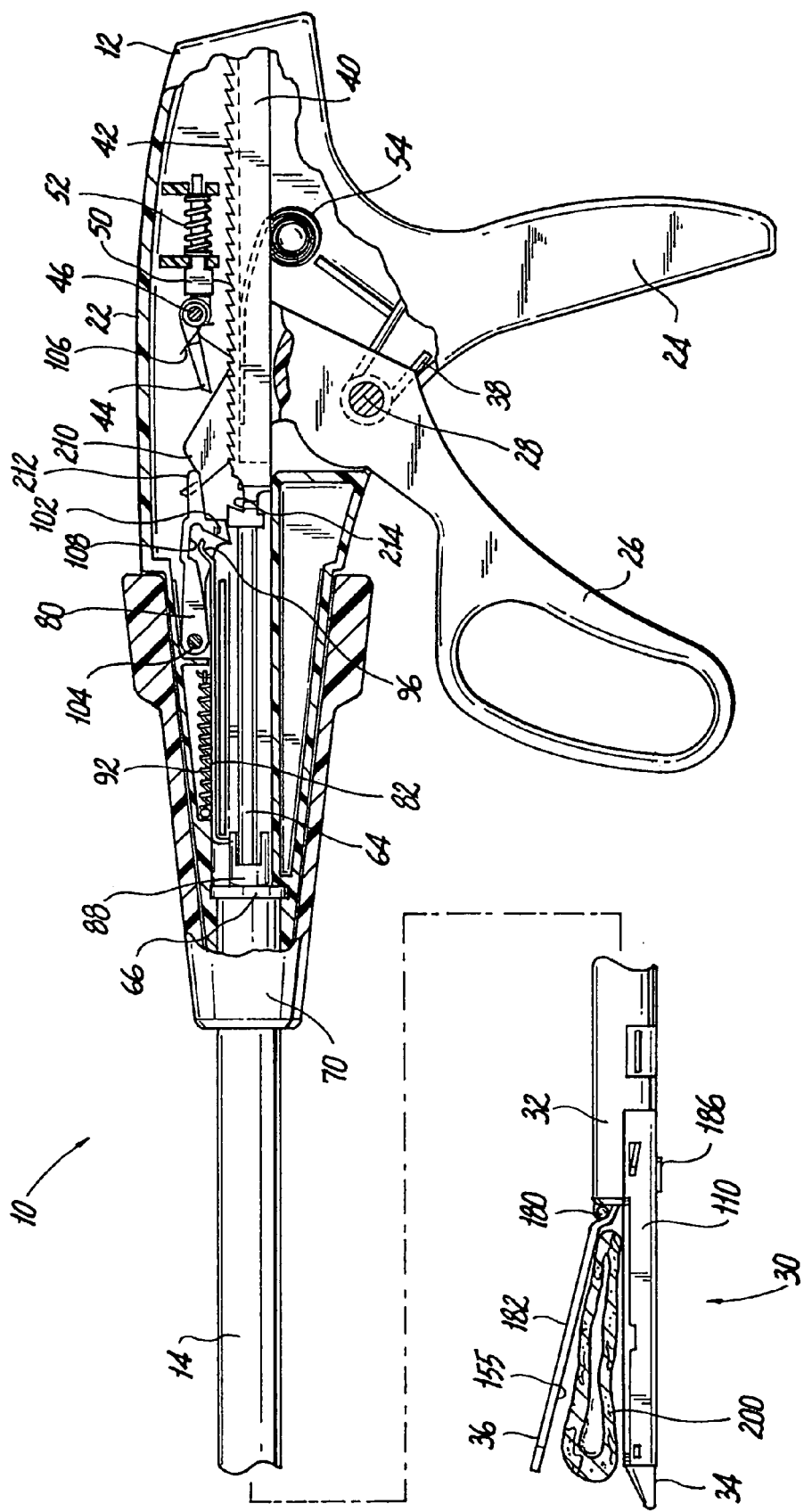
FIG. 6 is a side elevational view of the surgical stapling apparatus of the subject application with the handle portion sectioned to illustrate the relative positions of the components of the actuation assembly housed therein prior to actuation.

Turning to FIG. 6, prior to utilization, actuation handle 26 is in the illustrated neutral position. In this position, pawl 44 is spaced from the toothed rack 42 of actuation shaft 40. In addition, lift arm 210 which projects distally from actuation handle 26 is engaged beneath a transverse finger 212 formed at the proximal end of rack lock 80 adjacent the wedged clasp portion 102. Lift arm 210 serves to disengage clasp portion 102 from actuation shaft 40 under certain operating conditions which will be discussed hereinbelow with respect to FIGS. 8 and 9.

Prior to manipulating actuation handle 26, actuation shaft 40 is in its proximal-most position, as is control rod 64, biased against distal movement by constant force spring 54. Accordingly, anvil 36 is in an open position biased against closure by spring arms 158a and 158b. Thus, at such a time, body tissue such as tubular vessel 200 may be captured between the fastener forming surface of anvil 36 and the tissue contacting surface of staple cartridge 34.

Figure 7:
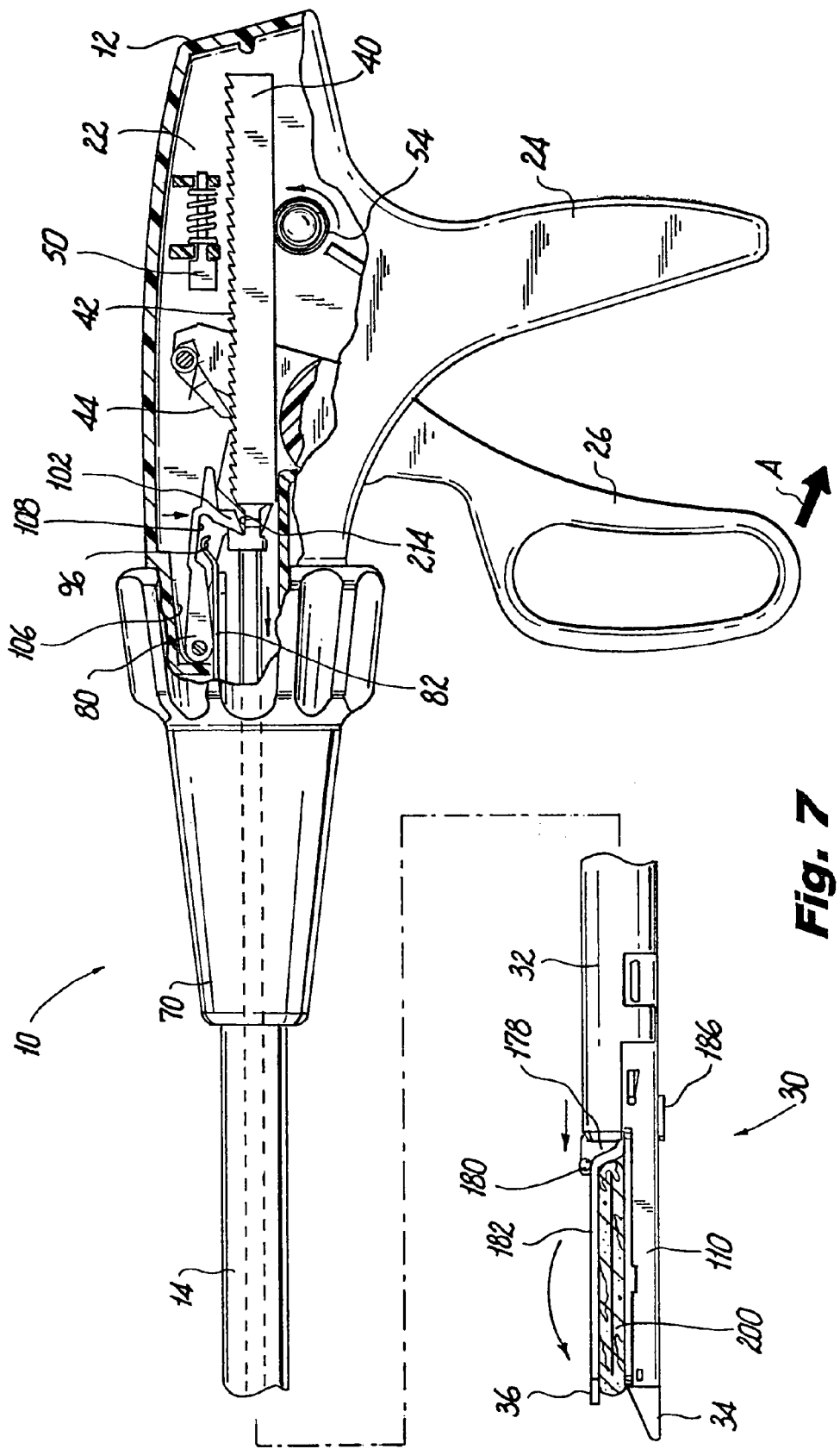
FIGS. 7 is a side elevational view of the surgical stapling apparatus of the subject application with the handle portion sectioned to illustrate the relative positions of the components of the actuation assembly when the actuation handle is partially compressed to move the anvil of the disposable loading unit to a closed position.

Turning now to FIG. 7, manipulation of actuation handle 26 in the direction indicated by reference arrow "A" causes pawl 44 move distally and rotate counterclockwise to engage toothed rack 42 and drive actuation shaft 40 distally against the bias of spring 54. As a result, control rod 64 is driven distally, forcing drive block 168 forward within disposable loading unit 30. Accordingly, a working end 164 of drive beam 162 translates distally and cam roller 180 engages the proximal end portion of the cam surface of anvil 36, causing the anvil to move into a closed position, clamping tubular vessel 200 against the tissue contacting surface of staple cartridge 34. In addition, when actuation shaft 40 advances distally, the clasp portion 102 of rack lock 80 engages a notched area 214 formed in the distal end portion of actuation shaft 40 distal of toothed rack 42 under the bias of torsion spring 106. Thereupon, the longitudinal position of actuation shaft 40 within barrel portion 22 is maintained, and anvil 36 is locked in a closed position.

Figure 8:
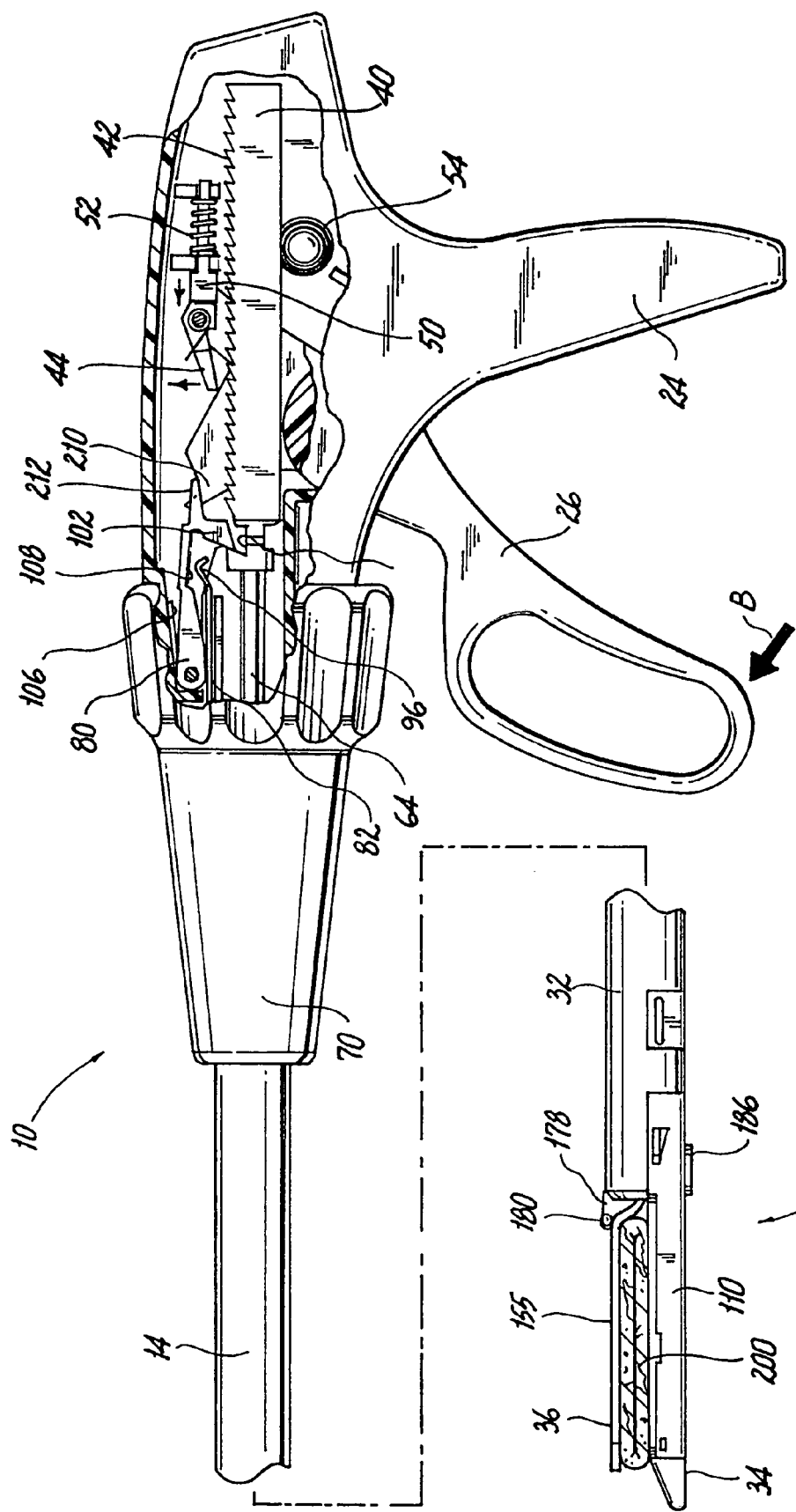
FIG. 8 is a side elevational view of the surgical stapling apparatus of the subject application with the handle portion sectioned to illustrate the relative positions of the components of the actuation assembly when the actuation handle is released to permit the anvil of the disposable loading unit to move to an open position.
Figure 9:
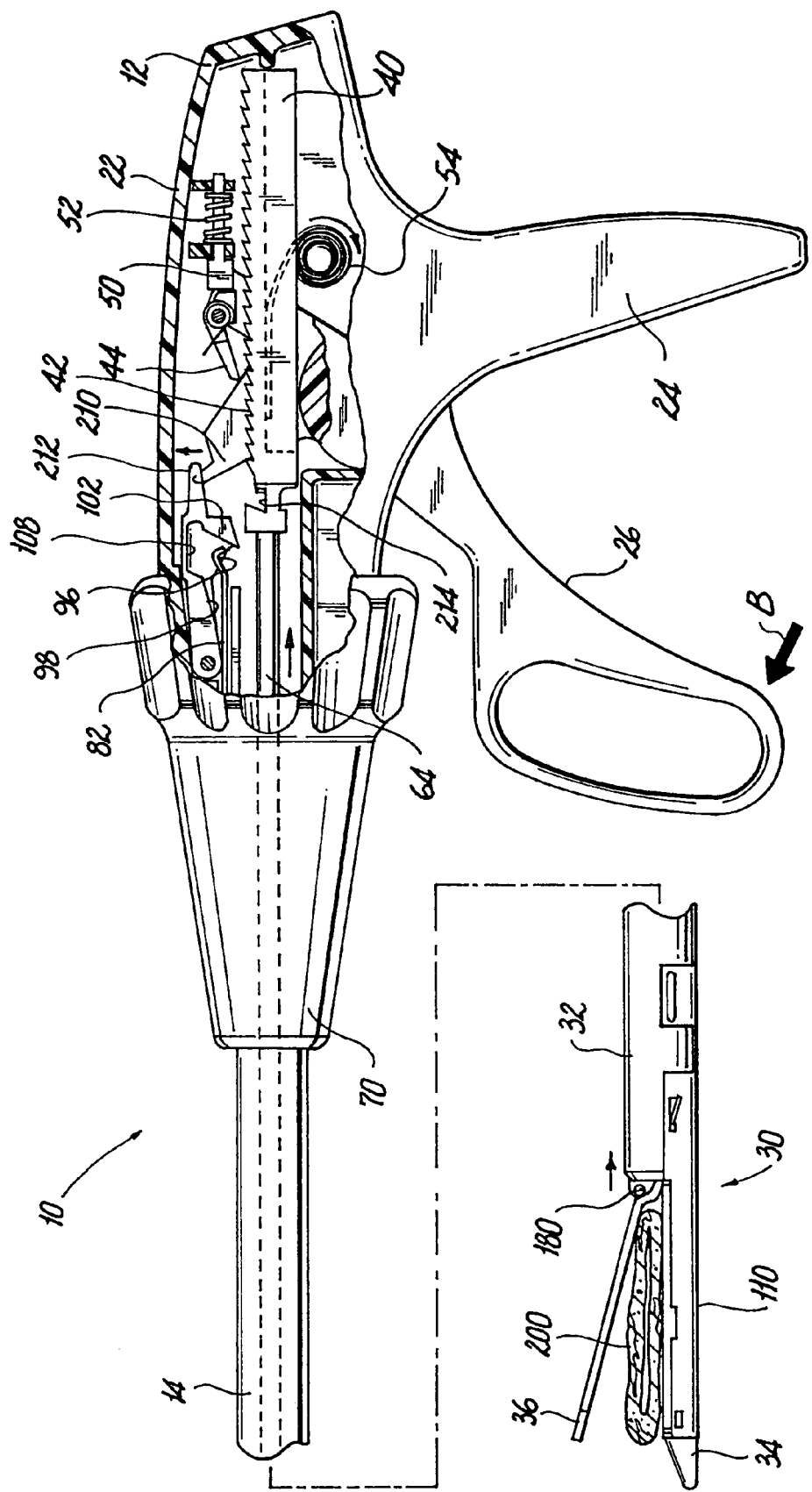
FIG. 9 is a side elevational view of the surgical stapling apparatus of the subject application with the handle portion sectioned to illustrate the relative positions of the components of the actuation assembly when the actuation handle is moved to a position wherein the anvil of the disposable loading unit is maintained in an open position.

Under certain circumstances it may be necessary to open the anvil and unclamp the captured vessel or body tissue, i.e., to recapture the vessel at a different location. As illustrated in FIG. 8, to release the anvil, actuation handle 26 is manipulated in the direction indicated by reference arrow "B" against the bias of linear compression spring 52. As a result, arm 210 lifts finger 212, rotating rack lock 80 in a counter-clockwise direction against the bias of torsion spring 106, as shown in FIG. 9. The clasp portion 102 of rack lock 80 is thereby disengaged from notched area 214, permitting actuation shaft 40 and control rod 64 to return to their proximal-most positions. At such a time, drive block 168 moves proximally under the bias of spring members 194 and 196. Accordingly, cam roller 180 is drawn off of the exterior camming surface 182 of anvil 36, and the anvil moves to an open position under the bias of spring member 158. Subsequent anvil closure is achieved in the manner described hereinabove with reference to FIG. 7.

Figure 10:
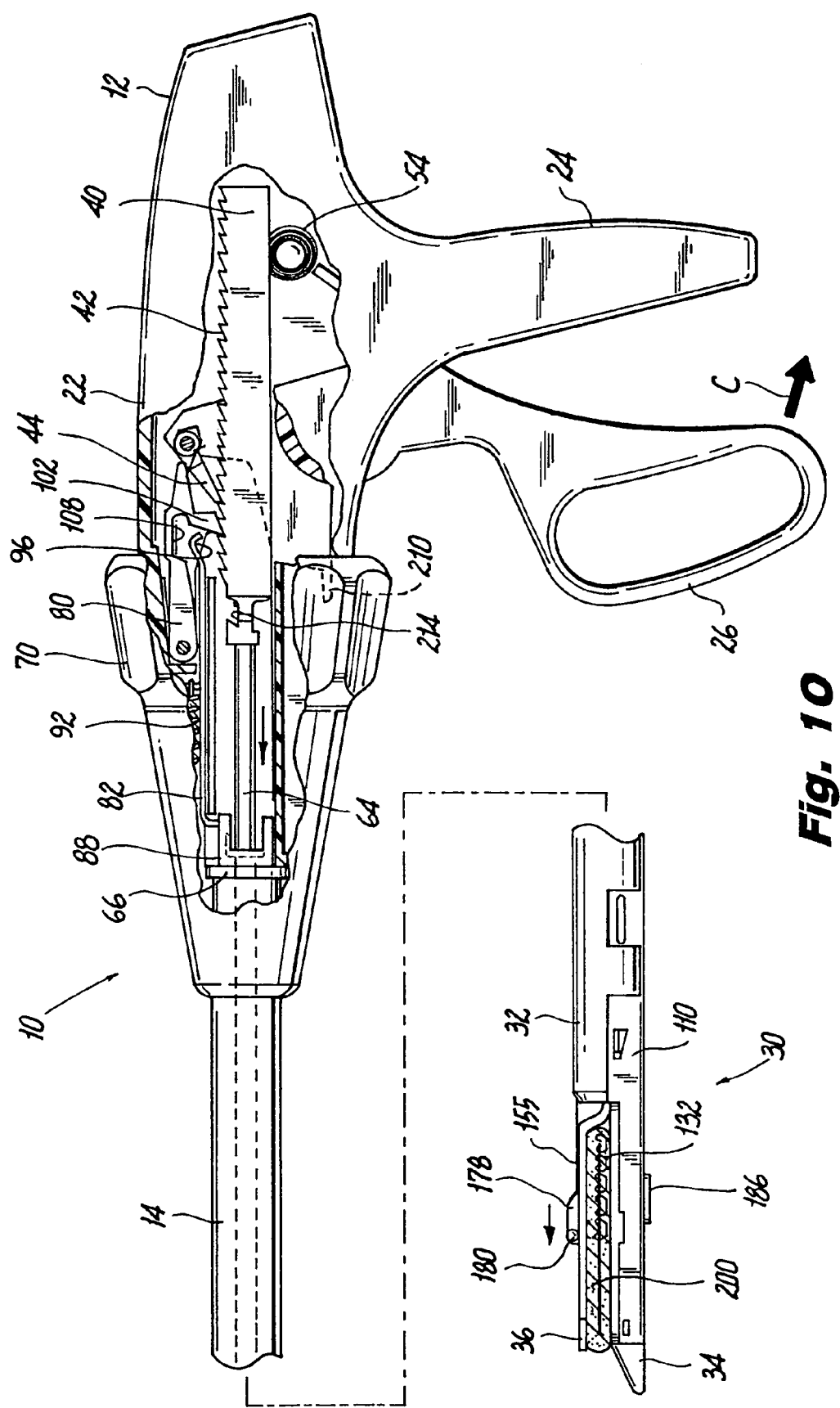
FIG. 10 is a side elevational view of the surgical stapling apparatus of the subject application with the handle portion sectioned to illustrate the relative positions of the components of the actuation assembly when the actuation handle is manipulated through one complete actuation stroke to apply a portion of the staples from the staple cartridge of the disposable loading unit to body tissue.

Referring to FIG. 10, to fire instrument 10 and apply a plurality of surgical fasteners 132 to the tissue clamped between anvil 36 and staple cartridge 34, actuation handle 26 is manipulated toward stationary handle 24 in the direction indicated by reference arrow "C" against the bias of torsion spring 38. Thereupon, pawl 44 engages toothed rack 42 and drives actuation shaft 40 distally against the bias of constant force spring 54. In a preferred embodiment of firing a disposable loading unit having linear rows of staples, one complete stroke of actuation handle 26 causes actuation shaft 40 to advance approximately 15 mm within barrel portion 22, urging drive beam 162 an equivalent distance within disposable loading unit 30 as control shaft 64 transmits longitudinal motion thereto. As a result, half of the surgical fasteners 132 within 30 mm staple cartridge 34 are ejected therefrom upon moving actuation handle 26 one complete stroke. Actuation shaft 40 is maintained in this longitudinally advanced position through the engagement of the clasp portion 102 of rack lock 80 and the toothed rack 42. Subsequent release and movement of actuation handle 26 to a relaxed position will therefore have no bearing on the longitudinal position of actuation shaft 40.

To complete the staple firing operation, actuation handle 26 is once again approximated toward stationary handle 24, causing pawl 44 to engage toothed rack 42 and advance actuation shaft 40 in a distal direction another 15 mm. Thus, two complete strokes of actuation handle 26 causes actuation shaft 40 to advance 30 mm within barrel portion 22, urging the working end 164 of drive beam 162 through staple cartridge 34 to sequentially eject all of the surgical fasteners therefrom. If desired, the operator can incrementally advance control shaft 64 by multiple short strokes, wherein the minimum advancement is dictated by the linear distance between the teeth on rack 42. Therefore, while two complete strokes of the preferred stroke distance of 15 mm can be used (to fire a 30 mm disposable loading unit), complete strokes are not necessary or required.

As best seen in FIGS. 12–14, two complete strokes of actuation handle 26 causes actuation shaft 40 and the associated control rod 64 to translate from the proximalmost position illustrated in FIG. 12, wherein drive block 168 is disposed adjacent the proximal end of channel 110, to the distal-most position illustrated in FIG. 13, wherein drive block 168 travels to the distal end of staple cartridge 34. During its travel, drive block 168 urges drive beam 166 distally, effectuating progressive closure of anvil 36 against tubular vessel 200, and sequential ejection of surgical fasteners 132 into the body tissue as actuation sled 140 travels through staple cartridge 34. As shown in FIG. 13, when cam roller 180 reaches the distal end of its travel, it drops into the transverse slot 185 formed at the distal end of anvil slot 184. As a result, anvil 36 returns to an open position under the bias of spring member 158, releasing the stapled body tissue as illustrated in FIG. 14. Furthermore, spring members 194 and 196 rewind and return to a coiled condition at the proximal end of channel 110.

Figure 11:
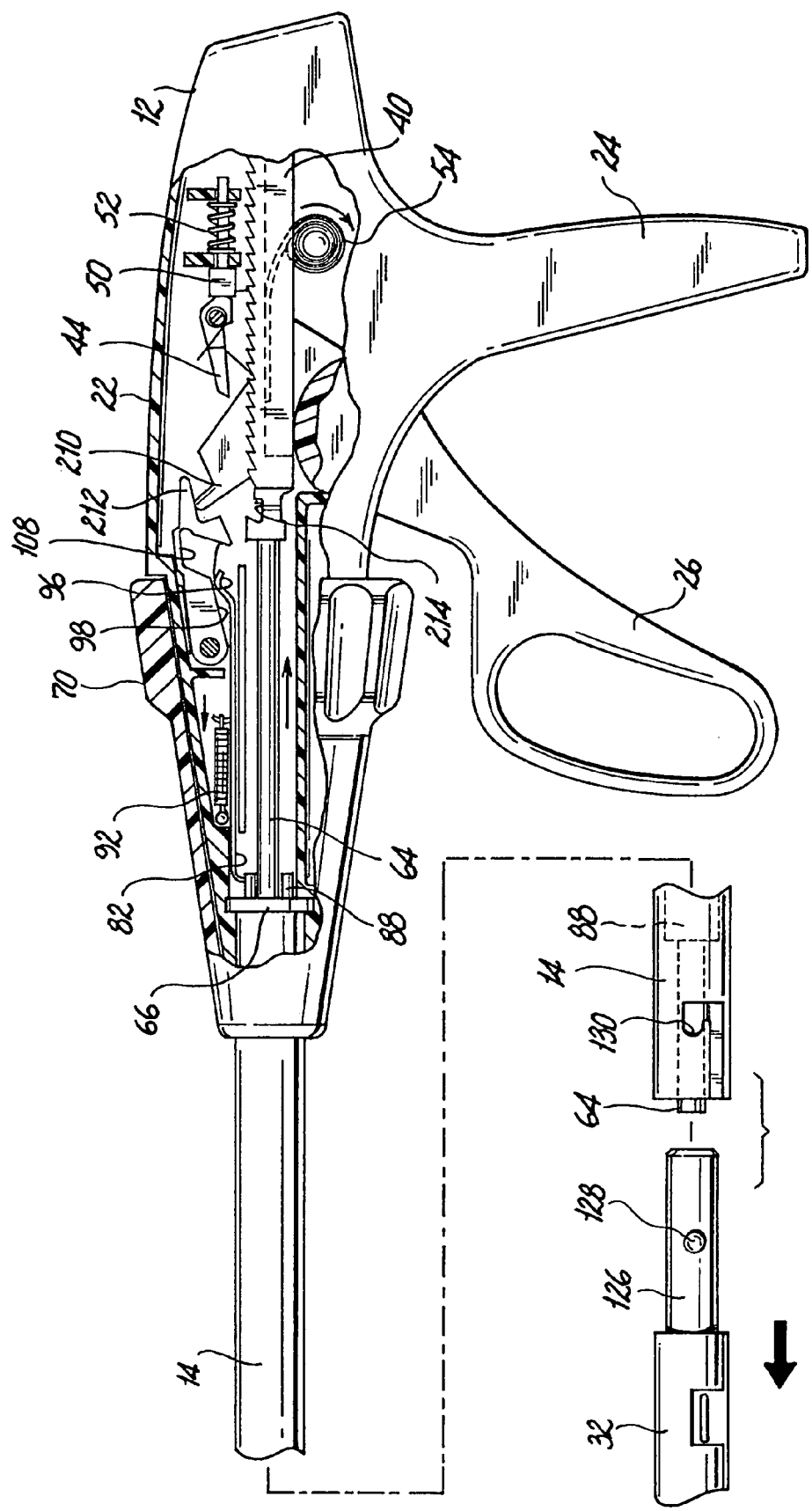
FIG. 11 is a side elevational view of the surgical stapling apparatus of the subject application with the handle portion sectioned to illustrate the relative positions of the components of the actuation assembly when the disposable loading unit is removed from the distal end of the stapler body.

At the conclusion of the above-described firing operation, disposable loading unit 30 is removed from the distal end of elongated body 14, as illustrated in FIG. 11. At such a time, support tube 88 is permitted to return to its distal-most position under the bias of spring 92. Accordingly, beam 82 translates distally causing arcuate cam finger 96 to lift rack lock 80 out of engagement with the toothed rack 42 of actuation shaft 40. As a result, actuation shaft 40 returns to its proximal-most position within barrel portion 22 under the bias of constant force spring 54. Thereupon, a new disposable loading unit can be joined with the instrument and another surgical task performed.

If the surgeon desires to apply parallel rows of staples each measuring about 45 mm in length, disposable loading unit 45 (FIG. 1) is mounted to the distal end portion of elongated body 14. After mounting, actuation handle 26 is manipulated through a number of strokes equalling three complete actuation strokes to incrementally advance actuation shaft 40 and control rod 64 a distance of 45 mm. Alternatively, if disposable loading unit 60 is selected for utilization to apply staple rows measuring about 60 mm in length, actuation handle 26 must be manipulated through a number of strokes equalling four complete actuation strokes to incrementally advance actuation shaft 40 and control rod 64 a distance of 60 mm.

Turning to FIGS. 15 and 16, two alternate embodiments of disposable loading units are shown. Disposable loading unit 410 in FIG. 15 is designed to apply surgical clips. Disposable loading unit 410 has jaw structure 412 and a plurality of clips disposed in housing 414. Commonly assigned U.S. Pat. No. 5,100,420, the disclosure of which is herein incorporated by reference in its entirety, discloses a manner in which clips can be fed to jaw structure 412 and formed. Disposable loading unit 420 in FIG. 16 is designed to apply individual surgical staples, such as those useful during hernia repair. Disposable loading unit 420 has jaw structure 422 and a plurality of staples disposed in housing 424. Commonly assigned U.S. Pat. No. 5,289,963, the disclosure of which is herein incorporated by reference in its entirety, discloses a manner in which staples can be fed to jaw structure 422 and formed. Both disposable loading units 410 and 420 are secured to the surgical instrument in a manner similar to the disposable loading units previously described and are actuated by the longitudinal motion of actuation shaft 40 and control rod 64.

It is readily apparent and may be appreciated by those having ordinary skill in the art that the stroke distance travelled by the actuation shaft may be adjusted in accordance with desired surgical practices. For example, it may be desirable to employ disposable loading units which apply parallel staple rows measuring 40 mm, 60 mm, or 80 mm. Thus, the incremental stroke distance travelled by the actuation shaft could be adjusted to approximately 20 mm intervals. In addition, one skilled in the art could provide alternate structure or orientation of structures to control the advancement of control rod 64. For example, toothed rack 42 could be rotated so the teeth face downward towards the handles and the locks and pawls moved to engage the rack from the underside. Also, various safety mechanisms can be added, such as a lockout in the handle that needs to be released prior to actually firing a disposable loading unit. These and other features are described in greater detail, below.

Figure 17:
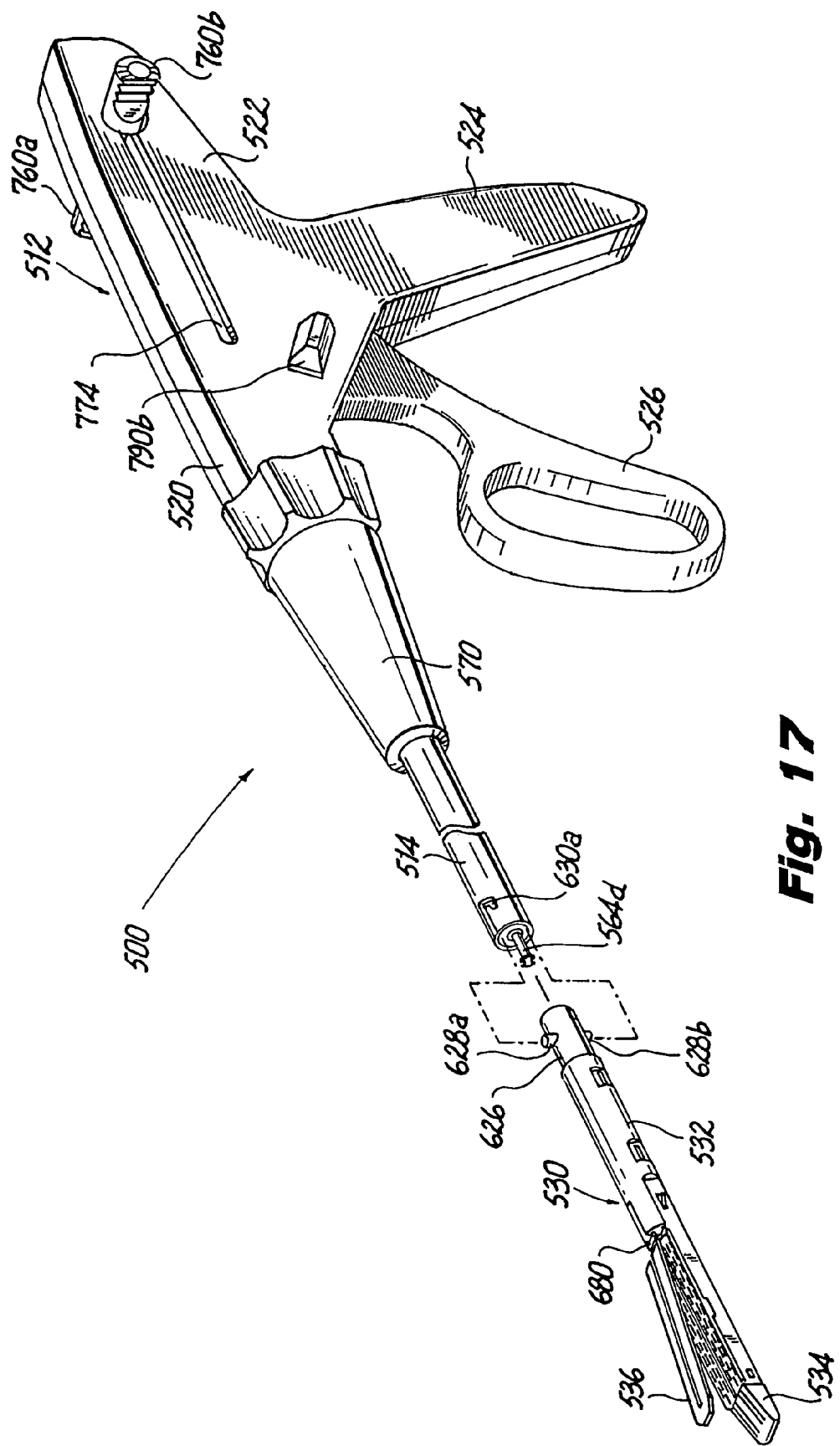
FIG. 17 is a perspective view of another surgical stapling apparatus constructed in accordance with a preferred embodiment of the subject invention illustrated in conjunction with one of several different sized disposable loading units employed with the apparatus.

Referring now to FIG. 17, there is illustrated another surgical stapling apparatus constructed in accordance with a preferred embodiment of the subject application and designated generally by reference numeral 500. As in the previously described embodiment, surgical stapling apparatus 500 is configured to engage body tissue, apply a plurality of surgical fasteners thereto, and form an incision in the fastened body tissue during a laparoscopic surgical procedure. The apparatus is preferably configured to operate with individual disposable loading units that apply linear rows of staples measuring 30 mm, 45 mm, or 60 mm in length (see generally FIG. 1), or other types of disposable loading units (see, generally FIGS. 15 and 16).

As illustrated in FIG. 17, surgical stapler 500 has a handle assembly 512 and an elongated body 514, and is adapted for use with a disposable loading unit 530, among other units not shown, which has a carrier 532, a staple cartridge 534, and an anvil 536 against which staples are driven when ejected from the cartridge.

Figure 18:
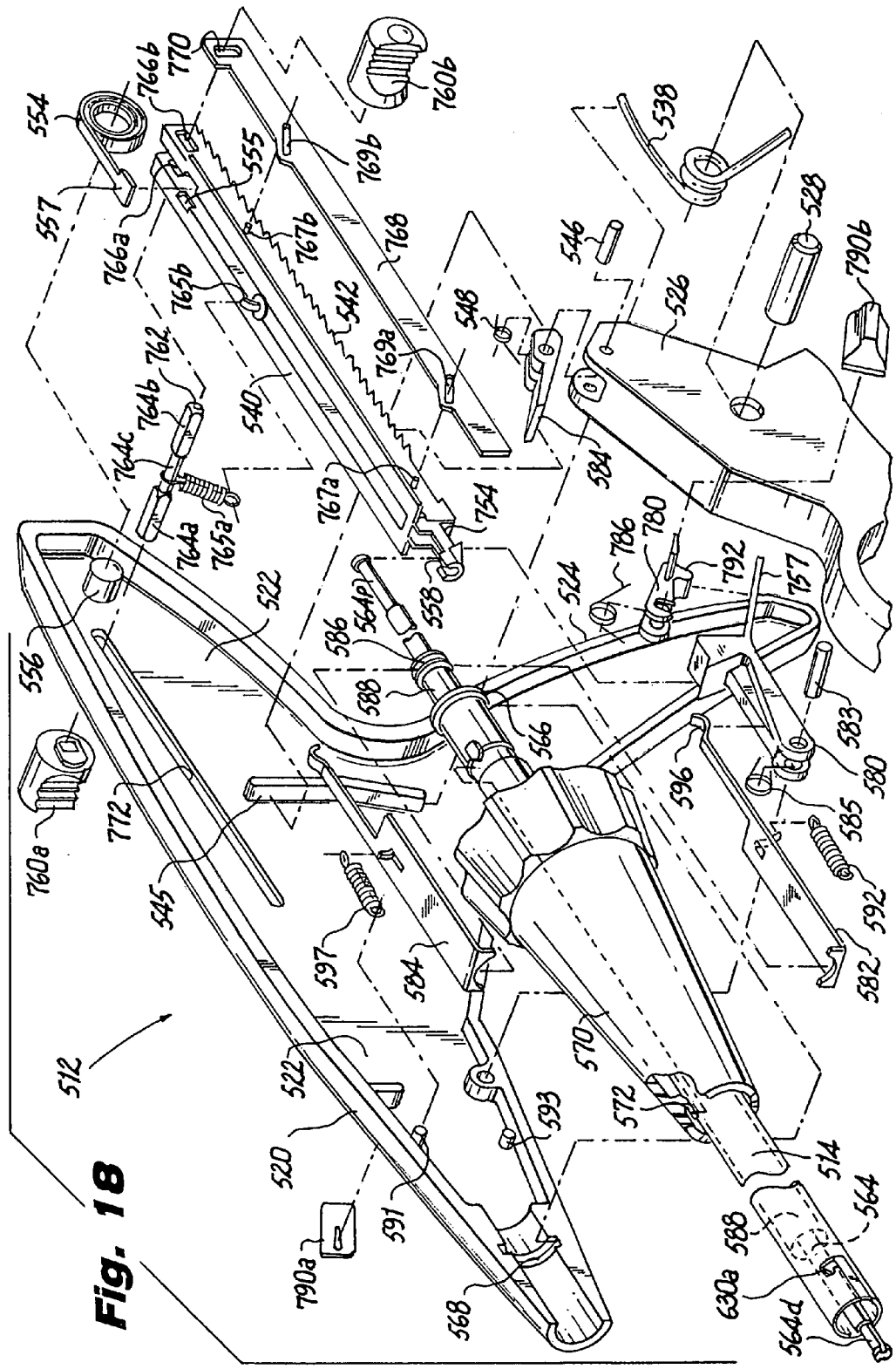
FIG. 18 is an exploded perspective view of the handle assembly of the surgical stapling apparatus of FIG. 17 with the components associated therewith separated for ease of illustration.

Referring to. FIG. 18, as in the previous embodiment, handle assembly 512 includes a housing 520 defined by a barrel portion 522, a stationary handle 524, and a pivoting actuation handle 526. Actuation handle 526 is supported in housing 520 by pivot pin 528 and is biased away from stationary handle 524 by a torsion spring 538. Actuation handle 526 controls the linear movement of actuation shaft 540 which is supported within the barrel portion 522 of housing 520. More particularly, actuation shaft 540 has a toothed rack 542 defined on an undersurface thereof and actuation handle 526 is provided with a pawl 544 which is mounted to selectively engage toothed rack 542 and advance the actuation shaft 540 in a distal direction in response to manipulation of actuation handle 526 through an actuating stroke. Pawl 544 is mounted to actuation handle 526 by a pivot pin 546 and is biased toward toothed rack 542 by a coiled torsion spring 548. The mounting portion of pawl 544 is curved to interact with an abutment wall 545 defined within the housing 520 of handle assembly 512. More particularly, when the curved mounting portion of pawl 544 contacts abutment wall 545, the pawl is rotated out of engagement with the toothed rack 542 of actuation shaft 540.

Actuation shaft 540 is normally biased in a proximal direction within barrel portion 522 by a constant force spring 554 which is supported on a boss 556 provided within housing 520. A notched area 555 is formed in the upper surface of actuation shaft 540 adjacent the proximal end thereof for receiving and retaining an engagement tab 557 provided at the free end of constant force spring 554. The distal end of actuation shaft 540 is provided with a catchment fitting 558 for engaging the flanged proximal end 564p of control rod 564. Control rod 564 extends from the handle assembly 512 through the elongated body portion 514 to interact with the disposable loading unit 530 supported at the distal end of the body portion. Accordingly, manipulation of actuation handle 526 causes corresponding longitudinal translation of the actuation shaft 540 and control rod 564 to actuate the disposable loading unit in a manner which will be discussed in detail hereinbelow.

With continuing reference to FIG. 18, the proximal end of the elongated body portion 514 of surgical stapler 500 has an annular flange 566 formed thereon which is received in a corresponding annular recess 568 formed within the barrel portion 522 adjacent the distal end thereof. This connection facilitates rotational movement of body 514 relative to handle assembly 512 about a longitudinal axis extending therethrough. A collar 570 is fixedly mounted to body portion 514 by at least one protuberance 572 to effectuate the axial rotation of body portion 514 and thereby increase the operational range of surgical stapler 500.

As in the previously described embodiment, surgical stapler 500 includes a rack lock (or engagement member) 580 which interacts with the toothed rack 542 of actuation shaft 540 to selectively maintain the longitudinal position thereof within barrel portion 522 against the bias of constant force spring 554. Rack lock 580 is mounted in such a manner so as to move into a position to interact with toothed rack 542 only when a disposable loading unit has been inserted into the distal end of body portion 514. More particularly, rack lock 580, which is mounted on a pivot pin 583 and biased toward the toothed rack 542 by a coiled torsion spring 585, is maintained in a non-interactive position by an abutment strut 582 until a disposable loading unit is loaded into the device. Abutment strut 582 is mounted on a securement flange 586 formed at the proximal end of a support tube 588 which is mounted for axial translation within body portion 514 (see FIG. 21). A coiled biasing spring 592 connects abutment strut 582 to a boss 593 in the housing 520 of handle assembly 512, and, in effect, biases the support tube 588 in a distal direction so that upon insertion of a disposable loading unit, support tube 588 and abutment strut 582 are shifted in a proximal direction.

Figure 22:
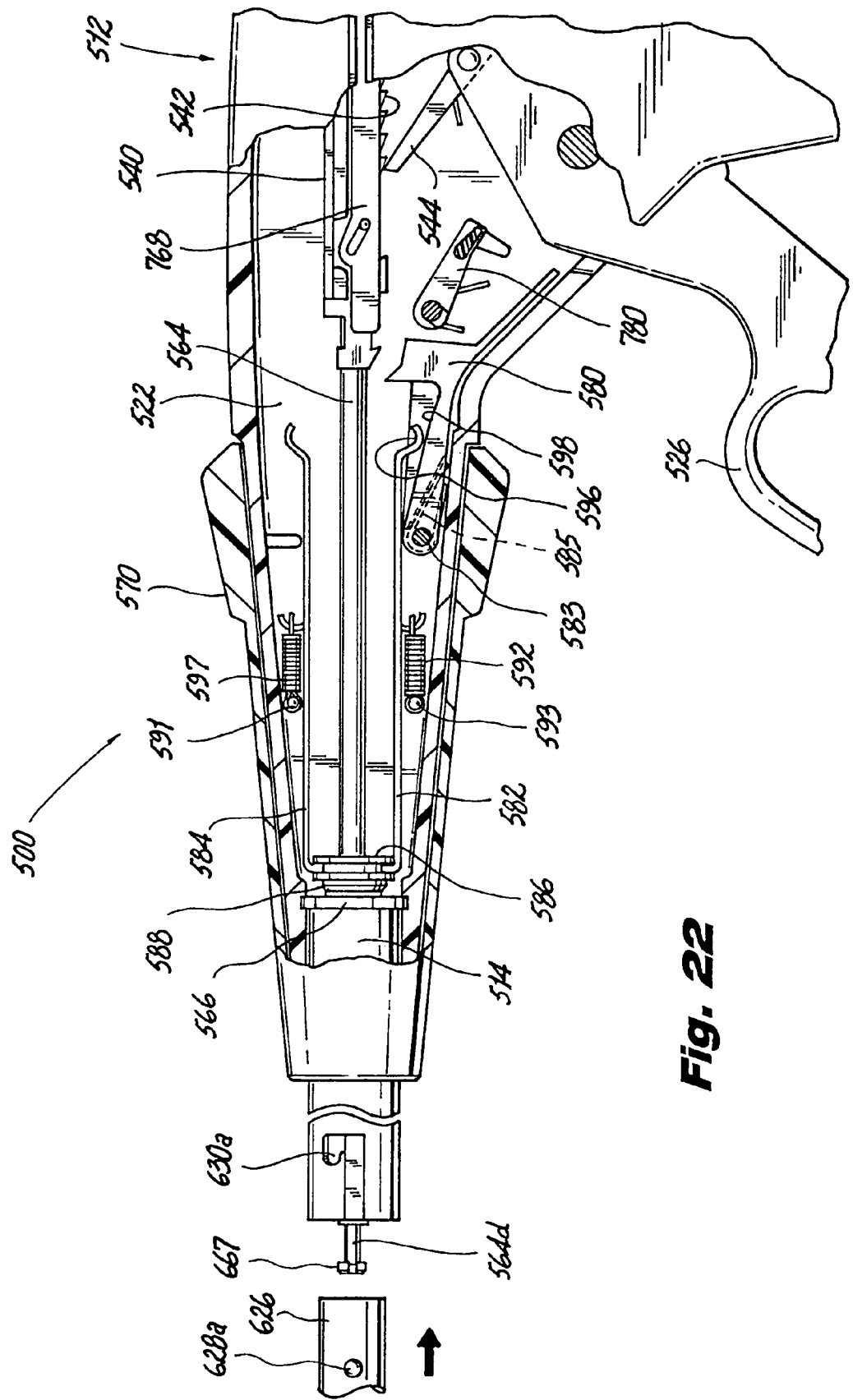
FIG. 22 is a side elevational view in partial cross-section of the surgical stapling apparatus of FIG. 17 illustrating the orientation of the rack lock prior to mounting the disposable loading unit in the distal end of the body portion.
Figure 23:
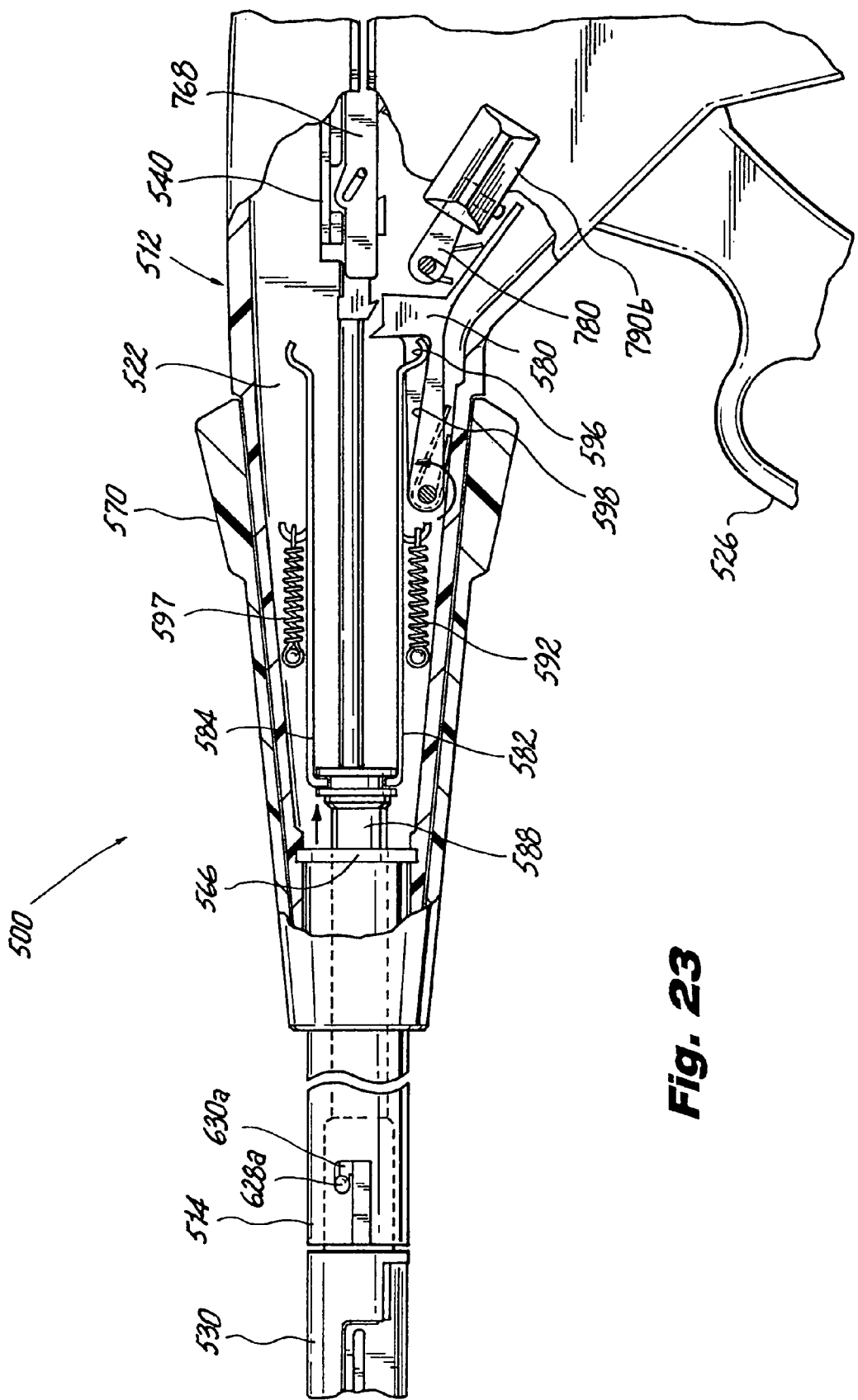
FIG. 23 is a side elevational view in partial cross-section of the surgical stapling apparatus of FIG. 17 illustrating the orientation of the rack lock after the disposable loading unit has been mounted in the distal end of the body portion.

More specifically, as illustrated in FIG. 22, prior to insertion of loading unit 530, an arcuate camming finger 596 which projects proximally from abutment strut 582 is in contact with a distal portion of an angled camming surface 598 defined on rack lock 580. At such a time, rack lock 580 is maintained in a non-interactive position against the bias of coiled torsion spring 585. Thereafter, as shown in FIG. 23, when loading unit 530 is inserted into the distal end of body portion 514 and rotated to engage the bayonet connection associated therewith (stems 628*a* and 628*b*, slots 630*a* and 630*b*), support tube 588 and abutment strut 582 are urged proximally against the bias of coiled spring 592 (and coiled spring 597). As a result, the proximal camming finger 596 translates in a proximal direction along camming surface 598, permitting rack lock 580 to rotate about pin 583 under the bias of torsion spring 585 into an interactive position in which the toothed rack 542 of actuation shaft 540 may be engaged upon the distal translation thereof.

As illustrated in FIGS. 22 and 23, a second abutment strut 584 is disposed opposite abutment strut 582 and is connected to the proximal end of support tube 588 in the same manner as abutment strut 582. Abutment strut 584, and the spring 597 which is associated therewith and connected to housing 520 by boss 591, provide additional biasing force to securely maintain the bayonet connection between the disposable loading unit 530 and the body portion 514.

Referring to FIG. 19, an elongated slot 602 extends along a portion of support tube 588 and a transverse groove 604 extends along the axial bore 606 of body portion 514 to accommodate a support pin 608 which extends radially outwardly from the central portion of control rod 564. This connection permits longitudinal movement of support tube 588 with respect to body portion 514 and control rod 564 while maintaining the respective angular orientation of the three coaxial structures to facilitate their axial rotation by collar 570.

Figure 24:
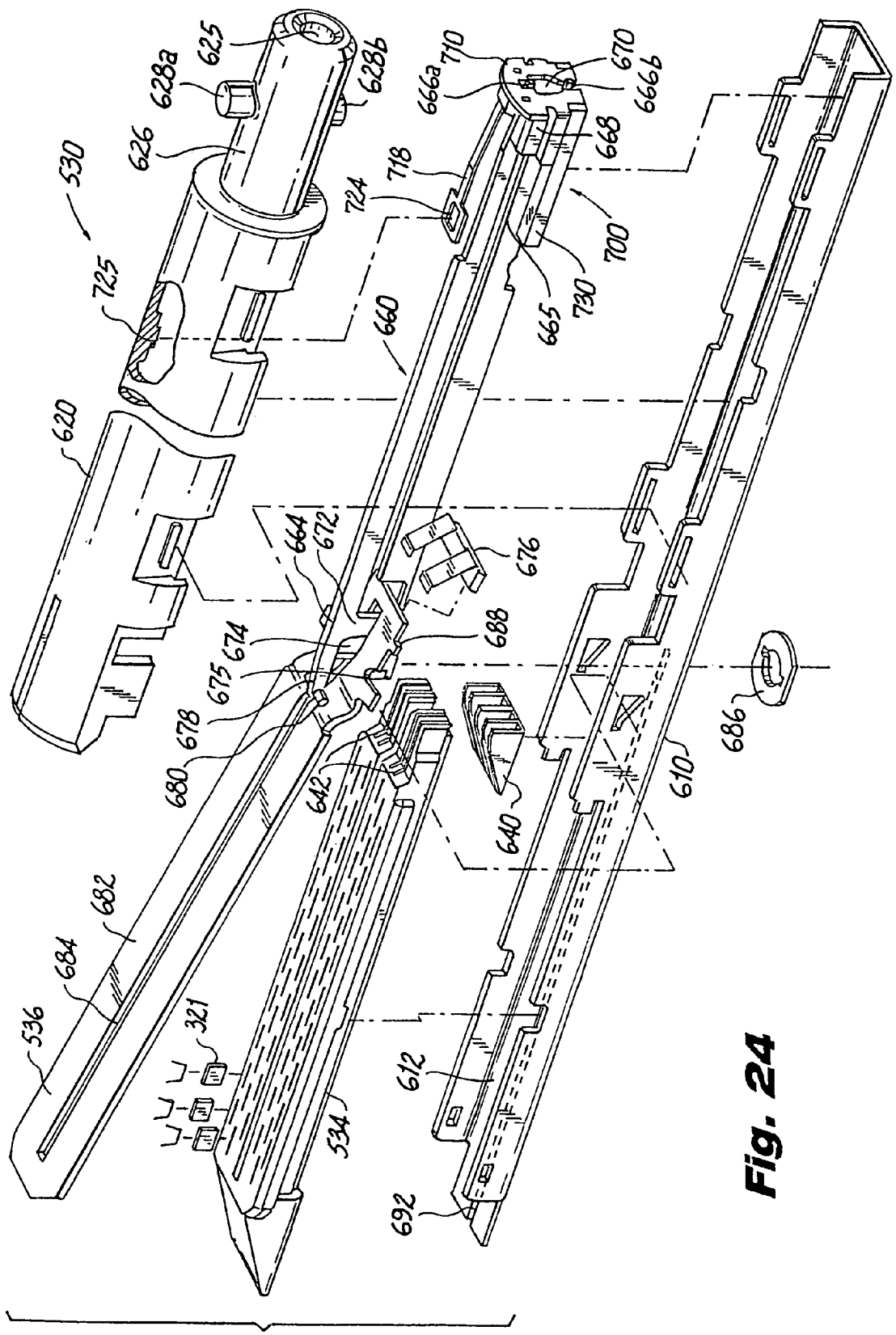
FIG. 24 is an exploded perspective view of a disposable loading unit constructed in accordance with a preferred embodiment of the subject invention which includes a lockout assembly that functions to limit the longitudinal translation of the control shaft illustrated in FIGS. 19 and 20.

Turning now to FIG. 24, there is illustrated disposable loading unit 530 which is constructed in a manner that is substantially similar to the loading unit illustrated in FIG. 3. It includes a carrier 532 having an elongated support channel 610 for supporting staple cartridge 534 and anvil 536 and a mounting portion 620 which is configured for releasable engagement in the distal end of body portion 514. More particularly, the proximal end portion 626 of mounting portion 620 is provided with a pair of coupling stems 628*a* and 628*b* which interact with the J-shaped coupling slots 630*a* and 630*b* formed at the distal end of body portion 514 (see, for example, FIG. 26). The coupling stems and J-shaped slots together define the conventional bayonet-type coupling which facilitates the engagement and removal of the loading unit from the stapler. As in the previous embodiment, an axial bore 625 extends through the proximal end 626 of mounting portion 620 to receive the distal end portion 564*d* of control rod 564.

As in the previous embodiment, disposable loading unit 530 includes an axial drive assembly 660 which, among other things, transmits the longitudinal drive forces exerted by control rod 564 to the actuation sled 640 disposed within the spaced apart longitudinal slots 642 that extend through staple cartridge 534. A plurality of staple pushers 643 are operatively associated with slots 642 and are sequentially contacted by actuation sled 640 as it is driven through staple cartridge 534 by drive assembly 660. The staple pushers interact with the plurality of staples housed within staple cartridge 534 to sequentially eject the staples therefrom.

Drive assembly 660 includes a bifurcated drive beam 662 having a distal working head 664 and a proximal engagement section 665 that includes a pair of engagement fingers 666*a* and 666*b* (see FIG. 25) configured to mountingly engage a drive block 668. Drive block 668 has a proximal porthole 670 for receiving the distal end 564*d* of control rod 564 when the proximal mounting portion 626 of loading unit 530 is inserted into the distal end of elongated body portion 514, as illustrated, for example, in FIG. 27.

Referring to FIG. 20, the distal end portion 564*d* of control rod 564 is formed with a flange 667 having a pair of diametrically opposed notches 669*a* and 669*b* dimensioned to accommodate the two opposed engagement fingers 666*a* and 666*b* when the control rod is received in the proximal portal 670 of drive block 668, as best seen in FIGS. 26 and 29. Thereafter, as illustrated in FIGS. 28 and 30, when loading unit 530 is rotated through approximately a 20° axial turn to engage coupling stems 628*a* and 628*b* within J-shaped coupling slots 630*a* and 630*b*, engagement fingers 666*a* and 666*b* are moved out of alignment with engagement notches 669*a* and 669*b*, and flange 667 is secured from exiting disposable loading unit 530 until its removal from surgical stapler 500. As seen when comparing FIGS. 27 to FIG. 28, the interior cavity 671 of drive block 668 is dimensioned to accommodate thee extension of the distal portion 564*a* of control rod 564 into portal 670 during the insertion of the loading unit 530 into the distal end of body portion 514.

Referring again to FIG. 24, the working head 664 of drive assembly 660 is defined in part by vertical support strut 672 which supports a knife blade 674, and defines an abutment surface 675 for engaging actuation sled 640. A retention flange 678 projects distally from support strut 672 to retain a cam roller 680 which is configured to translate along the exterior camming surface 682 of anvil 536 during a stapling procedure to effect closure of the anvil against the bias of anvil spring 676. A longitudinal slot 684 extends through anvil 536 to accommodate the translation of retention flange 678, and a similar slot 692 is formed in the base 612 of channel 610 to accommodate the translation of retention foot 688 which supports balancing flange 686. Flange 686 serves to balance the clamping forces exerted by cam roller 680 on anvil 536. As in the previous embodiment, an anvil cover (not shown) can be provided to protect tissue from contacting components traveling along the exterior surface 682 of anvil 536 during a stapling procedure.

Referring to FIGS. 24 and 25, disposable loading unit 530 is provided with a lockout assembly 700 configured to operate in two distinct stages. In brief, during the first stage of operation, the lockout assembly functions to limit the longitudinal movement of control rod 564 with respect to the axial drive assembly 660 (see FIG. 46). In the second stage of operation, i.e., after the disposable loading unit has been removed from the apparatus following a stapling procedure, the lockout assembly serves to prevent subsequent utilization of the loading unit by blocking the entry of control rod 564 into the proximal portal 670 of drive block 668 (see FIG. 51).

As best seen in FIG. 25, preferred lockout assembly 700 includes a blocking plate 710 having a pair of parallel support arms 712a and 712b which depend distally therefrom. A central aperture 716 is formed in blocking plate 710 which is dimensioned and configured to accommodate the longitudinal translation of control rod 564. Aperture 716 includes diametrically opposed slots 717a and 717b to accommodate the engagement fingers 666a and 666b of the proximal portion 665 of actuation beam 662. A retention spring 718 is connected to blocking plate 710 through the engagement of a pair of spaced apart tabs 720a and 720b with a pair of corresponding ports 722a and 722b. Retention spring 718 includes a mounting flange 724 for securing the spring to a mounting area 725 on the interior surface of the mounting portion 620 of disposable loading unit 530 (see FIG. 26). The proximal end portion of retention spring 718 is defined by a pair of spaced apart camming ramps 726a and 726b which are angled proximally to interact with the distal flange 667 of control rod 564 when disposable loading unit 530 is removed from the apparatus (see generally FIG. 47).

Lockout assembly 700 further includes a support plate 730 having a pair of depending arms 732a and 732b which interact with the support arms 712a and 712b of blocking plate 710 to maintain the blocking plate in a non-blocking position against the bias of retention spring 718 (see FIG. 26). Support plate 730 is formed with a central slotted region 733 which accommodates the lower portion of drive beam 662. A detent 734 is formed within slotted region 733 for interacting with distal and proximal complementary recesses 735a and 735b formed in the lower portion of drive beam 662.

Figure 44:
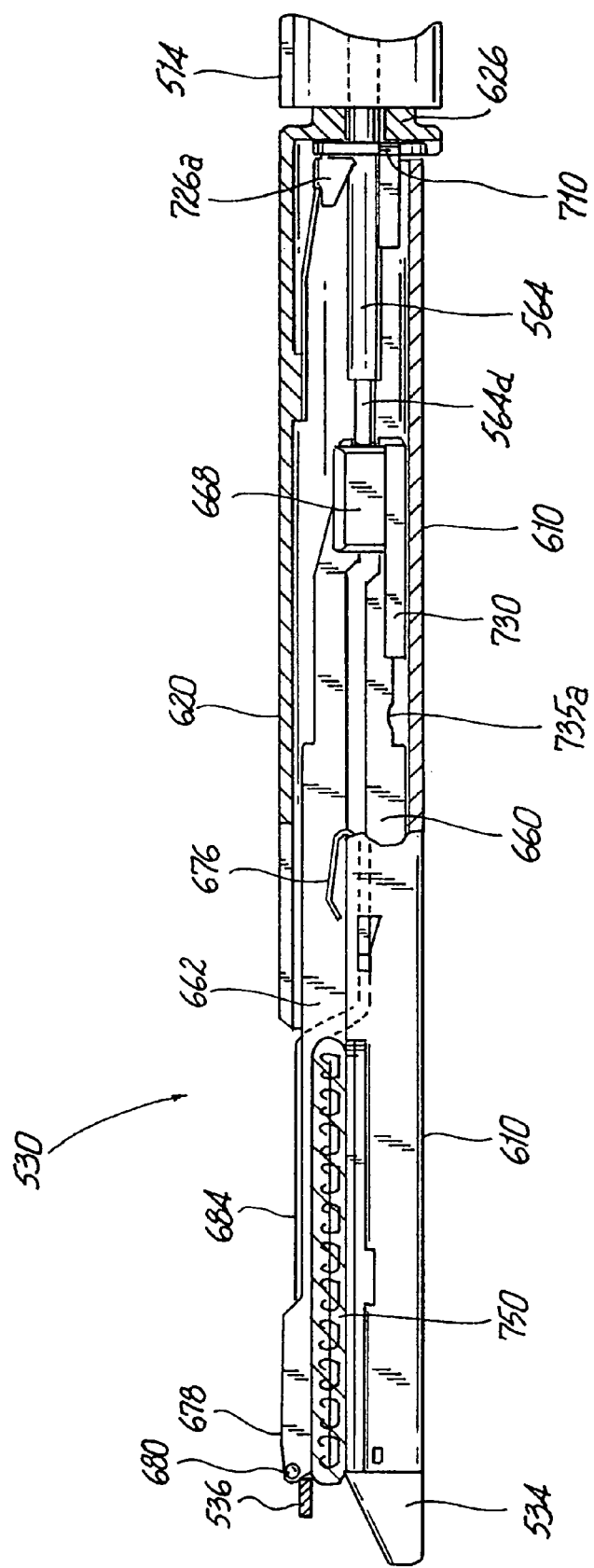
FIG. 44 is a side elevational view in partial cross-section of the disposable loading unit illustrating the position of the axial drive assembly and control rod at the conclusion of a stapling procedure.

In use, when drive beam 662 is driven distally, as shown for example in FIG. 44, support plate 730 is drawn therewith through the engagement of detent 734 with proximal recess 735b. As a result, blocking plate 710 is released and translates in a direction transverse to the longitudinal axis of control rod 564 under the bias of retention spring 718. As shown for example in FIG. 45, while control rod 564 is extending through aperture 716, blocking plate 710 remains in a non-blocking position. However, when control rod 564 is fully retracted to open anvil 536 after a stapling procedure, blocking plate 710 moves into a limiting position, engaging the distal portion 564d of control shaft 564, as illustrated in FIG. 46. In this position, blocking plate 710 effectively limits the range of longitudinal motion of control rod 564, the range being defined by the reduced diameter portion at the distal end of control rod 564.

Upon full withdrawal of flange 667 from drive block 668, blocking plate 710 is free to translate into a full blocking position under the bias of retention spring 718 to block the proximal portal 670 of drive block 668, as illustrated in FIG. 49. The function of lockout assembly 700 and its interaction with control rod 564 and axial drive assembly 660 will be discussed in further detail hereinbelow.

Figure 31:
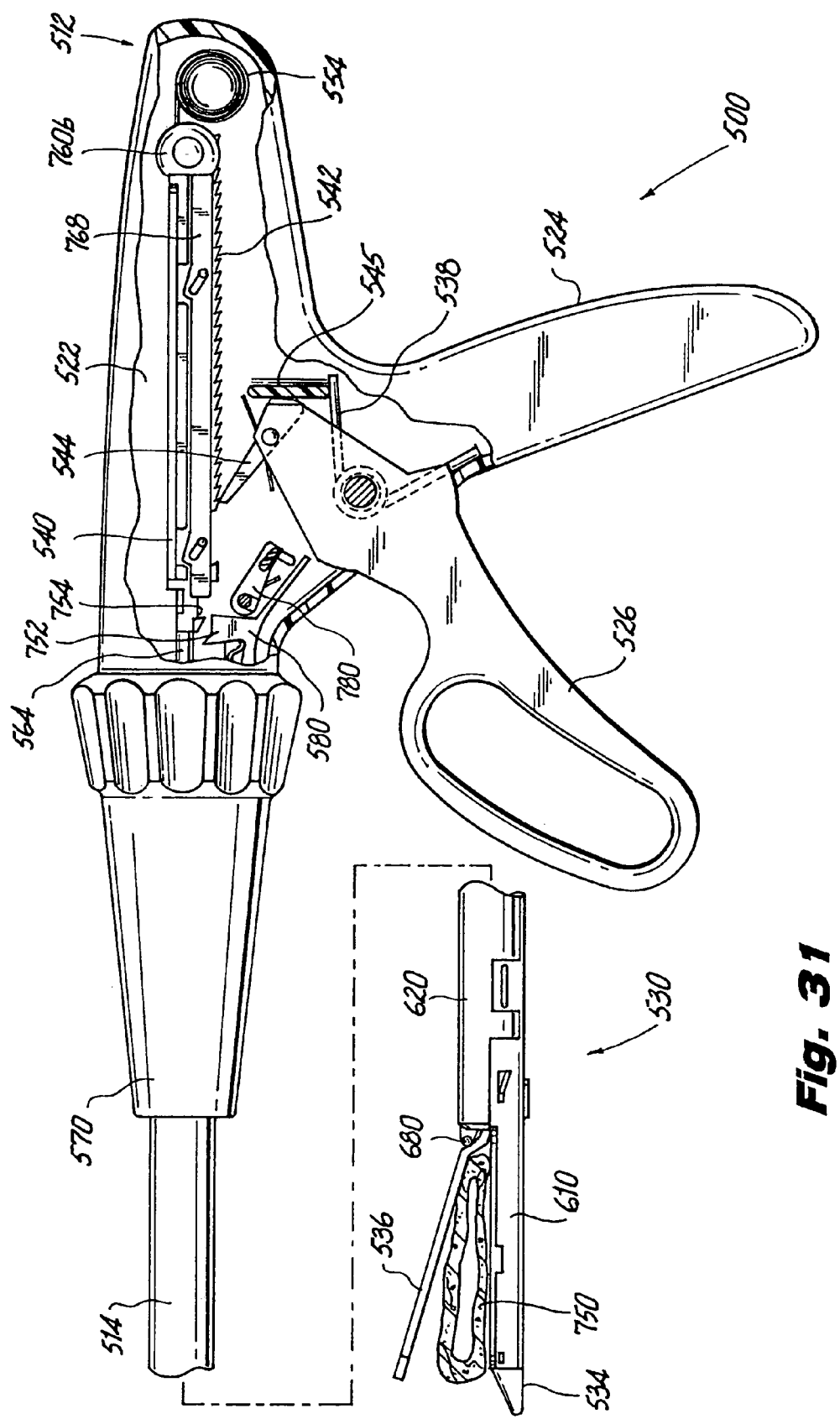
FIG. 31 is a side elevational view in partial cross-section of the surgical stapling apparatus of FIG. 17 prior to a stapling procedure with the anvil in an open position and the actuation shaft and toothed rack disposed in a proximal-most position within the handle assembly.

Referring now in sequential order to FIGS. 31–38, to initiate operation of surgical stapler 500, a desired disposable loading unit of a particular size and kind is selected from a group of different units and loaded into the distal end of body portion 514. The loading unit, i.e., loading unit 530, is mounted to stapler 500 by inserting the proximal mounting portion 626 into the distal end of body portion 514 and rotating the unit to securely engage the bayonet connection (see FIGS. 22 and 23). A preferred degree of rotation is between about 5° and about 40°, while about 20° is most preferred. At such a time, support tube 588 is urged proximally from the position shown in FIG. 22 to that which is illustrated in FIG. 23. As a result, rack lock 580 is moved into an interactive position shown in FIG. 31, wherein the toothed rack 542 of actuation shaft 540 may be engaged upon the distal advancement thereof. As illustrated in FIG. 31, when actuation shaft 540 is in its proximal-most position biased by constant force spring 554, anvil 536 is in an open position to receive body tissue such as tubular vessel 750. At such a time, pawl 544 is engaged in the distal-most tooth on toothed rack 542 and actuation handle 526 may be manipulated against the bias of spring 538 to advance the toothed rack.

Figure 32:
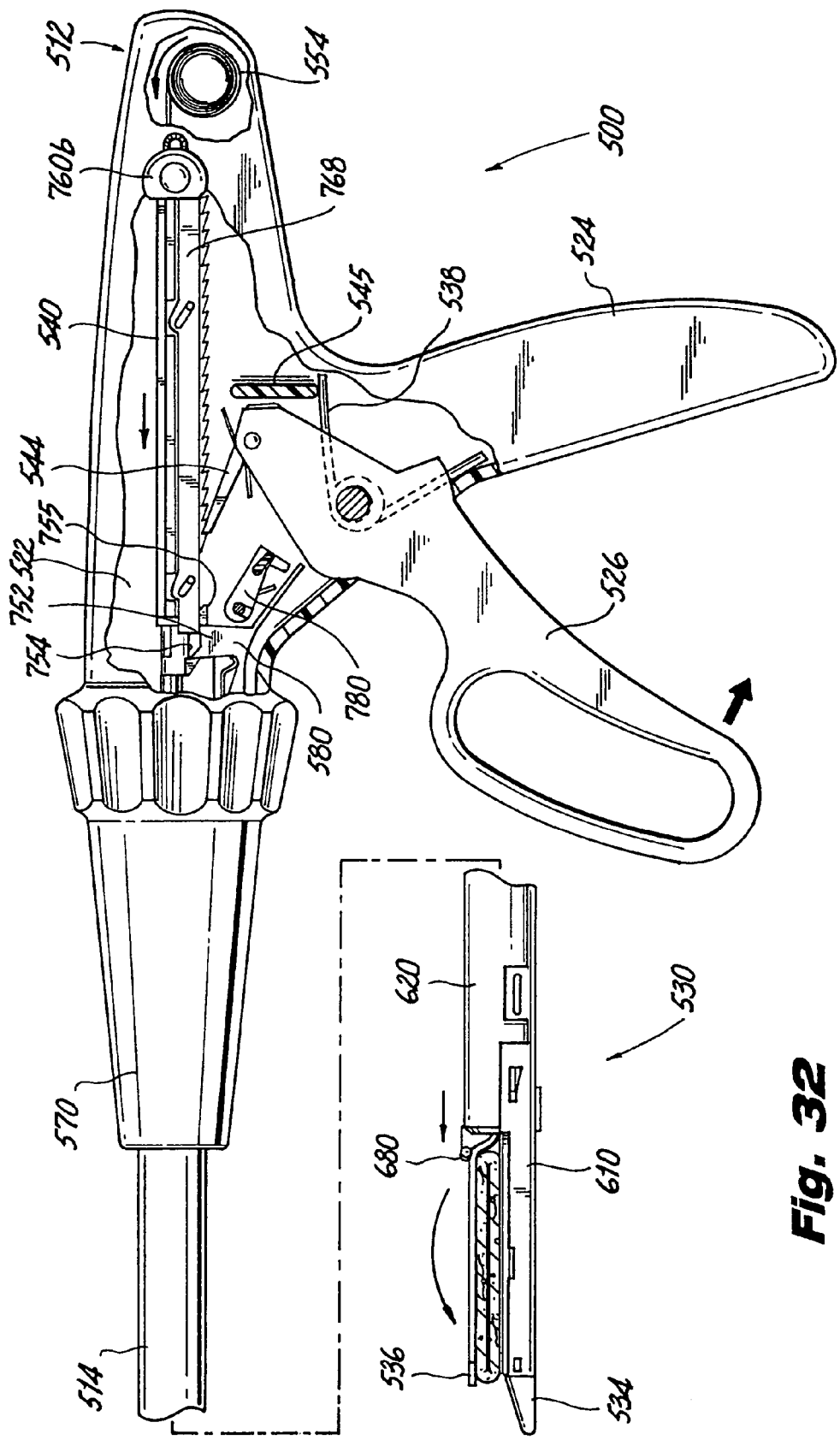
FIG. 32 is a side elevational view in partial cross-section of the surgical stapling apparatus of FIG. 17 illustrating the actuation shaft and toothed rack advanced distally through a clamping stroke to effectuate the movement of the anvil from the open position shown in FIG. 31 to a closed position.

As best seen in FIG. 32, upon initial manipulation of actuation handle 526 through a first segment of the actuation stroke (i.e., the clamping stroke segment), actuation shaft 540 is driven in a distal direction by the interaction of pawl 544 and toothed rack 542. Thereupon, the engagement hook 752 of rack lock 580 engages a keeper notch 754 formed adjacent the distal fastening portion 558 of actuation shaft 540. At such a time, anvil 536 is moved to a closed position by the advancement of cam roller 680 along the proximal camming portion of anvil surface 682, and the proximal end of engagement hook 752 is in abutment with a buttress 755 formed on the under surface of actuation shaft 540. As a result, further distal translation of actuation shaft 540 is prohibited and anvil 536 is maintained in a clamped position.

Figure 33:
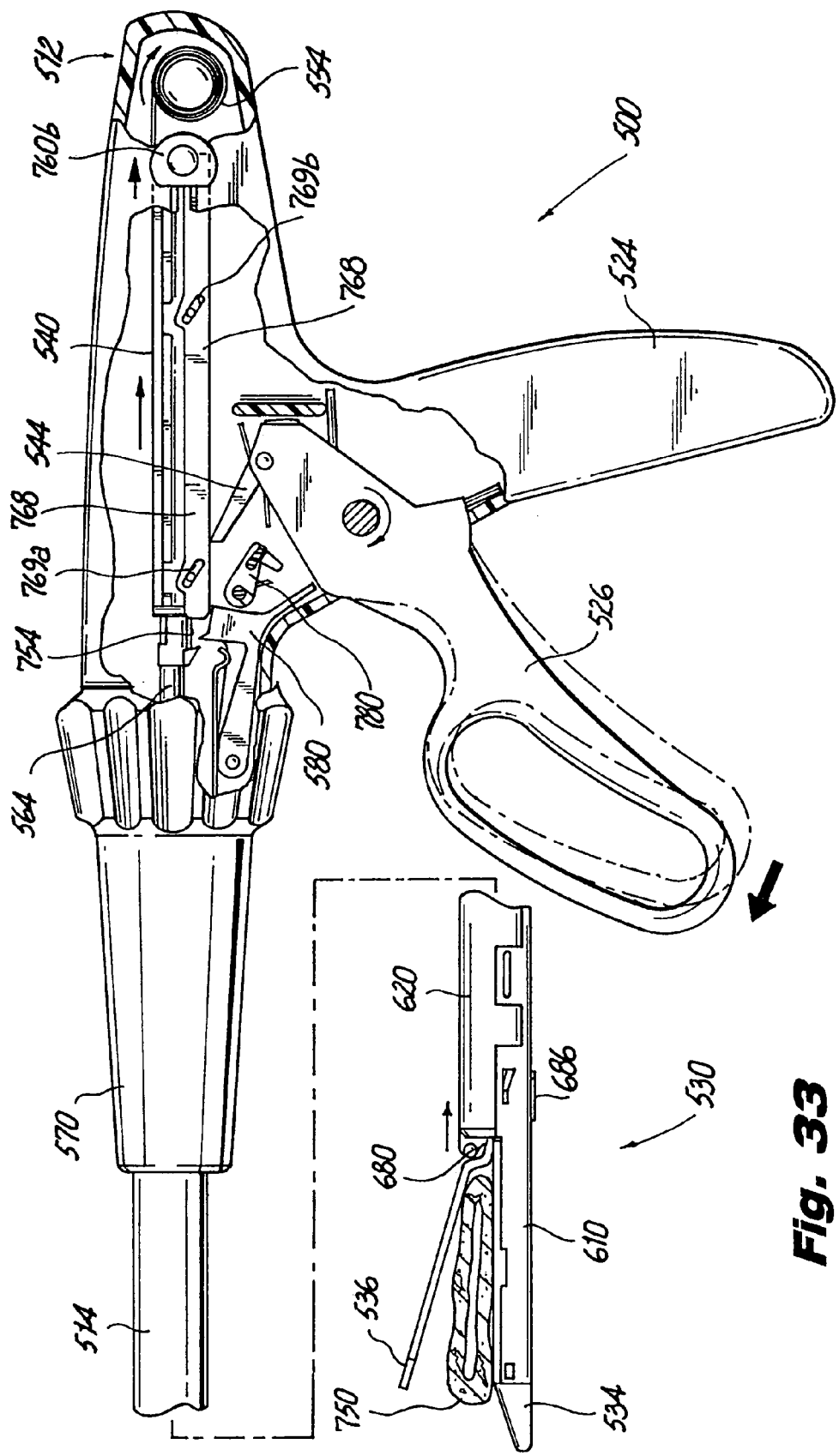
FIG. 33 is a side elevational view in partial cross-section of the surgical stapling apparatus of FIG. 17 illustrating the disengagement of the rack lock and pawl from the actuation shaft and toothed rack by the retraction mechanism to effectuate the movement of the anvil from the closed position shown in FIG. 32 to an open position.

If, at a such a time, the user of the apparatus desires to unclamp tubular vessel 750 by opening anvil 536, this can be accomplished through the manipulation of a retraction mechanism (described below) associated with handle assembly 512 which serves to disengage rack lock 580 and pawl 544 from actuation shaft 540 to permit the user to draw the actuation shaft in a proximal direction, as illustrated in FIG. 33.

Referring back to FIG. 18, the retraction mechanism preferably includes a pair of retractor knobs 760a and 760b which are connected to the proximal end of actuation shaft 540 by a coupling rod 762. Coupling rod 762 includes right and left engagement portions 764a and 764b for receiving retractor knobs 760a and 760b and a central portion 764c which is dimensioned and configured to translate within a pair of longitudinal slots 766a and 766b formed in actuation shaft 540 adjacent the proximal end thereof. A release plate 768 is operatively associated with actuation shaft 540 and is mounted for movement with respect thereto in response to manipulation of retractor knobs 760a and 760b. More particularly, a pair of spaced apart pins 767a and 767b extend outwardly from a lateral face of actuation shaft 540 to engage a pair of corresponding angled cam slots 769a and 769b formed in release plate 768. The cam slots define the path through which the release plate moves with respect to the actuation shaft 540, and more specifically, with respect to the toothed rack 542. A transverse slot 770 is formed at the proximal end of release plate 768 to accommodate the central portion 760c of coupling rod 762, and elongated slots 772 and 774 are defined in the barrel section 522 of handle assembly 520 to accommodate the longitudinal translation of coupling rod 762 as retraction knobs 760a and 760b move in conjunction with actuation shaft 540. Coupling rod 762 is biased distally by spring 765a which is secured at ine end to coupling rod portion 764c and at the other end to post 765b on actuation shaft 540.

Referring again to FIG. 33, when it is desirable to open anvil 536 to release the clamped body tissue 750, the user of apparatus 500 pulls retraction knobs 760a and 760b proximally, whereupon release plate 768 translates in a generally proximal direction along the path of angled cam slots 769a and 769b (see generally FIGS. 39 and 40). Consequently, the release plate urges the engagement hook 752 of rack lock 580 out of keeper notch 754 an forces pawl 544 out of engagement with toothed rack 542. At such a time, the user can draw actuation shaft 540 in a proximal direction, causing cam roller 680 to be drawn proximally with actuation beam 662. As a result, anvil 536 moves to an open position under the bias of anvil spring 676 and actuation handle 526 returns to a neutral position under the bias of torsion spring 538. Once actuation shaft 540 has been returned to its proximalmost position, stapling apparatus 500 is in a reset condition.

Figure 34:
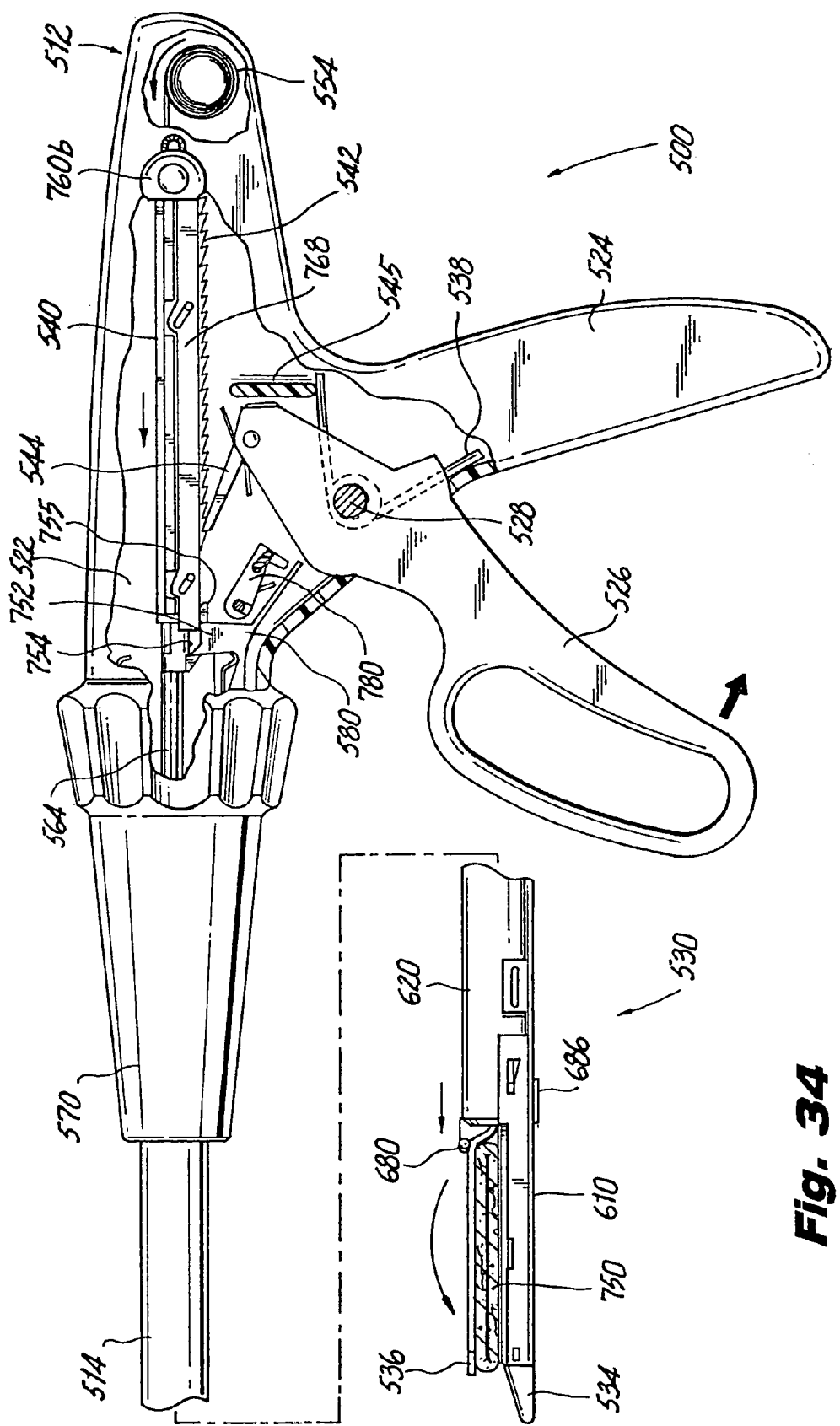
FIG. 34 corresponds to FIG. 32 and illustrates the surgical stapling apparatus with the anvil in a closed position after the actuation handle has been manipulated through a clamping stroke.
Figure 35:
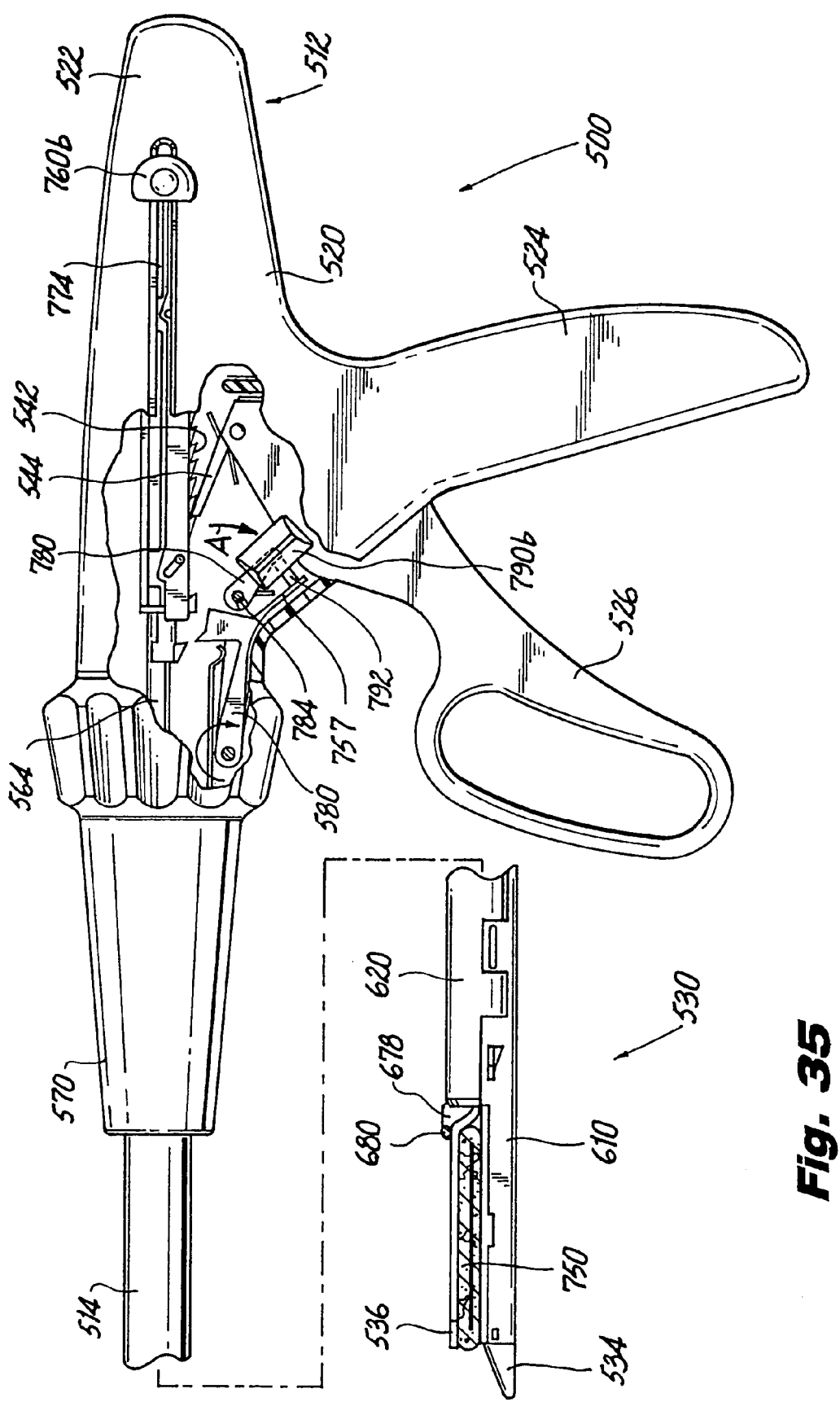
FIG. 35 is a side elevational view in partial cross-section of the surgical stapling apparatus of FIG. 17 illustrating the manual release of the rack lock to permit distal translation of the actuation shaft during subsequent stapling strokes.
Figure 43:
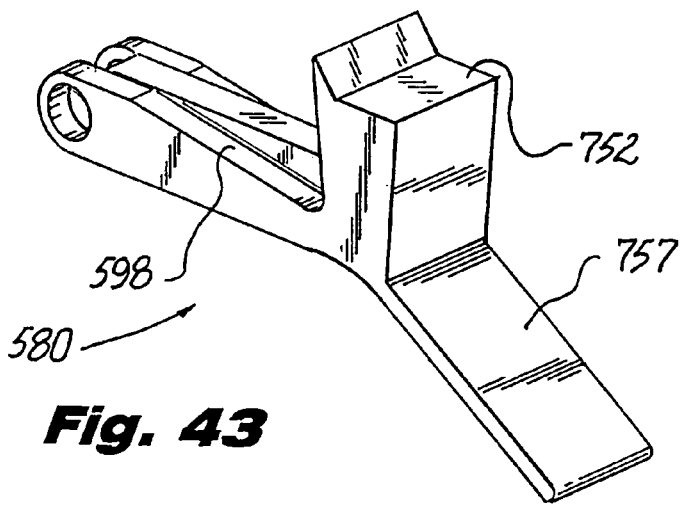
FIG. 43 is an enlarged perspective view of the rack lock (or engagement member) illustrating the structural geometry thereof.

Referring now to FIG. 34, to clamp body tissue 750 once again, actuation handle 526 is manipulated through the clamping segment of an actuation stroke to drive actuation shaft 540 distally until the engagement hook 752 of rack lock 580 is once again engaged in keeper notch 754 and in abutment with buttress 755. If, at such a time, the user of apparatus 500 is confident that the stapling procedure can commence, rack lock 580 must be manually released from keeper notch 754 to permit subsequent distal movement of actuation shaft 540. This is accomplished by way of a manual release mechanism operatively associated with handle assembly 512 which interacts with the proximal release tail 757 of rack lock 580, as shown in FIG. 35. The details of a preferred construction of rack lock (or engagement member) 580 are illustrated in FIG. 43.

Referring back once again to FIG. 18, the manual release mechanism preferably includes a pivoting release member 780 mounted on a boss 784 and biased away from the release tail 757 of rack lock 580 by a coiled torsion spring 786. A pair of opposed winglets, i.e., winglet 788, project laterally from release member 780 to support release knobs 790a and 790b, respectively. Release member 780 has a downturned nose 792 which is dimensioned to contact the release tail 757 of rack lock 580 when release knobs 790a and 790b are manipulated by the user in the direction indicated by arrow "A" in FIG. 35.

Referring once again to FIG. 35, upon manipulation of release knobs 790a and 790b and the consequential liberation of rack lock 580, actuation shaft 540 is free to translate in a distal direction in response to manipulation of actuation handle 526. At such a time, the linear position of actuation shaft 540 is maintained through the engagement of pawl 544 and toothed rack 542.

Figure 36:
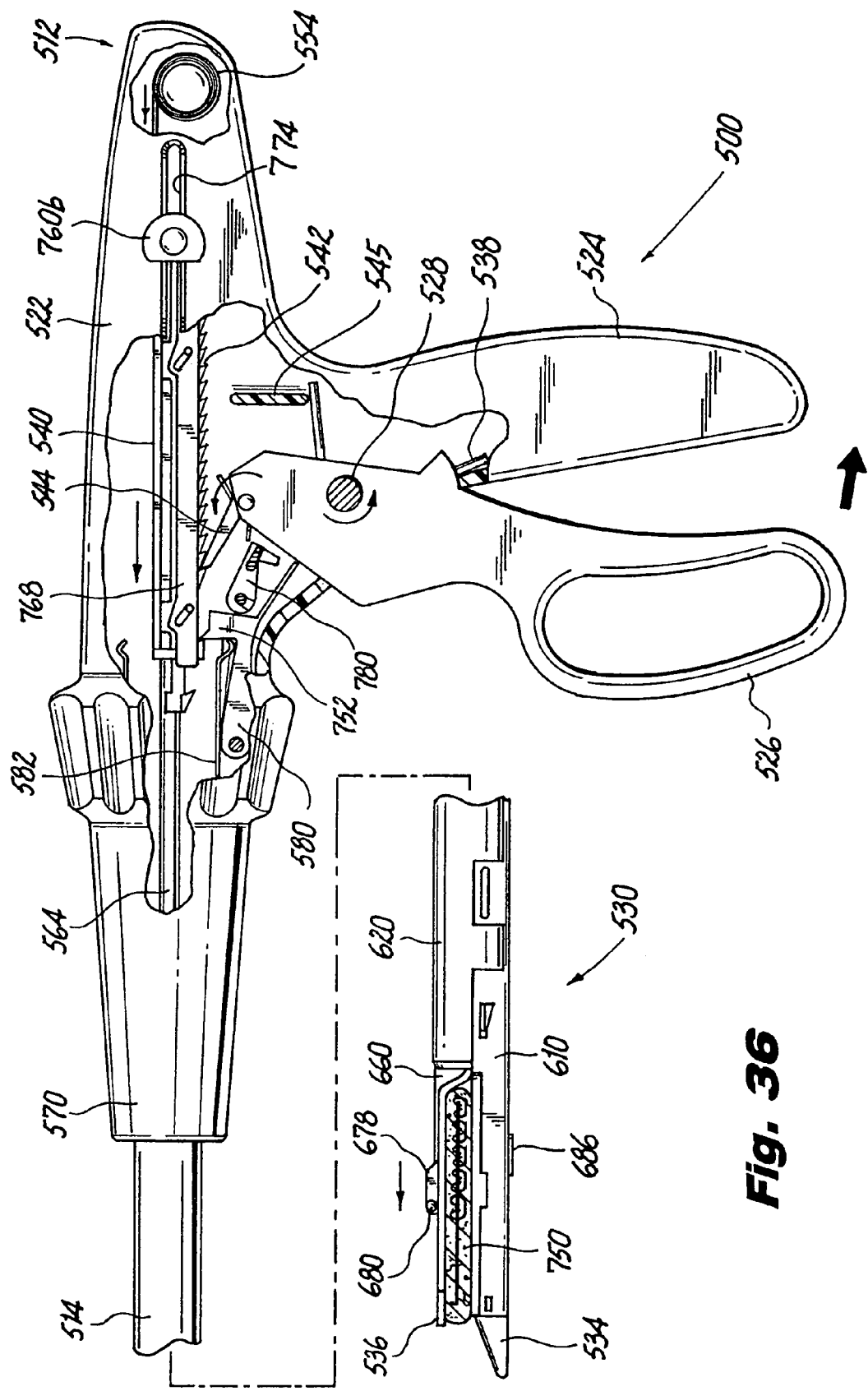
FIG. 36 is a side elevational view in partial cross-section of the surgical stapling apparatus of FIG. 17 illustrating the actuation shaft and toothed rack advanced distally in response to a complete stapling stroke of the actuation handle to effectuate partial sequential ejection of staples from the cartridge.

Turning to FIG. 36, manipulation of actuation handle 526 toward stationary handle 524 through a stapling stroke segment causes pawl 544 to advance toothed rack 542, and hence actuation shaft 540 and control rod 564, in a distal direction. As a result, the axial drive assembly 660 supported within loading unit 530 is driven distally to cause actuation sled 640 to intersect with pushers 643 to sequentially eject staples from cartridge 534. At the same time, knife blade 674 travels behind actuation sled 640, forming an incision in the stapled body tissue. As shown in FIG. 36, one complete stapling stroke effects firing of only a portion of the staples within cartridge 534. As previously described, multiple partial strokes can also be used to incrementally advance drive rod 564, i.e. pawl 544 can advance rack 542 one tooth at a time.

Figure 37:
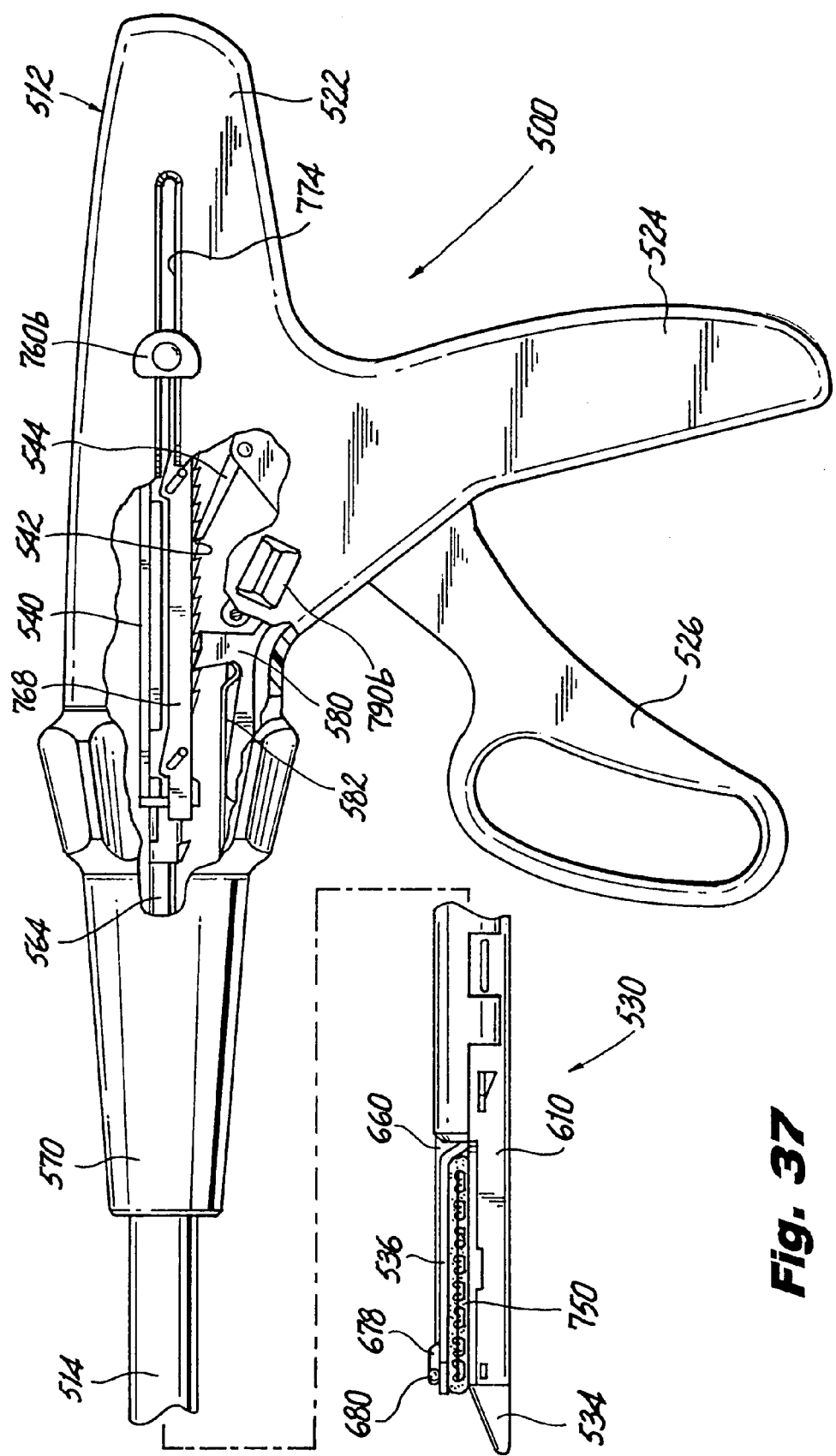
FIG. 37 is a side elevational view in partial cross-section of the surgical stapling apparatus of FIG. 17 illustrating the actuation shaft and toothed rack advanced distally in response to a second complete stapling stroke of the actuation handle to complete the sequential ejection of the staples from the cartridge.

Referring to FIG. 37, all of the staples within cartridge 534 are ejected and applied to tubular vessel 750. If a loading unit having a greater length had been employed with stapling apparatus 500, additional stapling strokes would have been required to advance actuation shaft 540 further. In total, the toothed rack 542 of actuation shaft 540 is preferably dimensioned to accommodate at least four complete stapling strokes of 15 mm each. Thus, if each complete stapling stroke of actuation handle 526 advances the actuation shaft 15 mm, stapling apparatus 500 can be used to fire disposable loading units that are configured to apply staple lines of 15 mm, 30 mm, 45 mm, and 60 mm using a whole number of complete strokes.

Figure 38:
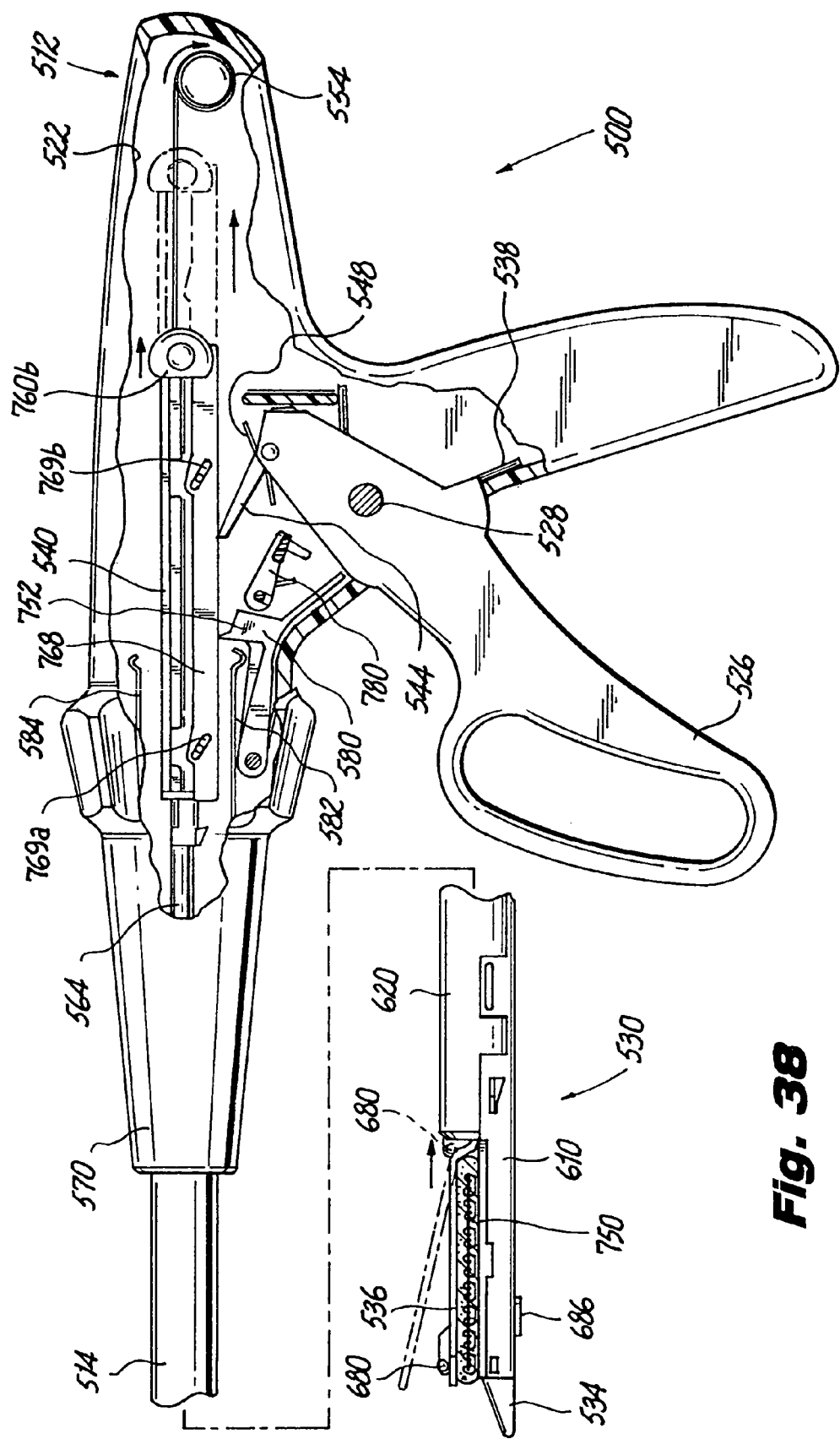
FIG. 38 is a side elevational view in partial cross-section of the surgical stapling apparatus of FIG. 17 illustrating the disengagement of the rack lock and pawl from the toothed rack by the release plate as the retraction knobs are pulled proximally to withdraw the actuation shaft and permit the anvil to move from the closed position shown in FIG. 37 to an open position.
Figure 41:
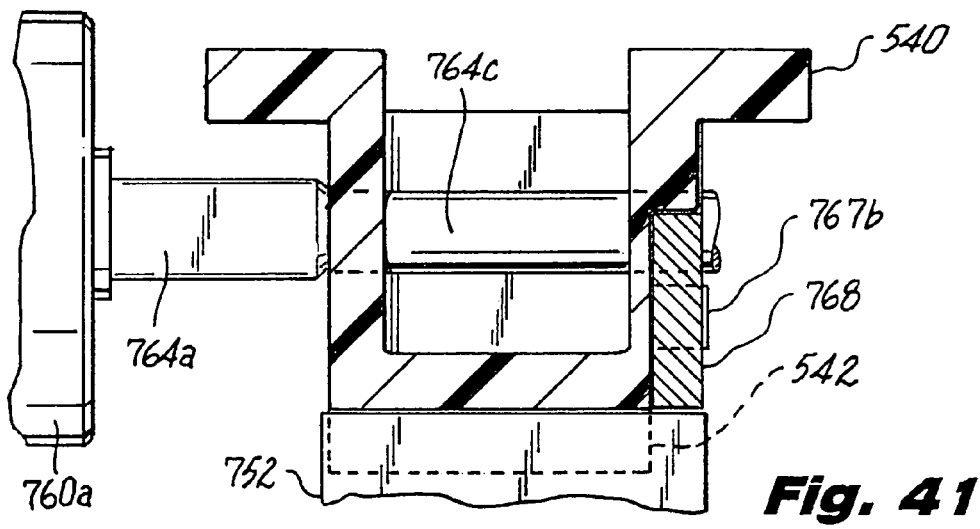
FIG. 41 is a cross-sectional view taken along line 41—41 of FIG. 39.
Figure 42:
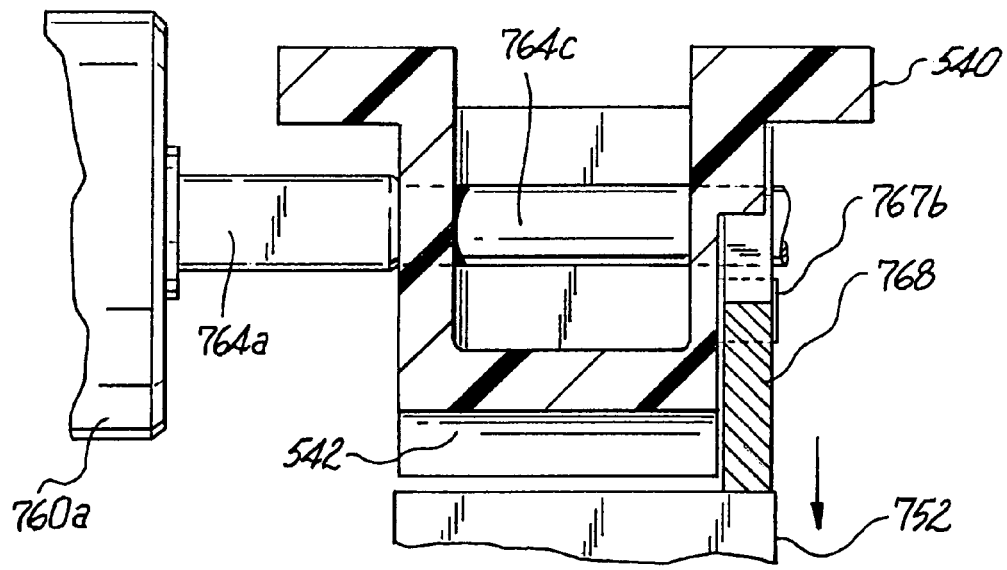
FIG. 42 is a cross-sectional view taken along line 42—42 of FIG. 40.

Referring now to FIG. 38, at the conclusion of the stapling procedure, to move anvil 536 to an open position and release stapled body tissue 750 from surgical apparatus 500, the user once again employs the retraction knobs 760a and 760b associated with the barrel portion 522 of handle assembly 520. More particularly, as best seen in FIGS. 39–42 proximal retraction of knobs 760a and 760b causes coupling rod 762 (FIG. 18) to translate proximally within the longitudinal slots 766a and 766b formed at the proximal end of actuation shaft 540. As a result, release plate 768 translates along an angled path defined by cam slots 769a and 769b, urging the engagement hook 752 of rack lock 580 and the pawl 544 (not shown) out of engagement with toothed rack 542. Thereupon, as illustrated in FIG. 38, actuation shaft 540 is free to translate in a proximal direction under the bias of the user and constant force spring 554. Consequently, the axial drive assembly 660 within disposable loading unit 530 is drawn proximally by the head of control rod 564, and anvil 536 moves to an open position as cam roller 680 is retracted.

Figure 50:
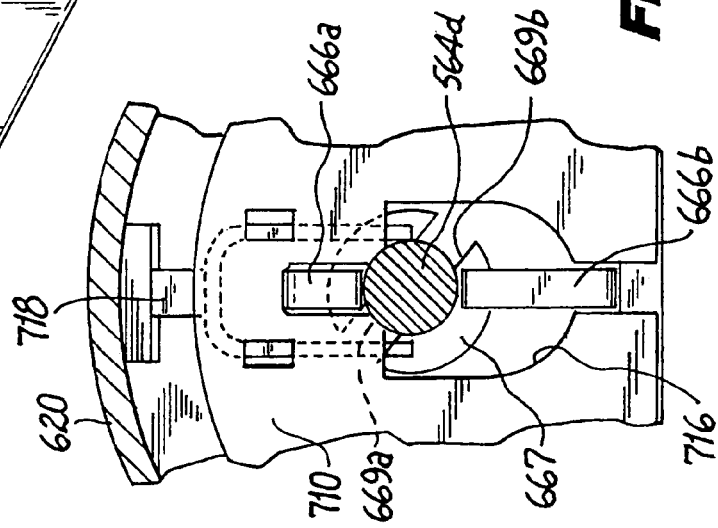
FIG. 50 is a cross-sectional view taken along line 50—50 of FIG. 46 illustrating the relative positions of the blocking plate and control rod prior to the removal of the disposable loading unit from the distal end of the body portion.

Referring now to FIG. 45, as control rod 564 is withdrawn in a proximal direction from its distal-most position illustrated in FIG. 44, blocking plate 710 rides along control rod 564 and is maintained in an upright position against the bias of retention spring 718. However, as illustrated in FIG. 46, as reduced diameter distal end portion 564d of control rod 564 approaches its proximal-most position, blocking plate 710 is urged toward the control rod such that the peripheral edge of aperture 716 engages distal end portion 564d of control rod 564 (see also FIG. 50). Further proximal movement of control rod 564 draws drive block 668 to its proximal-most position illustrated in FIG. 47, wherein flange 667 interacts with camming ramps 762a and 762b of retention spring 718 and at least partially lifts blocking plate 710. At such a time, distal movement of control rod 564 is limited due to interaction between blocking plate 710 and the larger diametered ledge where the proximal end of 564d meets the larger diameter of rod 564. However, control rod 564 is still afforded a limited range of longitudinal motion along reduced diameter portion 564d of control rod 564 so that anvil 536 can be moved between open and closed positions. Accordingly, anvil 536 may be easily closed to facilitate removal of surgical apparatus 500 through a trocar or cannula device.

Figure 47:
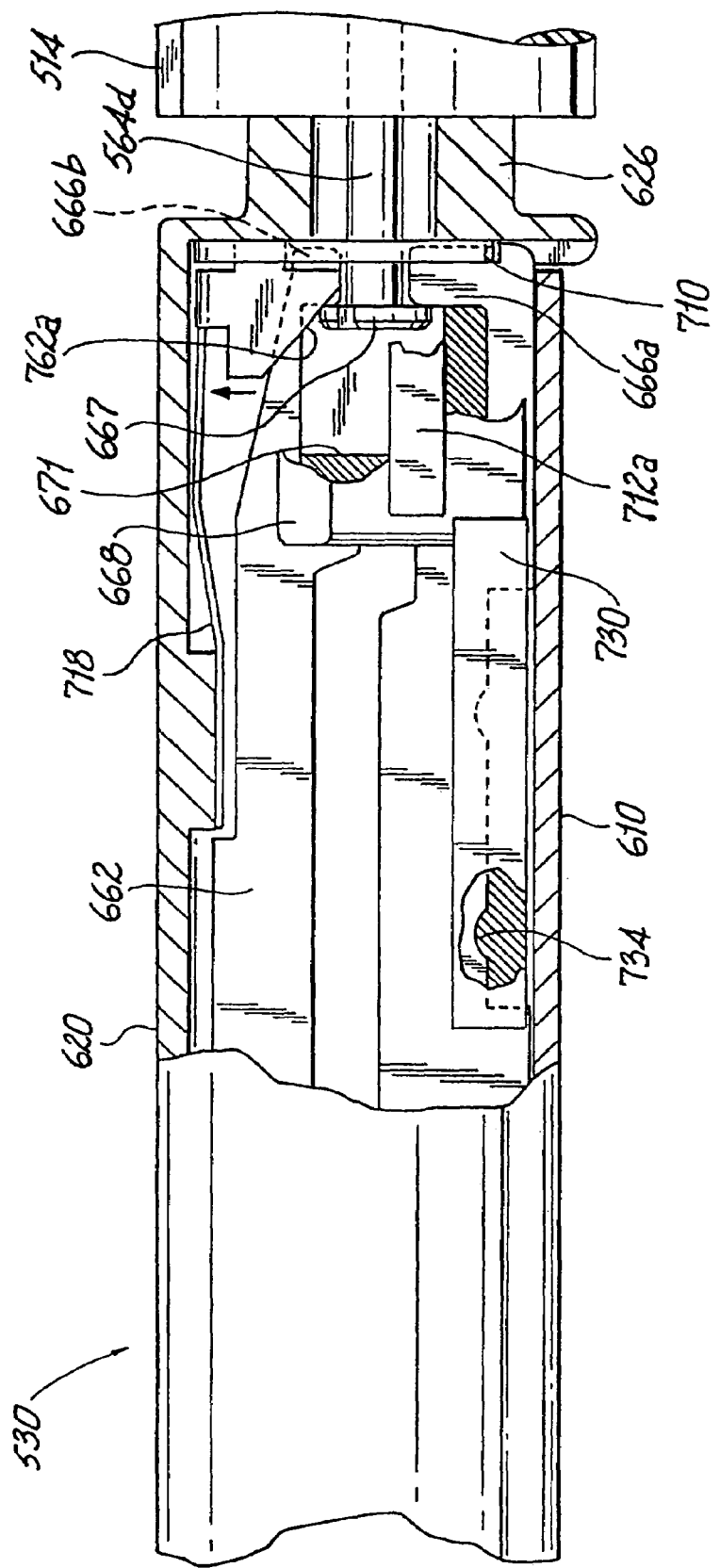
FIG. 47 is a side elevational view in partial cross-section of the disposable loading unit of FIG. 24 illustrating the orientation of the lockout assembly components when the control rod has been withdrawn to its proximal-most position.

As best seen in FIG. 47, when axial drive assembly 660 and the drive block 668 associated therewith assume their proximal-most position, the detent 734 on support plate 730 engages distal recess 735*a*. At such a time, support plate 730 is securely retained in its final rest position to prevent the plate from floating within disposable loading unit 530 after it has been removed from surgical apparatus 500.

Figure 51:
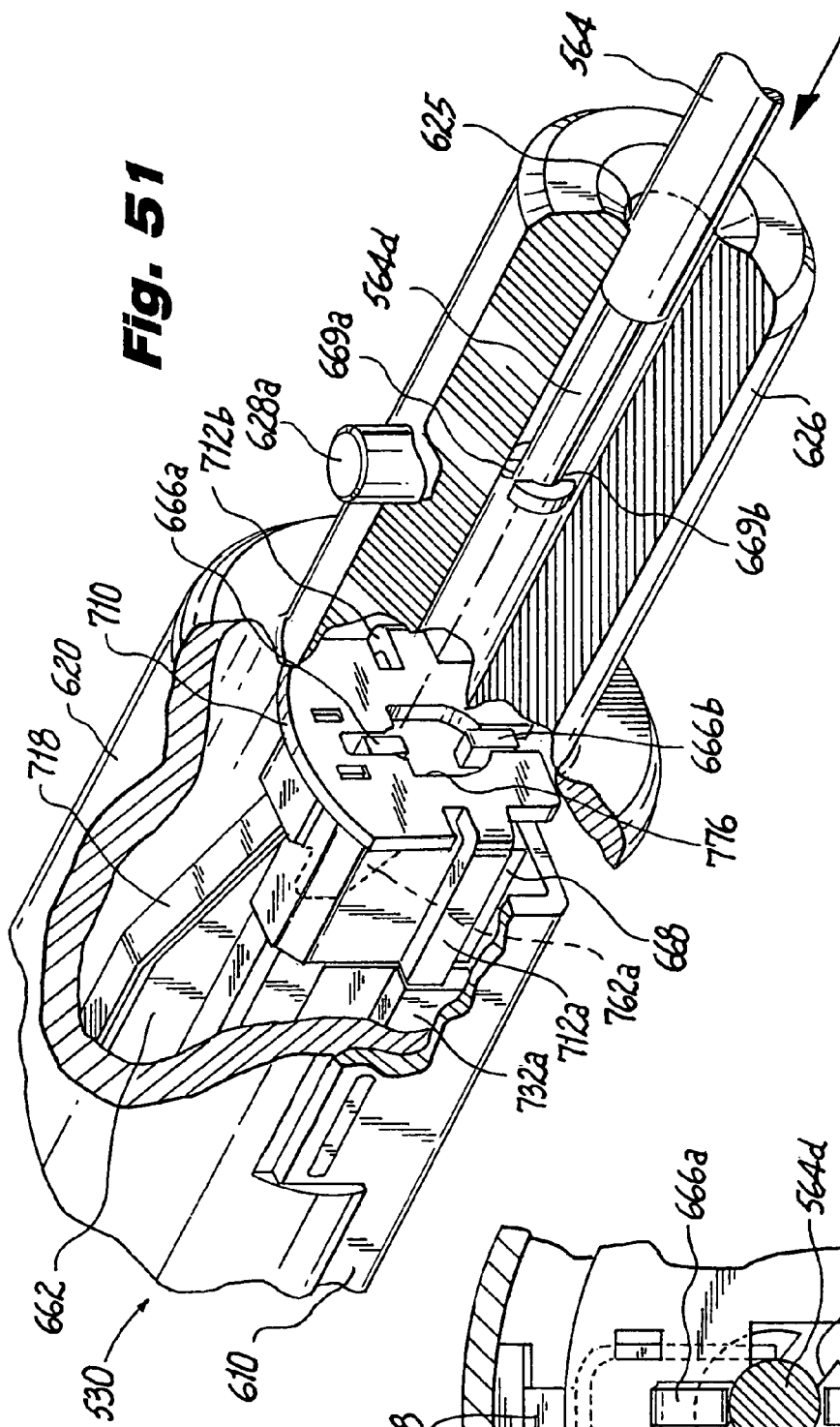
FIG. 51 is an enlarged perspective view in partial cross-section of the disposable loading unit after it has been removed from the distal end of the body portion illustrating the lockout assembly in a blocking position to prevent entry of the distal end of the control rod into the drive block of the axial drive assembly.

Referring to FIG. 48, to remove disposable loading unit 530 from the distal end of body portion 514, the loading unit is shifted proximally and rotated to disengage the bayonet coupling. Simultaneously, the engagement fingers 666*a* and 666*b* are re-aligned with the notches 669*a* and 669*b* in flange 667. The flange can now further bias locking plate 710 upward, allowing for the removal of disposable loading unit 530 from the distal end of body portion 514. As soon as flange 667 moves past camming ramps 762*a* and 762*b* and blocking plate 710, the blocking plate is free to translate into a full blocking position under the bias of retention spring 718. In this position, which is best seen in FIG. 51, entry of the distal end of control rod 564 into the proximal portal 670 of drive block 668 is advantageously prohibited. Accordingly, a fired or partially fired disposable loading unit cannot be subsequently utilized after it has been removed from surgical apparatus 500.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. A surgical stapler comprising:
   a) a handle assembly including a pivotable handle mounted for manipulation through at least one actuating stroke;
   b) an elongated body extending distally from the handle assembly and defining a longitudinal axis;
   c) a channel disposed adjacent the distal end of the elongated body;
   d) a staple cartridge configured and dimensioned to be supported by the channel, the staple cartridge containing a plurality of staples;
   e) an anvil pivotally mounted in relation to the cartridge adjacent the distal end of the elongated body, the anvil having a fastener forming surface thereon and being mounted for pivotal movement in relation to the cartridge;
   f) an actuation sled positioned in the staple cartridge, the actuation sled being movable to eject the plurality of staples from the staple cartridge;
   g) a drive assembly including a drive member having a working end and a cam member on the working end, the cam member being positioned to engage the anvil to effectuate progressive closure of the anvil against tissue, the pivotable handle being operably connected to the drive assembly such that manipulation of the pivotable handle through at least one actuating stroke effects translation of the cam member relative to the anvil; and
   h) a flange member supported at the working end of the drive member, the flange member being positioned to engage the channel.

2. A surgical stapler according to claim 1, wherein the actuation sled includes a plurality of cam surfaces and is movable through the staple cartridge to urge the plurality of staples from the staple cartridge.

3. A surgical stapler according to claim 2, wherein the working end of the drive member is positioned to abut the actuation sled to effect translation of the actuation sled through the staple cartridge.

4. A surgical stapler according to claim 3, wherein the staple cartridge includes a plurality of spaced apart retention slots, each of the retention slots supporting one of the plurality of staples.

5. A surgical stapler according to claim 1, wherein the drive assembly includes a rack and the pivotable handle includes a pawl configured to engage the rack to advance the drive member in response to manipulation of the pivotable handle.

6. A surgical stapler according to claim 1, wherein the anvil includes an anvil cover that defines a channel, the cam member traveling in the channel.

7. A surgical stapler according to claim 1, wherein the flange member engages the channel to balance clamping forces generated by the cam member as the anvil is progressively closed.

8. A surgical stapler according to claim 1, wherein the drive member supports a knife blade at the working end.

9. A surgical stapler according to claim 8, wherein the drive member has a surface for abutting the actuation sled in the cartridge, the actuation sled causing staples to be driven from the cartridge.

10. A surgical stapler comprising:
    a) a handle assembly including a pivotable handle mounted for manipulation through at least one actuating stroke;
    b) an elongated body extending distally from the handle assembly and defining a longitudinal axis;
    c) a channel disposed at the distal end of the elongated body;
    d) a staple cartridge configured and dimensioned to be supported by the channel, the staple cartridge containing a plurality of staples arranged in a plurality of rows and at least one slot disposed between the rows of staples;
    e) an anvil pivotally mounted in relation to the cartridge adjacent the distal end of the elongated body, the anvil having a fastener forming surface thereon;
    f) an actuation sled positioned in the staple cartridge, the actuation sled being movable through the cartridge to cooperate with staple pushers to eject the plurality of staples from the staple cartridge; and
    g) a drive assembly including a drive beam having an anvil engaging member and a balancing flange, the pivotable handle being operably connected to the drive assembly such that manipulation of the pivotable handle through at least one actuating stroke effects translation of the drive beam through the staple cartridge slot, whereby the balancing flange and the anvil engaging member together effect progressive clamping of the anvil and cartridge and advancement of the actuation sled through the staple cartridge.

11. A surgical stapler according to claim 10, wherein the actuation sled includes a plurality of cam surfaces.

12. A surgical stapler according to claim 10, wherein the drive beam has a surface positioned to abut the actuation sled to effect translation of the actuation sled through the staple cartridge.

13. A surgical stapler according to claim 10, wherein the drive assembly includes a rack and the pivotable handle includes a pawl configured to engage the ract to advance the drive beam in response to manipulation of the pivotable handle.

14. A surgical stapler according to claim 10, wherein the anvil includes an anvil cover that defines an anvil channel, the anvil engaging member translating through the anvil channel during the actuating stroke.

15. A surgical stapler according to claim 10, wherein the balancing flange engages the channel to balance clamping forces generated during progressive clamping of the anvil and cartridge.

16. A surgical stapler according to claim 10, wherein the drive beam supports a knife blade.

17. A surgical stapler according to claim 16, wherein the drive beam includes a strut and the knife blade is supported by the strut, such that the knife blade translates through the cartridge slot during the actuating stroke.

18. A surgical stapler according to claim 10, wherein the anvil engaging member is a cam.

* * * * *